(12) United States Patent
Kurihara et al.

(10) Patent No.: US 11,129,893 B2
(45) Date of Patent: Sep. 28, 2021

(54) PHARMACEUTICAL COMPOSITION FOR TREATING AND/OR PREVENTING CANCER

(71) Applicant: TORAY INDUSTRIES, INC., Tokyo (JP)

(72) Inventors: Akira Kurihara, Kamakura (JP);
Hyongi Chon, Kamakura (JP);
Takayuki Fujita, Kamakura (JP);
Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 102 days.

(21) Appl. No.: 15/567,496

(22) PCT Filed: Apr. 28, 2016

(86) PCT No.: PCT/JP2016/063420
§ 371 (c)(1),
(2) Date: Oct. 18, 2017

(87) PCT Pub. No.: WO2016/175307
PCT Pub. Date: Mar. 11, 2016

(65) Prior Publication Data
US 2018/0085453 A1 Mar. 29, 2018

(30) Foreign Application Priority Data
Apr. 30, 2015 (JP) .............................. JP2015-093640

(51) Int. Cl.
| | | |
|---|---|---|
| A61K 39/395 | (2006.01) | |
| C07K 16/28 | (2006.01) | |
| A61P 35/02 | (2006.01) | |
| C07K 4/12 | (2006.01) | |
| A61K 39/00 | (2006.01) | |

(52) U.S. Cl.
CPC ............ *A61K 39/395* (2013.01); *A61P 35/02* (2018.01); *C07K 4/12* (2013.01); *C07K 16/2803* (2013.01); *A61K 2039/505* (2013.01); *C07K 2317/70* (2013.01); *C07K 2317/732* (2013.01); *C07K 2317/734* (2013.01)

(58) Field of Classification Search
CPC .................................................... A61K 39/395
USPC ...................................................... 424/131.1
See application file for complete search history.

(56) References Cited

U.S. PATENT DOCUMENTS

| | | | |
|---|---|---|---|
| 5,698,396 A | 12/1997 | Pfreundschuh | |
| 2005/0106644 A1 | 5/2005 | Cairns et al. | |
| 2008/0124331 A1* | 5/2008 | Cairns ................ | A61K 51/1006 424/138.1 |
| 2011/0129478 A1 | 6/2011 | Okano et al. | |
| 2011/0256144 A1 | 10/2011 | Okano et al. | |

FOREIGN PATENT DOCUMENTS

| | | |
|---|---|---|
| CN | 102089004 A | 6/2011 |
| CN | 102170907 A | 8/2011 |
| EP | 2 011 869 A1 | 1/2009 |
| EP | 2 305 300 A1 | 4/2011 |
| EP | 2 322 221 A1 | 5/2011 |
| EP | 2 452 950 A1 | 5/2012 |
| JP | 9-194502 A | 7/1997 |
| JP | 2007-204473 A | 8/2007 |
| JP | 2013-13327 A | 1/2013 |
| WO | WO 2007/114496 A1 | 10/2007 |
| WO | WO 2010/005068 A1 | 1/2010 |
| WO | WO 2010/016526 A1 | 2/2010 |
| WO | WO 2011/004837 A1 | 1/2011 |
| WO | WO 2012/027570 A4 | 3/2012 |

OTHER PUBLICATIONS

Ahmad et al (Clinical and Developmental Immunology, 2012, 1-15).*
Tanaka et al (JBC, 2006, 281(41): 30857-30864).*
Cosmo Bio Co. LTD. Product data sheet for antibody C1; https://search.cosmobio.co.jp/cosmo_search_p/search_gate2/docs/CAC_/NU07003.20130123.pdf; downloaded Jun. 27, 2018.*
Byers, T. (CA Journal, vol. 49, No. 6, Nov./Dec. 1999).*
Bruggen et al., "A Gene Encoding an Antigen Recognized by Cytolytic T Lymphocytes on a Human Melanoma", Science, vol. 254, Dec. 13, 1991, pp. 1643-1647.
Gure et al., "SSX: A Multigene Family with Several Members Transcribed in Normal Testis and Human Cancer", Int. J. Cancer, vol. 72, 1997, pp. 965-971.
International Search Report for PCT/JP2016/063420 (PCT/ISA/210) dated Jun. 28, 2016.
Sahin et al., "Human neoplasms elicit multiple specific immune responses in the autologous host", Immunology, Proc. Natl. Acad. Sci. USA, vol. 92, 1995, pp. 11810-11813.
Watanabe et al., "Neuroglycan C, a Novel Membrane-spanning Chondroitin Sulfate Proteoglycan That Is Restricted to the Brain", The Journal of Biological Chemistry, Nov. 10, 1995, vol. 270, pp. 26876-26882.
Written Opinion of the International Searching Authority for PCT/JP2016/063420 (PCT/ISA/237) dated Jun. 28, 2016.

(Continued)

*Primary Examiner* — Sean E Aeder
(74) *Attorney, Agent, or Firm* — Birch, Stewart, Kolasch & Birch, LLP

(57) ABSTRACT

An object of the present invention is to identify a cancer antigen protein specifically expressed on the surface of cancer cells and provide use of an antibody targeting the cancer antigen protein as a therapeutic and/or prophylactic agent for cancer. A pharmaceutical composition for treating and/or preventing cancer comprising an antibody or a fragment thereof having immunological reactivity with CSPG5 protein consisting of any one of amino acid sequences represented by SEQ ID NOs: 8, 4, 6, 10, and 12 and an amino acid sequence having an amino acid identity of 80% or more to the amino acid sequence, or a fragment thereof consisting of 7 or more consecutive amino acids, as an active ingredient.

19 Claims, 5 Drawing Sheets

Specification includes a Sequence Listing.

(56) References Cited

OTHER PUBLICATIONS

Wu et al., "Expression of ErbB Receptors and their Cognate Ligands in Gastric and Colon Cancer Cell Lines", Anticancer Research, vol. 29, 2009, pp. 229-234.
Russian Office Action and Search Report, dated Sep. 4, 2019 for Russian Application No. 2017135005/04.
"NP_001193872.1," GenBank So, H. C., Mar. 15, 20215, 5 pages.
"NP_001193873.1," GenBank, So, H. C., Mar. 15, 2015, 5 pages.
"NP_006565.2," Genbank, So, H. C., Mar. 15, 2015, 5 pages.
Office Action dated May 28, 2020, in Chinese Patent Application No. 201680023169.6.
Office Action dated May 3, 2021, in Indian Patent Application No. 201737035853.

* cited by examiner

SEQUENCE LISTING

```
<160> NUMBER OF SEQ ID NOS: 33

<210> SEQ ID NO 1
<211> LENGTH: 2270
<212> TYPE: DNA
<213> ORGANISM: Canis familiaris
<220> FEATURE:
<221> NAME/KEY: CDS
<222> LOCATION: (1)..(1434)
<223> OTHER INFORMATION:

<400> SEQUENCE: 1 ggg gag gag gag acc tcg tgt act gca cct ggc ggc ctg ccg gcc gtg        48
Gly Glu Glu Glu Thr Ser Cys Thr Ala Pro Gly Gly Leu Pro Ala Val
1               5                   10                  15 gtg ggg cct ggg gtc ggg cca gag gag gcg ctg gag gcg tcc gcg gcc        96
Val Gly Pro Gly Val Gly Pro Glu Glu Ala Leu Glu Ala Ser Ala Ala
            20                  25                  30 gtg acc ggc aca gcc tgg ctg gag gct gac agc ccg ggc ctg ggc gga       144
Val Thr Gly Thr Ala Trp Leu Glu Ala Asp Ser Pro Gly Leu Gly Gly
        35                  40                  45 gcg acc gta gag gct ggc agc ggc gac acc cag gcc ctt ccg gcc acg       192
Ala Thr Val Glu Ala Gly Ser Gly Asp Thr Gln Ala Leu Pro Ala Thr
    50                  55                  60 ctc ccg act ccg gag gag gcc ctc cga cgt gca tcg gtg gcc ccc gcc       240
Leu Pro Thr Pro Glu Glu Ala Leu Arg Arg Ala Ser Val Ala Pro Ala
65                  70                  75                  80 acc ccc gag act aca gag gcc agc gga cca ccc tcc ccc act cct ggc       288
Thr Pro Glu Thr Thr Glu Ala Ser Gly Pro Pro Ser Pro Thr Pro Gly
                85                  90                  95 gac cag cta cgc cca ggc ccc gaa ctc ccc aag gag agc ccc ttg gag       336
```

```
                Asp Gln Leu Arg Pro Gly Pro Glu Leu Pro Lys Glu Ser Pro Leu Glu
                            100                 105                 110 gtt tgg ctg aac ctg gga ggc agc aca cat gac ccg cat ggg cca gag      384
Val Trp Leu Asn Leu Gly Gly Ser Thr His Asp Pro His Gly Pro Glu
            115                 120                 125 ccc acg ttc ccc ttt cag ggc aca ctg gag ccc cgg ccg gcg tca gat      432
Pro Thr Phe Pro Phe Gln Gly Thr Leu Glu Pro Arg Pro Ala Ser Asp
        130                 135                 140 atc att gac atc gac tac ttc gaa gga ttg gat ggt gag ggc cgt ggc      480
Ile Ile Asp Ile Asp Tyr Phe Glu Gly Leu Asp Gly Glu Gly Arg Gly
145                 150                 155                 160 gcc gac ttg ggg agc ttc ccg gtg tcg cca gga acc tca gag cac cac      528
Ala Asp Leu Gly Ser Phe Pro Val Ser Pro Gly Thr Ser Glu His His
                165                 170                 175 ccc gat act ggg gga gag acc cct tcc tgg agc ctg ctt gac tta tac      576
Pro Asp Thr Gly Gly Glu Thr Pro Ser Trp Ser Leu Leu Asp Leu Tyr
            180                 185                 190 gat gac ttc acc ccc ttt gat gaa tct gac ttc tac ccc act aca tcc      624
Asp Asp Phe Thr Pro Phe Asp Glu Ser Asp Phe Tyr Pro Thr Thr Ser
        195                 200                 205 ttc tat gat gac ttg gag gaa gag gag gaa gag gat gac gac aag          672
Phe Tyr Asp Asp Leu Glu Glu Glu Glu Glu Glu Asp Asp Asp Lys
210                 215                 220 gat gca gcg gaa ggt gga gac ctg gaa gat gaa agt gac ctt ctg gtg      720
Asp Ala Ala Glu Gly Gly Asp Leu Glu Asp Glu Ser Asp Leu Leu Val
225                 230                 235                 240 ccc act gag aag cct ggg ctg agg cca ggg cct ggc cag ccc acc agt      768
Pro Thr Glu Lys Pro Gly Leu Arg Pro Gly Pro Gly Gln Pro Thr Ser
                245                 250                 255 cgg tgg cat gct gtc ccc cca cag cat act ctg ggg ttg gtc cct ggc      816
Arg Trp His Ala Val Pro Pro Gln His Thr Leu Gly Leu Val Pro Gly
            260                 265                 270 agc agc atc gcc ctc aga ccc cgt ccg gga gag ccg ggc agg gac ctg      864
Ser Ser Ile Ala Leu Arg Pro Arg Pro Gly Glu Pro Gly Arg Asp Leu
        275                 280                 285 gcc ccg agc gag aac ggc act gag tgc cgc agc ggc ttt gtg cgg cat      912
Ala Pro Ser Glu Asn Gly Thr Glu Cys Arg Ser Gly Phe Val Arg His
    290                 295                 300 aac ggc tcc tgc cga tcc gtg tgc gac ctc ttc cca agt tac tgt cac      960
Asn Gly Ser Cys Arg Ser Val Cys Asp Leu Phe Pro Ser Tyr Cys His
305                 310                 315                 320 aac ggc ggc cag tgc tac ctg gtg gac aac ata ggg gcc ttc tgc agg     1008
Asn Gly Gly Gln Cys Tyr Leu Val Asp Asn Ile Gly Ala Phe Cys Arg
                325                 330                 335 tgt aac aca cag gac tac atc tgg cac aag ggg atg cgc tgc gag tcc     1056
Cys Asn Thr Gln Asp Tyr Ile Trp His Lys Gly Met Arg Cys Glu Ser
            340                 345                 350 atc atc acc gac ttc cag gtg atg tgc gtg gcc gtc ggc tca gcc gcc     1104
Ile Ile Thr Asp Phe Gln Val Met Cys Val Ala Val Gly Ser Ala Ala
        355                 360                 365 ctc gtg ctg ctc ctg ctc ttc atg atg aca gtg ttc ttc gcc aag aag     1152
Leu Val Leu Leu Leu Leu Phe Met Met Thr Val Phe Phe Ala Lys Lys
    370                 375                 380 ctg tat ctg ctc aag aca gag aat acc aag ctg cgt agg acc aac aaa     1200
Leu Tyr Leu Leu Lys Thr Glu Asn Thr Lys Leu Arg Arg Thr Asn Lys
385                 390                 395                 400 ttc cgg acc ccg tct gag ctc cac aac gat aac ttc tcc ctt tcc acc     1248
Phe Arg Thr Pro Ser Glu Leu His Asn Asp Asn Phe Ser Leu Ser Thr
                405                 410                 415
```

| | | | | | | | | | | | | | | | | |
|---|---|---|---|---|---|---|---|---|---|---|---|---|---|---|---|---|
| att | gcc | gaa | ggc | tct | cac | cca | aac | gac | gat | ccc | agt | gct | tcc | cac | aaa | 1296 |
| Ile | Ala | Glu | Gly | Ser | His | Pro | Asn | Asp | Asp | Pro | Ser | Ala | Ser | His | Lys | |
| | | | 420 | | | | 425 | | | | | 430 | | | | |
| atc | cag | gag | gtt | ctc | aag | tcc | tgc | ctg | aaa | gag | gag | gag | tca | ttt | aac | 1344 |
| Ile | Gln | Glu | Val | Leu | Lys | Ser | Cys | Leu | Lys | Glu | Glu | Glu | Ser | Phe | Asn | |
| | | 435 | | | | | 440 | | | | | 445 | | | | |
| atc | cag | aac | tcc | atg | tcc | ccc | aaa | ctg | gag | ggt | ggc | aaa | ggt | gac | cag | 1392 |
| Ile | Gln | Asn | Ser | Met | Ser | Pro | Lys | Leu | Glu | Gly | Gly | Lys | Gly | Asp | Gln | |
| | 450 | | | | | 455 | | | | | 460 | | | | | |
| gct | gac | ttg | gag | gtg | aac | tgt | ctt | cag | aac | aac | ctc | acc | taa | | | 1434 |
| Ala | Asp | Leu | Glu | Val | Asn | Cys | Leu | Gln | Asn | Asn | Leu | Thr | | | | |
| 465 | | | | 470 | | | | | 475 | | | | | | | | agcagagcaa gaagagaggg aatgggggag ggcggggggt ggcagggaa gaaacatgac 1494 ctcctcttgt acagagtcta tttcttgtaa ccatttgtta aactctcttc tttttctggt 1554 ctcatggcat gccttgatgt attttgtaca ggagggagaa aacacaaaat aagcaaagaa 1614 cctgaacaga atcgcataca ccgggttgtt tcgtctgtgc tgtctgtata ttgcttctgc 1674 tgctgtgatt tctaaaccta tgctgttatt caactgactt ttttttttgta ctttgaccca 1734 cctttttttg aaataagagt taaaaaacaa agttcttgaa ataaaacttt ttaaaaagcc 1794 attttccatc agtgtgtcca cttcctaccc attcttgtca gcttgagttg aattcttacg 1854 ttccctgaag atgtatattt atatgtgttt gaaatcctgg aagtgctctc tgtattagcc 1914 taggttgccg taactaaaca tcatagactg atcacttaa gcaatagaaa tttattttg 1974 aacagtaata gaggctggat ccccaagatc aaggtgccaa cagagttggt ttctggcagg 2034 gcctctctgc ctggcttgca aagagccatc ttcttgctat gtcctcacaa ggccttttgt 2094 ctgtgcacat ctcttcctct tctgataagg acaccagtcc tattggccta ggatccattt 2154 aacctcaatt acctcctcat aggccctact ccagatacag tcacacttag gggttatggc 2214 ttcaacatga cttttggggt gacataattc agtccacaag tctgtagcac ctgatt 2270

<210> SEQ ID NO 2
<211> LENGTH: 477
<212> TYPE: PRT
<213> ORGANISM: Canis familiaris

<400> SEQUENCE: 2

```
Gly Glu Glu Glu Thr Ser Cys Thr Ala Pro Gly Gly Leu Pro Ala Val
1               5                   10                  15

Val Gly Pro Gly Val Gly Pro Glu Glu Ala Leu Glu Ala Ser Ala Ala
            20                  25                  30

Val Thr Gly Thr Ala Trp Leu Glu Ala Asp Ser Pro Gly Leu Gly Gly
        35                  40                  45

Ala Thr Val Glu Ala Gly Ser Gly Asp Thr Gln Ala Leu Pro Ala Thr
    50                  55                  60

Leu Pro Thr Pro Glu Glu Ala Leu Arg Arg Ala Ser Val Ala Pro Ala
65                  70                  75                  80

Thr Pro Glu Thr Thr Glu Ala Ser Gly Pro Ser Pro Thr Pro Gly
                85                  90                  95

Asp Gln Leu Arg Pro Gly Pro Glu Leu Pro Lys Glu Ser Pro Leu Glu
            100                 105                 110

Val Trp Leu Asn Leu Gly Gly Ser Thr His Asp Pro His Gly Pro Glu
        115                 120                 125

Pro Thr Phe Pro Phe Gln Gly Thr Leu Glu Pro Arg Pro Ala Ser Asp
    130                 135                 140
```

```
Ile Ile Asp Ile Asp Tyr Phe Glu Gly Leu Asp Gly Glu Gly Arg Gly
145                 150                 155                 160

Ala Asp Leu Gly Ser Phe Pro Val Ser Pro Gly Thr Ser Glu His His
                165                 170                 175

Pro Asp Thr Gly Gly Glu Thr Pro Ser Trp Ser Leu Leu Asp Leu Tyr
            180                 185                 190

Asp Asp Phe Thr Pro Phe Asp Glu Ser Asp Phe Tyr Pro Thr Thr Ser
        195                 200                 205

Phe Tyr Asp Asp Leu Glu Glu Glu Glu Glu Asp Asp Asp Lys
    210                 215                 220

Asp Ala Ala Glu Gly Gly Asp Leu Glu Asp Glu Ser Asp Leu Leu Val
225                 230                 235                 240

Pro Thr Glu Lys Pro Gly Leu Arg Pro Gly Pro Gly Gln Pro Thr Ser
                245                 250                 255

Arg Trp His Ala Val Pro Pro Gln His Thr Leu Gly Leu Val Pro Gly
                260                 265                 270

Ser Ser Ile Ala Leu Arg Pro Arg Pro Gly Glu Pro Gly Arg Asp Leu
            275                 280                 285

Ala Pro Ser Glu Asn Gly Thr Glu Cys Arg Ser Gly Phe Val Arg His
290                 295                 300

Asn Gly Ser Cys Arg Ser Val Cys Asp Leu Phe Pro Ser Tyr Cys His
305                 310                 315                 320

Asn Gly Gly Gln Cys Tyr Leu Val Asp Asn Ile Gly Ala Phe Cys Arg
            325                 330                 335

Cys Asn Thr Gln Asp Tyr Ile Trp His Lys Gly Met Arg Cys Glu Ser
        340                 345                 350

Ile Ile Thr Asp Phe Gln Val Met Cys Val Ala Val Gly Ser Ala Ala
        355                 360                 365

Leu Val Leu Leu Leu Leu Phe Met Met Thr Val Phe Phe Ala Lys Lys
        370                 375                 380

Leu Tyr Leu Leu Lys Thr Glu Asn Thr Lys Leu Arg Arg Thr Asn Lys
385                 390                 395                 400

Phe Arg Thr Pro Ser Glu Leu His Asn Asp Asn Phe Ser Leu Ser Thr
                405                 410                 415

Ile Ala Glu Gly Ser His Pro Asn Asp Asp Pro Ser Ala Ser His Lys
                420                 425                 430

Ile Gln Glu Val Leu Lys Ser Cys Leu Lys Glu Glu Ser Phe Asn
            435                 440                 445

Ile Gln Asn Ser Met Ser Pro Lys Leu Glu Gly Lys Gly Asp Gln
            450                 455                 460

Ala Asp Leu Glu Val Asn Cys Leu Gln Asn Asn Leu Thr
465                 470                 475

<210> SEQ ID NO 3
<211> LENGTH: 2175
<212> TYPE: DNA
<213> ORGANISM: Homo sapiens
<220> FEATURE:
<221> NAME/KEY: CDS
<222> LOCATION: (177)..(1796)
<223> OTHER INFORMATION:

<400> SEQUENCE: 3
ggggaggcgc ggcgcgccgg ggacagcggc ggacggcggc ggcggcggca tgcggctcct    60
cgcgctgccc atcgtgggct gaggcggccg cagaaccggc gggaggcgcg gcggccgggc   120
```

-continued

| | |
|---|---|
| gagccgaggg cgcagccagc cgggcggacc gcggacagcg gtcggggcgc cgcgcc atg<br>Met<br>1 | 179 |
| ggg cga gcc ggg ggg ggg ggc ccg ggc cgg ggg ccg cca ctg ctg<br>Gly Arg Ala Gly Gly Gly Gly Pro Gly Arg Gly Pro Pro Leu Leu<br>5                               10                            15 | 227 |
| ctg ttt ctg ggg gcc gcg ctg gtc ctg gcc tct ggg gcc gtg ccg gcg<br>Leu Phe Leu Gly Ala Ala Leu Val Leu Ala Ser Gly Ala Val Pro Ala<br>20                       25                      30 | 275 |
| cgt gag gcg ggc agc gcg gtt gag gcc gaa gag ctg gtg aag ggc agc<br>Arg Glu Ala Gly Ser Ala Val Glu Ala Glu Glu Leu Val Lys Gly Ser<br>35                       40                     45 | 323 |
| ccg gcg tgg gag ccg cct gcc aac gac acg cgg gaa gaa gcc ggc cca<br>Pro Ala Trp Glu Pro Pro Ala Asn Asp Thr Arg Glu Glu Ala Gly Pro<br>50                    55                    60                    65 | 371 |
| cca gcg gct ggg gaa gat gag gcg tcg tgg acg gcg ccc ggt ggc gag<br>Pro Ala Ala Gly Glu Asp Glu Ala Ser Trp Thr Ala Pro Gly Gly Glu<br>70                    75                    80 | 419 |
| ctg gcc ggg cca gaa gag gtg ctg cag gag tcg gct gcg gtg acc ggc<br>Leu Ala Gly Pro Glu Glu Val Leu Gln Glu Ser Ala Ala Val Thr Gly<br>85                       90                     95 | 467 |
| acc gcc tgg ctg gaa gct gac agc cca ggc ctg gga gga gtg acc gca<br>Thr Ala Trp Leu Glu Ala Asp Ser Pro Gly Leu Gly Gly Val Thr Ala<br>100                       105                   110 | 515 |
| gag gcg ggc agc ggc gat gcc cag gcc ctt cca gct acg ctc cag gct<br>Glu Ala Gly Ser Gly Asp Ala Gln Ala Leu Pro Ala Thr Leu Gln Ala<br>115                     120                   125 | 563 |
| ccc cac gag gtc ctc ggg cag tca atc atg ccc cct gcc att cct gag<br>Pro His Glu Val Leu Gly Gln Ser Ile Met Pro Pro Ala Ile Pro Glu<br>130                     135                   140                   145 | 611 |
| gct aca gag gcc agc ggg cca ccc tcc ccc acc ccc ggc gac aag ctg<br>Ala Thr Glu Ala Ser Gly Pro Pro Ser Pro Thr Pro Gly Asp Lys Leu<br>150                     155                   160 | 659 |
| agc cca gct tct gaa ctc ccc aag gag agc ccc ttg gag gtt tgg ctg<br>Ser Pro Ala Ser Glu Leu Pro Lys Glu Ser Pro Leu Glu Val Trp Leu<br>165                     170                   175 | 707 |
| aac ctg ggg ggc agc aca ccc gac cct caa ggg cca gag ctg act tac<br>Asn Leu Gly Gly Ser Thr Pro Asp Pro Gln Gly Pro Glu Leu Thr Tyr<br>180                     185                   190 | 755 |
| cca ttt cag ggc acc ctg gag ccc caa ccg gca tca gat atc att gac<br>Pro Phe Gln Gly Thr Leu Glu Pro Gln Pro Ala Ser Asp Ile Ile Asp<br>195                     200                   205 | 803 |
| atc gac tac ttc gaa gga ctg gat ggt gag ggt cgt ggc gca gat ctg<br>Ile Asp Tyr Phe Glu Gly Leu Asp Gly Glu Gly Arg Gly Ala Asp Leu<br>210                     215                   220                   225 | 851 |
| ggg agc ttc cca ggg tca cca gga acc tca gag aac cac cct gat act<br>Gly Ser Phe Pro Gly Ser Pro Gly Thr Ser Glu Asn His Pro Asp Thr<br>230                     235                   240 | 899 |
| gag gga gag acc cct tcc tgg agc ctg ctt gac tta tac gat gat ttc<br>Glu Gly Glu Thr Pro Ser Trp Ser Leu Leu Asp Leu Tyr Asp Asp Phe<br>245                     250                   255 | 947 |
| acc ccc ttc gat gaa tct gat ttc tac ccc acc aca tcc ttt tat gat<br>Thr Pro Phe Asp Glu Ser Asp Phe Tyr Pro Thr Thr Ser Phe Tyr Asp<br>260                     265                   270 | 995 |
| gac ttg gat gaa gag gag gag gaa gag gag gat gac aaa gat gca gta<br>Asp Leu Asp Glu Glu Glu Glu Glu Glu Asp Asp Lys Asp Ala Val<br>275                     280                   285 | 1043 |
| gga ggt gga gac cta gaa gat gaa aat gag ctt cta gtg ccc act ggg<br>Gly Gly Gly Asp Leu Glu Asp Glu Asn Glu Leu Leu Val Pro Thr Gly<br>290                     295                   300                   305 | 1091 |

```
aag cct ggt ctg ggg ccc ggg aca ggc cag ccc acc agt cgg tgg cat    1139
Lys Pro Gly Leu Gly Pro Gly Thr Gly Gln Pro Thr Ser Arg Trp His
            310                 315                 320 gct gtc cct cca cag cac act ctg ggg tcg gtc ccc ggc agc agc atc    1187
Ala Val Pro Pro Gln His Thr Leu Gly Ser Val Pro Gly Ser Ser Ile
                325                 330                 335 gcc ctc agg ccc cgc cca gga gag cca ggc agg gac ttg gcc tcc agt    1235
Ala Leu Arg Pro Arg Pro Gly Glu Pro Gly Arg Asp Leu Ala Ser Ser
            340                 345                 350 gaa aat ggc act gag tgc cgc agt ggc ttt gtg cgg cat aac ggc tcc    1283
Glu Asn Gly Thr Glu Cys Arg Ser Gly Phe Val Arg His Asn Gly Ser
        355                 360                 365 tgc cgg tca gtg tgc gac ctc ttc cca agt tac tgt cac aat ggc ggc    1331
Cys Arg Ser Val Cys Asp Leu Phe Pro Ser Tyr Cys His Asn Gly Gly
370                 375                 380                 385 cag tgc tac ctg gtg gag aac ata ggg gcc ttc tgc agg tgc aac acg    1379
Gln Cys Tyr Leu Val Glu Asn Ile Gly Ala Phe Cys Arg Cys Asn Thr
                390                 395                 400 cag gac tac atc tgg cac aag ggg atg cgc tgc gag tcc atc atc acc    1427
Gln Asp Tyr Ile Trp His Lys Gly Met Arg Cys Glu Ser Ile Ile Thr
            405                 410                 415 gac ttc cag gtg atg tgc gtg gcc gtg ggc tcg gct gcc ctc gtc ctg    1475
Asp Phe Gln Val Met Cys Val Ala Val Gly Ser Ala Ala Leu Val Leu
        420                 425                 430 ctc ctg ctc ttc atg atg acg gtg ttc ttt gcc aag aag ctc tac ctg    1523
Leu Leu Leu Phe Met Met Thr Val Phe Phe Ala Lys Lys Leu Tyr Leu
    435                 440                 445 ctc aag acg gag aat acc aag ctg cgt agg acc aac aaa ttc cgg acc    1571
Leu Lys Thr Glu Asn Thr Lys Leu Arg Arg Thr Asn Lys Phe Arg Thr
450                 455                 460                 465 cca tct gag ctc cac aat gat aac ttc tcc ctc tcc acc att gcc gag    1619
Pro Ser Glu Leu His Asn Asp Asn Phe Ser Leu Ser Thr Ile Ala Glu
                470                 475                 480 ggc tct cac cca aat gat gat cct agt gct ccc cac aaa atc cag gag    1667
Gly Ser His Pro Asn Asp Asp Pro Ser Ala Pro His Lys Ile Gln Glu
            485                 490                 495 gtt ctc aag tcc tgc ctg aaa gag gag gag tca ttt aac atc cag aac    1715
Val Leu Lys Ser Cys Leu Lys Glu Glu Glu Ser Phe Asn Ile Gln Asn
        500                 505                 510 tcc atg tcg ccc aaa ctt gag ggt ggc aaa ggt gac cag gct gac ttg    1763
Ser Met Ser Pro Lys Leu Glu Gly Gly Lys Gly Asp Gln Ala Asp Leu
    515                 520                 525 gat gtg aac tgt ctt cag aat aat tta acc taa agcagagcaa aagagagga    1816
Asp Val Asn Cys Leu Gln Asn Asn Leu Thr
530                 535 agcgggggta gtgggtgggg ggtaggggaa gaaacattat ctcctcttgt acagagtcta    1876
tttcttgtaa ccatttgtta aactctttc tttttctgat ctcatggcat gcttttatgt    1936
attttgtaca ggaggcaaaa aaatacttaa aataagcaaa gaaactgaac agaattgcat    1996
acattgggtt gttttttctg tgctgtctgt acattgcttc tgctgctgtg atttctaaac    2056
ctgtgctgtt attcaactga ctttttttg tactttgacc cacgtttttt tgaaatacca    2116
gtaaaaaaca aagttcttga aataaaactt tttaaaagt taaaaaaaaa aaaaaaaaa    2175
```

<210> SEQ ID NO 4
<211> LENGTH: 539
<212> TYPE: PRT
<213> ORGANISM: Homo sapiens

<400> SEQUENCE: 4

```
Met Gly Arg Ala Gly Gly Gly Pro Gly Arg Gly Pro Pro Leu
1               5                   10                  15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Leu Val Lys Gly
        35                  40                  45

Ser Pro Ala Trp Glu Pro Pro Ala Asn Asp Thr Arg Glu Glu Ala Gly
    50                  55                  60

Pro Pro Ala Ala Gly Glu Asp Glu Ala Ser Trp Thr Ala Pro Gly Gly
65                  70                  75                  80

Glu Leu Ala Gly Pro Glu Val Leu Gln Glu Ser Ala Ala Val Thr
                85                  90                  95

Gly Thr Ala Trp Leu Glu Ala Asp Ser Pro Gly Leu Gly Val Thr
            100                 105                 110

Ala Glu Ala Gly Ser Gly Asp Ala Gln Ala Leu Pro Ala Thr Leu Gln
            115                 120                 125

Ala Pro His Glu Val Leu Gly Gln Ser Ile Met Pro Pro Ala Ile Pro
        130                 135                 140

Glu Ala Thr Glu Ala Ser Gly Pro Pro Ser Pro Thr Pro Gly Asp Lys
145                 150                 155                 160

Leu Ser Pro Ala Ser Glu Leu Pro Lys Glu Ser Pro Leu Glu Val Trp
                165                 170                 175

Leu Asn Leu Gly Gly Ser Thr Pro Asp Pro Gln Gly Pro Glu Leu Thr
            180                 185                 190

Tyr Pro Phe Gln Gly Thr Leu Glu Pro Gln Pro Ala Ser Asp Ile Ile
        195                 200                 205

Asp Ile Asp Tyr Phe Glu Gly Leu Asp Gly Glu Gly Arg Gly Ala Asp
    210                 215                 220

Leu Gly Ser Phe Pro Gly Ser Pro Gly Thr Ser Glu Asn His Pro Asp
225                 230                 235                 240

Thr Glu Gly Glu Thr Pro Ser Trp Ser Leu Leu Asp Leu Tyr Asp Asp
                245                 250                 255

Phe Thr Pro Phe Asp Glu Ser Asp Phe Tyr Pro Thr Thr Ser Phe Tyr
            260                 265                 270

Asp Asp Leu Asp Glu Glu Glu Glu Glu Asp Asp Lys Asp Ala
        275                 280                 285

Val Gly Gly Gly Asp Leu Glu Asp Glu Asn Glu Leu Leu Val Pro Thr
    290                 295                 300

Gly Lys Pro Gly Leu Gly Pro Gly Thr Gly Gln Pro Thr Ser Arg Trp
305                 310                 315                 320

His Ala Val Pro Pro Gln His Thr Leu Gly Ser Val Pro Gly Ser Ser
                325                 330                 335

Ile Ala Leu Arg Pro Arg Pro Gly Glu Pro Gly Arg Asp Leu Ala Ser
            340                 345                 350

Ser Glu Asn Gly Thr Glu Cys Arg Ser Gly Phe Val Arg His Asn Gly
        355                 360                 365

Ser Cys Arg Ser Val Cys Asp Leu Phe Pro Ser Tyr Cys His Asn Gly
    370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415
```

```
Thr Asp Phe Gln Val Met Cys Val Ala Val Gly Ser Ala Ala Leu Val
            420                 425                 430

Leu Leu Leu Leu Phe Met Met Thr Val Phe Phe Ala Lys Lys Leu Tyr
        435                 440                 445

Leu Leu Lys Thr Glu Asn Thr Lys Leu Arg Arg Thr Asn Lys Phe Arg
    450                 455                 460

Thr Pro Ser Glu Leu His Asn Asp Asn Phe Ser Leu Ser Thr Ile Ala
465                 470                 475                 480

Glu Gly Ser His Pro Asn Asp Asp Pro Ser Ala Pro His Lys Ile Gln
                485                 490                 495

Glu Val Leu Lys Ser Cys Leu Lys Glu Glu Ser Phe Asn Ile Gln
            500                 505                 510

Asn Ser Met Ser Pro Lys Leu Glu Gly Gly Lys Gly Asp Gln Ala Asp
        515                 520                 525

Leu Asp Val Asn Cys Leu Gln Asn Asn Leu Thr
    530                 535
```

<210> SEQ ID NO 5
<211> LENGTH: 2253
<212> TYPE: DNA
<213> ORGANISM: Homo sapiens
<220> FEATURE:
<221> NAME/KEY: CDS
<222> LOCATION: (669)..(1874)
<223> OTHER INFORMATION:

<400> SEQUENCE: 5

```
agtccagtga ggaataactg tagataagat gagatgatgg gcattaagtg taactgctga      60
gaagccttca tagagggaaa ggtgataaga actgagtttt tctggcatga ggagtttacc     120
aggcaggaga ggtggagacg ctaggctagg caaataggct gcagccatag ttctgctgag     180
aaacaggttt tgaaccaagg caactccatc tggagatatg tatcagaaag attaggagat     240
agaatctcca tcttggtcac ttatttggtc ttctaagaca gcaatgggac cgtctcttaa     300
atactggagt tgtcctatct ccttgggctg ataccctgaa ctgtcatttg gcgcgtgagg     360
cgggcagcgc ggttgaggcc gaagagctgg tgaagggcag cccggcgtgg gagccgcctg     420
ccaacgacac gcgggaagaa gccggcccac cagcggctgg ggaagatgag gcgtcgtgga     480
cggcgcccgg tggcgagctg gccgggccag aagaggtgct gcaggagtcg gctgcggtga     540
ccggcaccgc ctggctggaa gctgacagcc caggcctggg aggagtgacc gcagaggcgg     600
gcagcggcga tgcccaggcc cttccagcta cgctccaggc tccccacgag gtcctcgggc     660 agtcaatc atg ccc cct gcc att cct gag gct aca gag gcc agc ggg cca     710
         Met Pro Pro Ala Ile Pro Glu Ala Thr Glu Ala Ser Gly Pro
           1               5                  10 ccc tcc ccc acc ccc ggc gac aag ctg agc cca gct tct gaa ctc ccc     758
Pro Ser Pro Thr Pro Gly Asp Lys Leu Ser Pro Ala Ser Glu Leu Pro
 15              20                  25                  30 aag gag agc ccc ttg gag gtt tgg ctg aac ctg ggg ggc agc aca ccc     806
Lys Glu Ser Pro Leu Glu Val Trp Leu Asn Leu Gly Gly Ser Thr Pro
             35                  40                  45 gac cct caa ggg cca gag ctg act tac cca ttt cag ggc acc ctg gag     854
Asp Pro Gln Gly Pro Glu Leu Thr Tyr Pro Phe Gln Gly Thr Leu Glu
         50                  55                  60 ccc caa ccg gca tca gat atc att gac atc gac tac ttc gaa gga ctg     902
Pro Gln Pro Ala Ser Asp Ile Ile Asp Ile Asp Tyr Phe Glu Gly Leu
     65                  70                  75
```

```
gat ggt gag ggt cgt ggc gca gat ctg ggg agc ttc cca ggg tca cca        950
Asp Gly Glu Gly Arg Gly Ala Asp Leu Gly Ser Phe Pro Gly Ser Pro
 80              85                  90 gga acc tca gag aac cac cct gat act gag gga gag acc cct tcc tgg        998
Gly Thr Ser Glu Asn His Pro Asp Thr Glu Gly Glu Thr Pro Ser Trp
 95                     100                 105                 110 agc ctg ctt gac tta tac gat gat ttc acc ccc ttc gat gaa tct gat       1046
Ser Leu Leu Asp Leu Tyr Asp Asp Phe Thr Pro Phe Asp Glu Ser Asp
                    115                 120                 125 ttc tac ccc acc aca tcc ttt tat gat gac ttg gat gaa gag gag gag       1094
Phe Tyr Pro Thr Thr Ser Phe Tyr Asp Asp Leu Asp Glu Glu Glu Glu
            130                 135                 140 gaa gag gag gat gac aaa gat gca gta gga ggt gga gac cta gaa gat       1142
Glu Glu Glu Asp Asp Lys Asp Ala Val Gly Gly Gly Asp Leu Glu Asp
        145                 150                 155 gaa aat gag ctt cta gtg ccc act ggg aag cct ggt ctg ggg ccc ggg       1190
Glu Asn Glu Leu Leu Val Pro Thr Gly Lys Pro Gly Leu Gly Pro Gly
160                 165                 170 aca ggc cag ccc acc agt cgg tgg cat gct gtc cct cca cag cac act       1238
Thr Gly Gln Pro Thr Ser Arg Trp His Ala Val Pro Pro Gln His Thr
175                 180                 185                 190 ctg ggg tcg gtc ccc ggc agc agc atc gcc ctc agg ccc cgc cca gga       1286
Leu Gly Ser Val Pro Gly Ser Ser Ile Ala Leu Arg Pro Arg Pro Gly
                    195                 200                 205 gag cca ggc agg gac ttg gcc tcc agt gaa aat ggc act gag tgc cgc       1334
Glu Pro Gly Arg Asp Leu Ala Ser Ser Glu Asn Gly Thr Glu Cys Arg
                210                 215                 220 agt ggc ttt gtg cgg cat aac ggc tcc tgc cgg tca gtg tgc gac ctc       1382
Ser Gly Phe Val Arg His Asn Gly Ser Cys Arg Ser Val Cys Asp Leu
            225                 230                 235 ttc cca agt tac tgt cac aat ggc ggc cag tgc tac ctg gtg gag aac       1430
Phe Pro Ser Tyr Cys His Asn Gly Gly Gln Cys Tyr Leu Val Glu Asn
        240                 245                 250 ata ggg gcc ttc tgc agg tgc aac acg cag gac tac atc tgg cac aag       1478
Ile Gly Ala Phe Cys Arg Cys Asn Thr Gln Asp Tyr Ile Trp His Lys
255                 260                 265                 270 ggg atg cgc tgc gag tcc atc atc acc gac ttc cag gtg atg tgc gtg       1526
Gly Met Arg Cys Glu Ser Ile Ile Thr Asp Phe Gln Val Met Cys Val
                    275                 280                 285 gcc gtg ggc tcg gct gcc ctc gtc ctg ctc ctg ttc atg atg acg       1574
Ala Val Gly Ser Ala Ala Leu Val Leu Leu Leu Phe Met Met Thr
                290                 295                 300 gtg ttc ttt gcc aag aag ctc tac ctg ctc aag acg gag aat acc aag       1622
Val Phe Phe Ala Lys Lys Leu Tyr Leu Leu Lys Thr Glu Asn Thr Lys
            305                 310                 315 ctg cgt agg acc aac aaa ttc cgg acc cca tct gag ctc cac aat gat       1670
Leu Arg Arg Thr Asn Lys Phe Arg Thr Pro Ser Glu Leu His Asn Asp
        320                 325                 330 aac ttc tcc ctc tcc acc att gcc gag ggc tct cac cca aat gat gat       1718
Asn Phe Ser Leu Ser Thr Ile Ala Glu Gly Ser His Pro Asn Asp Asp
335                 340                 345                 350 cct agt gct ccc cac aaa atc cag gag gtt ctc aag tcc tgc ctg aaa       1766
Pro Ser Ala Pro His Lys Ile Gln Glu Val Leu Lys Ser Cys Leu Lys
                    355                 360                 365 gag gag gag tca ttt aac atc cag aac tcc atg tcg ccc aaa ctt gag       1814
Glu Glu Glu Ser Phe Asn Ile Gln Asn Ser Met Ser Pro Lys Leu Glu
                370                 375                 380 ggt ggc aaa ggt gac cag gct gac ttg gat gtg aac tgt ctt cag aat       1862
Gly Gly Lys Gly Asp Gln Ala Asp Leu Asp Val Asn Cys Leu Gln Asn
            385                 390                 395
```

-continued

```
aat tta acc taa agcagagcaa gaagagagga agcgggggta gtgggtgggg    1914
Asn Leu Thr
    400 ggtaggggaa gaaacattat ctcctcttgt acagagtcta tttcttgtaa ccatttgtta    1974 aactctttc tttttctgat ctcatggcat gcttttatgt attttgtaca ggaggcaaaa    2034 aaatacttaa aataagcaaa gaaactgaac agaattgcat acattgggtt gttttttctg    2094 tgctgtctgt acattgcttc tgctgctgtg atttctaaac ctgtgctgtt attcaactga    2154 ctttttttg tactttgacc cacgtttttt tgaaatacca gtaaaaaaca aagttcttga    2214 aataaaactt tttaaaaagt taaaaaaaaa aaaaaaaa    2253

<210> SEQ ID NO 6
<211> LENGTH: 401
<212> TYPE: PRT
<213> ORGANISM: Homo sapiens

<400> SEQUENCE: 6

Met Pro Pro Ala Ile Pro Glu Ala Thr Glu Ala Ser Gly Pro Pro Ser
1               5                   10                  15

Pro Thr Pro Gly Asp Lys Leu Ser Pro Ala Ser Glu Leu Pro Lys Glu
            20                  25                  30

Ser Pro Leu Glu Val Trp Leu Asn Leu Gly Gly Ser Thr Pro Asp Pro
        35                  40                  45

Gln Gly Pro Glu Leu Thr Tyr Pro Phe Gln Gly Thr Leu Glu Pro Gln
    50                  55                  60

Pro Ala Ser Asp Ile Asp Ile Asp Tyr Phe Glu Gly Leu Asp Gly
65                  70                  75                  80

Glu Gly Arg Gly Ala Asp Leu Gly Ser Phe Pro Gly Ser Pro Gly Thr
                85                  90                  95

Ser Glu Asn His Pro Asp Thr Glu Gly Glu Thr Pro Ser Trp Ser Leu
            100                 105                 110

Leu Asp Leu Tyr Asp Asp Phe Thr Pro Phe Asp Glu Ser Asp Phe Tyr
        115                 120                 125

Pro Thr Thr Ser Phe Tyr Asp Asp Leu Asp Glu Glu Glu Glu Glu
    130                 135                 140

Glu Asp Asp Lys Asp Ala Val Gly Gly Gly Asp Leu Glu Asp Glu Asn
145                 150                 155                 160

Glu Leu Leu Val Pro Thr Gly Lys Pro Gly Leu Gly Pro Gly Thr Gly
                165                 170                 175

Gln Pro Thr Ser Arg Trp His Ala Val Pro Pro Gln His Thr Leu Gly
            180                 185                 190

Ser Val Pro Gly Ser Ser Ile Ala Leu Arg Pro Arg Pro Gly Glu Pro
        195                 200                 205

Gly Arg Asp Leu Ala Ser Ser Glu Asn Gly Thr Glu Cys Arg Ser Gly
    210                 215                 220

Phe Val Arg His Asn Gly Ser Cys Arg Ser Val Cys Asp Leu Phe Pro
225                 230                 235                 240

Ser Tyr Cys His Asn Gly Gly Gln Cys Tyr Leu Val Glu Asn Ile Gly
                245                 250                 255

Ala Phe Cys Arg Cys Asn Thr Gln Asp Tyr Ile Trp His Lys Gly Met
            260                 265                 270

Arg Cys Glu Ser Ile Ile Thr Asp Phe Gln Val Met Cys Val Ala Val
        275                 280                 285
```

```
Gly Ser Ala Ala Leu Val Leu Leu Leu Phe Met Met Thr Val Phe
    290             295                 300
Phe Ala Lys Lys Leu Tyr Leu Leu Lys Thr Glu Asn Thr Lys Leu Arg
305             310                 315                 320
Arg Thr Asn Lys Phe Arg Thr Pro Ser Glu Leu His Asn Asp Asn Phe
                325                 330                 335
Ser Leu Ser Thr Ile Ala Glu Gly Ser His Pro Asn Asp Asp Pro Ser
            340                 345                 350
Ala Pro His Lys Ile Gln Glu Val Leu Lys Ser Cys Leu Lys Glu Glu
        355                 360                 365
Glu Ser Phe Asn Ile Gln Asn Ser Met Ser Pro Lys Leu Glu Gly Gly
370                 375                 380
Lys Gly Asp Gln Ala Asp Leu Asp Val Asn Cys Leu Gln Asn Asn Leu
385                 390                 395                 400
Thr

<210> SEQ ID NO 7
<211> LENGTH: 2256
<212> TYPE: DNA
<213> ORGANISM: Homo sapiens
<220> FEATURE:
<221> NAME/KEY: CDS
<222> LOCATION: (177)..(1877)
<223> OTHER INFORMATION:

<400> SEQUENCE: 7
ggggaggcgc ggcgcgccgg ggacagcggc ggacggcggc ggcggcggca tgcggctcct     60
cgcgctgccc atcgtgggct gaggcggccg cagaaccggc gggaggcgcg gcggccgggc    120
gagccgaggg cgcagccagc cgggcggacc gcggacagcg gtcggggcgc gcgcc atg    179
                                                             Met
                                                              1 ggg cga gcc ggg ggc ggg ggc ccg ggc cgg ggg ccg cca ctg ctg           227
Gly Arg Ala Gly Gly Gly Gly Pro Gly Arg Gly Pro Pro Leu Leu
          5                  10                  15 ctg ttt ctg ggg gcc gcg ctg gtc ctg gcc tct ggg gcc gtg ccg gcg     275
Leu Phe Leu Gly Ala Ala Leu Val Leu Ala Ser Gly Ala Val Pro Ala
         20                  25                  30 cgt gag gcg ggc agc gcg gtt gag gcc gaa gag ctg gtg aag ggc agc     323
Arg Glu Ala Gly Ser Ala Val Glu Ala Glu Glu Leu Val Lys Gly Ser
 35                  40                  45 ccg gcg tgg gag ccg cct gcc aac gac acg cgg gaa gaa gcc ggc cca     371
Pro Ala Trp Glu Pro Pro Ala Asn Asp Thr Arg Glu Glu Ala Gly Pro
 50                  55                  60                  65 cca gcg gct ggg gaa gat gag gcg tcg tgg acg gcg ccc ggt ggc gag     419
Pro Ala Ala Gly Glu Asp Glu Ala Ser Trp Thr Ala Pro Gly Gly Glu
             70                  75                  80 ctg gcc ggg cca gaa gag gtg ctg cag gag tcg gct gcg gtg acc ggc     467
Leu Ala Gly Pro Glu Glu Val Leu Gln Glu Ser Ala Ala Val Thr Gly
         85                  90                  95 acc gcc tgg ctg gaa gct gac agc cca ggc ctg gga gga gtg acc gca     515
Thr Ala Trp Leu Glu Ala Asp Ser Pro Gly Leu Gly Gly Val Thr Ala
     100                 105                 110 gag gcg ggc agc ggc gat gcc cag gcc ctt cca gct acg ctc cag gct     563
Glu Ala Gly Ser Gly Asp Ala Gln Ala Leu Pro Ala Thr Leu Gln Ala
 115                 120                 125 ccc cac gag gtc ctc ggg cag tca atc atg ccc cct gcc att cct gag    611
Pro His Glu Val Leu Gly Gln Ser Ile Met Pro Pro Ala Ile Pro Glu
130                 135                 140                 145
```

```
gct aca gag gcc agc ggg cca ccc tcc ccc acc ccc ggc gac aag ctg      659
Ala Thr Glu Ala Ser Gly Pro Pro Ser Pro Thr Pro Gly Asp Lys Leu
            150                 155                 160 agc cca gct tct gaa ctc ccc aag gag agc ccc ttg gag gtt tgg ctg      707
Ser Pro Ala Ser Glu Leu Pro Lys Glu Ser Pro Leu Glu Val Trp Leu
            165                 170                 175 aac ctg ggg ggc agc aca ccc gac cct caa ggg cca gag ctg act tac      755
Asn Leu Gly Gly Ser Thr Pro Asp Pro Gln Gly Pro Glu Leu Thr Tyr
            180                 185                 190 cca ttt cag ggc acc ctg gag ccc caa ccg gca tca gat atc att gac      803
Pro Phe Gln Gly Thr Leu Glu Pro Gln Pro Ala Ser Asp Ile Ile Asp
        195                 200                 205 atc gac tac ttc gaa gga ctg gat ggt gag ggt cgt ggc gca gat ctg      851
Ile Asp Tyr Phe Glu Gly Leu Asp Gly Glu Gly Arg Gly Ala Asp Leu
210                 215                 220                 225 ggg agc ttc cca ggg tca cca gga acc tca gag aac cac cct gat act      899
Gly Ser Phe Pro Gly Ser Pro Gly Thr Ser Glu Asn His Pro Asp Thr
                    230                 235                 240 gag gga gag acc cct tcc tgg agc ctg ctt gac tta tac gat gat ttc      947
Glu Gly Glu Thr Pro Ser Trp Ser Leu Leu Asp Leu Tyr Asp Asp Phe
                245                 250                 255 acc ccc ttc gat gaa tct gat ttc tac ccc acc aca tcc ttt tat gat      995
Thr Pro Phe Asp Glu Ser Asp Phe Tyr Pro Thr Thr Ser Phe Tyr Asp
            260                 265                 270 gac ttg gat gaa gag gag gag gaa gag gag gat gac aaa gat gca gta     1043
Asp Leu Asp Glu Glu Glu Glu Glu Glu Asp Asp Lys Asp Ala Val
            275                 280                 285 gga ggt gga gac cta gaa gat gaa aat gag ctt cta gtg ccc act ggg     1091
Gly Gly Gly Asp Leu Glu Asp Glu Asn Glu Leu Leu Val Pro Thr Gly
290                 295                 300                 305 aag cct ggt ctg ggg ccc ggg aca ggc cag ccc acc agt cgg tgg cat     1139
Lys Pro Gly Leu Gly Pro Gly Thr Gly Gln Pro Thr Ser Arg Trp His
                310                 315                 320 gct gtc cct cca cag cac act ctg ggg tcg gtc ccc ggc agc agc atc     1187
Ala Val Pro Pro Gln His Thr Leu Gly Ser Val Pro Gly Ser Ser Ile
            325                 330                 335 gcc ctc agg ccc cgc cca gga gag cca ggc agg gac ttg gcc tcc agt     1235
Ala Leu Arg Pro Arg Pro Gly Glu Pro Gly Arg Asp Leu Ala Ser Ser
            340                 345                 350 gaa aat ggc act gag tgc cgc agt ggc ttt gtg cgg cat aac ggc tcc     1283
Glu Asn Gly Thr Glu Cys Arg Ser Gly Phe Val Arg His Asn Gly Ser
            355                 360                 365 tgc cgg tca gtg tgc gac ctc ttc cca agt tac tgt cac aat ggc ggc     1331
Cys Arg Ser Val Cys Asp Leu Phe Pro Ser Tyr Cys His Asn Gly Gly
370                 375                 380                 385 cag tgc tac ctg gtg gag aac ata ggg gcc ttc tgc agg tgc aac acg     1379
Gln Cys Tyr Leu Val Glu Asn Ile Gly Ala Phe Cys Arg Cys Asn Thr
                390                 395                 400 cag gac tac atc tgg cac aag ggg atg cgc tgc gag tcc atc atc acc     1427
Gln Asp Tyr Ile Trp His Lys Gly Met Arg Cys Glu Ser Ile Ile Thr
            405                 410                 415 gac ttc cag gtg atg tgc gtg gcc gtg ggc tcg gct gcc ctc gtc ctg     1475
Asp Phe Gln Val Met Cys Val Ala Val Gly Ser Ala Ala Leu Val Leu
            420                 425                 430 ctc ctg ctc ttc atg atg acg gtg ttc ttt gcc aag aag ctc tac ctg     1523
Leu Leu Leu Phe Met Met Thr Val Phe Phe Ala Lys Lys Leu Tyr Leu
        435                 440                 445 ctc aag acg gag aat acc aag ctg cgt agg acc aac aaa ttc cgg acc     1571
Leu Lys Thr Glu Asn Thr Lys Leu Arg Arg Thr Asn Lys Phe Arg Thr
450                 455                 460                 465
```

-continued

```
cca tct gag ctc cac aat gat aac ttc tcc ctc tcc acc att gcc gag     1619
Pro Ser Glu Leu His Asn Asp Asn Phe Ser Leu Ser Thr Ile Ala Glu
            470                 475                 480 ggc tct cac cca aat gta agg aaa ctt tgc aac act ccc cgt acc tcc     1667
Gly Ser His Pro Asn Val Arg Lys Leu Cys Asn Thr Pro Arg Thr Ser
        485                 490                 495 tcc ccc cat gcc cgt gcc ttg gct cac tat gat aac gtt atc tgt cag     1715
Ser Pro His Ala Arg Ala Leu Ala His Tyr Asp Asn Val Ile Cys Gln
    500                 505                 510 gat gat cct agt gct ccc cac aaa atc cag gag gtt ctc aag tcc tgc     1763
Asp Asp Pro Ser Ala Pro His Lys Ile Gln Glu Val Leu Lys Ser Cys
515                 520                 525 ctg aaa gag gag gag tca ttt aac atc cag aac tcc atg tcg ccc aaa     1811
Leu Lys Glu Glu Glu Ser Phe Asn Ile Gln Asn Ser Met Ser Pro Lys
530                 535                 540                 545 ctt gag ggt ggc aaa ggt gac cag gct gac ttg gat gtg aac tgt ctt     1859
Leu Glu Gly Gly Lys Gly Asp Gln Ala Asp Leu Asp Val Asn Cys Leu
                550                 555                 560 cag aat aat tta acc taa agcagagcaa gaagagagga agcggggta             1907
Gln Asn Asn Leu Thr
                565 gtgggtgggg ggtaggggaa gaaacattat ctcctcttgt acagagtcta tttcttgtaa   1967 ccatttgtta aactcttttc ttttttctgat ctcatggcat gcttttatgt attttgtaca  2027 ggaggcaaaa aaatacttaa aataagcaaa gaaactgaac agaattgcat acattgggtt   2087 gtttttttctg tgctgtctgt acattgcttc tgctgctgtg atttctaaac ctgtgctgtt  2147 attcaactga cttttttttg tactttgacc cacgtttttt tgaaatacca gtaaaaaaca   2207 aagttcttga aataaaactt tttaaaaagt taaaaaaaaa aaaaaaaa                2256
```

<210> SEQ ID NO 8
<211> LENGTH: 566
<212> TYPE: PRT
<213> ORGANISM: Homo sapiens

<400> SEQUENCE: 8

```
Met Gly Arg Ala Gly Gly Gly Pro Gly Arg Gly Pro Pro Leu
1               5                   10                  15

Leu Leu Phe Leu Gly Ala Ala Leu Val Leu Ala Ser Gly Ala Val Pro
                20                  25                  30

Ala Arg Glu Ala Gly Ser Ala Val Glu Ala Glu Leu Val Lys Gly
            35                  40                  45

Ser Pro Ala Trp Glu Pro Ala Asn Asp Thr Arg Glu Glu Ala Gly
        50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
                85                  90                  95

Gly Thr Ala Trp Leu Glu Ala Asp Ser Pro Gly Leu Gly Gly Val Thr
            100                 105                 110

Ala Glu Ala Gly Ser Gly Asp Ala Gln Ala Leu Pro Ala Thr Leu Gln
        115                 120                 125

Ala Pro His Glu Val Leu Gly Gln Ser Ile Met Pro Pro Ala Ile Pro
    130                 135                 140

Glu Ala Thr Glu Ala Ser Gly Pro Pro Ser Pro Thr Pro Gly Asp Lys
145                 150                 155                 160
```

```
Leu Ser Pro Ala Ser Glu Leu Pro Lys Glu Ser Pro Leu Glu Val Trp
                165                 170                 175
Leu Asn Leu Gly Gly Ser Thr Pro Asp Pro Gln Gly Pro Glu Leu Thr
            180                 185                 190
Tyr Pro Phe Gln Gly Thr Leu Glu Pro Gln Pro Ala Ser Asp Ile Ile
        195                 200                 205
Asp Ile Asp Tyr Phe Glu Gly Leu Asp Gly Glu Gly Arg Gly Ala Asp
    210                 215                 220
Leu Gly Ser Phe Pro Gly Ser Pro Gly Thr Ser Glu Asn His Pro Asp
225                 230                 235                 240
Thr Glu Gly Glu Thr Pro Ser Trp Ser Leu Leu Asp Leu Tyr Asp Asp
                245                 250                 255
Phe Thr Pro Phe Asp Glu Ser Asp Phe Tyr Pro Thr Thr Ser Phe Tyr
            260                 265                 270
Asp Asp Leu Asp Glu Glu Glu Glu Glu Glu Asp Asp Lys Asp Ala
        275                 280                 285
Val Gly Gly Gly Asp Leu Glu Asp Glu Asn Glu Leu Leu Val Pro Thr
    290                 295                 300
Gly Lys Pro Gly Leu Gly Pro Gly Thr Gly Gln Pro Thr Ser Arg Trp
305                 310                 315                 320
His Ala Val Pro Pro Gln His Thr Leu Gly Ser Val Pro Gly Ser Ser
                325                 330                 335
Ile Ala Leu Arg Pro Arg Pro Gly Glu Pro Gly Arg Asp Leu Ala Ser
            340                 345                 350
Ser Glu Asn Gly Thr Glu Cys Arg Ser Gly Phe Val Arg His Asn Gly
        355                 360                 365
Ser Cys Arg Ser Val Cys Asp Leu Phe Pro Ser Tyr Cys His Asn Gly
    370                 375                 380
Gly Gln Cys Tyr Leu Val Glu Asn Ile Gly Ala Phe Cys Arg Cys Asn
385                 390                 395                 400
Thr Gln Asp Tyr Ile Trp His Lys Gly Met Arg Cys Glu Ser Ile Ile
                405                 410                 415
Thr Asp Phe Gln Val Met Cys Val Ala Val Gly Ser Ala Ala Leu Val
            420                 425                 430
Leu Leu Leu Leu Phe Met Met Thr Val Phe Phe Ala Lys Lys Leu Tyr
        435                 440                 445
Leu Leu Lys Thr Glu Asn Thr Lys Leu Arg Arg Thr Asn Lys Phe Arg
    450                 455                 460
Thr Pro Ser Glu Leu His Asn Asp Asn Phe Ser Leu Ser Thr Ile Ala
465                 470                 475                 480
Glu Gly Ser His Pro Asn Val Arg Lys Leu Cys Asn Thr Pro Arg Thr
                485                 490                 495
Ser Ser Pro His Ala Arg Ala Leu Ala His Tyr Asp Asn Val Ile Cys
            500                 505                 510
Gln Asp Asp Pro Ser Ala Pro His Lys Ile Gln Glu Val Leu Lys Ser
        515                 520                 525
Cys Leu Lys Glu Glu Glu Ser Phe Asn Ile Gln Asn Ser Met Ser Pro
    530                 535                 540
Lys Leu Glu Gly Gly Lys Gly Asp Gln Ala Asp Leu Asp Val Asn Cys
545                 550                 555                 560
Leu Gln Asn Asn Leu Thr
                565
```

```
<210> SEQ ID NO 9
<211> LENGTH: 2099
<212> TYPE: DNA
<213> ORGANISM: Homo sapiens
<220> FEATURE:
<221> NAME/KEY: CDS
<222> LOCATION: (177)..(1610)
<223> OTHER INFORMATION:

<400> SEQUENCE: 9
ggggaggcgc ggcgcgccgg ggacagcggc ggacggcggc ggcggcggca tgcggctcct      60
cgcgctgccc atcgtgggct gaggcggccg cagaaccggc gggaggcgcg gcggccgggc     120
gagccgaggg cgcagccagc cgggcggacc gcggacagcg gtcggggcgc cgcgcc atg    179
                                                            Met
                                                             1 ggg cga gcc ggg ggc ggg ggc ccg ggc cgg ggg ccg ccg cca ctg ctg      227
Gly Arg Ala Gly Gly Gly Gly Pro Gly Arg Gly Pro Pro Pro Leu Leu
            5                   10                  15 ctg ttt ctg ggg gcc gcg ctg gtc ctg gcc tct ggg gcc gtg ccg gcg      275
Leu Phe Leu Gly Ala Ala Leu Val Leu Ala Ser Gly Ala Val Pro Ala
        20                  25                  30 cgt gag gcg ggc agc gcg gtt gag gcc gaa gag ctg gtg aag ggc agc      323
Arg Glu Ala Gly Ser Ala Val Glu Ala Glu Glu Leu Val Lys Gly Ser
 35                  40                  45 ccg gcg tgg gag ccg cct gcc aac gac acg cgg gaa gaa gcc ggc cca      371
Pro Ala Trp Glu Pro Pro Ala Asn Asp Thr Arg Glu Glu Ala Gly Pro
 50                  55                  60                  65 cca gcg gct ggg gaa gat gag gcg tcg tgg acg gcg ccc ggt ggc gag      419
Pro Ala Ala Gly Glu Asp Glu Ala Ser Trp Thr Ala Pro Gly Gly Glu
                 70                  75                  80 ctg gcc ggg cca gaa gag gtg ctg cag gag tcg gct gcg gtg acc ggc      467
Leu Ala Gly Pro Glu Glu Val Leu Gln Glu Ser Ala Ala Val Thr Gly
             85                  90                  95 acc gcc tgg ctg gaa gct gac agc cca ggc ctg gga gga gtg acc gca      515
Thr Ala Trp Leu Glu Ala Asp Ser Pro Gly Leu Gly Gly Val Thr Ala
        100                 105                 110 gag gcg ggc agc ggc gat gcc cag gcc ctt cca gct acg ctc cag gct      563
Glu Ala Gly Ser Gly Asp Ala Gln Ala Leu Pro Ala Thr Leu Gln Ala
    115                 120                 125 ccc cac gag gtc ctc ggg cag tca atc atg ccc cct gcc att cct gag      611
Pro His Glu Val Leu Gly Gln Ser Ile Met Pro Pro Ala Ile Pro Glu
130                 135                 140                 145 gct aca gag gcc agc ggg cca ccc tcc ccc acc ccc ggc gac aag ctg      659
Ala Thr Glu Ala Ser Gly Pro Pro Ser Pro Thr Pro Gly Asp Lys Leu
                150                 155                 160 agc cca gct tct gaa ctc ccc aag gag agc ccc ttg gag gtt tgg ctg      707
Ser Pro Ala Ser Glu Leu Pro Lys Glu Ser Pro Leu Glu Val Trp Leu
            165                 170                 175 aac ctg ggg ggc agc aca ccc gac cct caa ggg cca gag ctg act tac      755
Asn Leu Gly Gly Ser Thr Pro Asp Pro Gln Gly Pro Glu Leu Thr Tyr
        180                 185                 190 cca ttt cag ggc acc ctg gag ccc caa ccg gca tca gat atc att gac      803
Pro Phe Gln Gly Thr Leu Glu Pro Gln Pro Ala Ser Asp Ile Ile Asp
    195                 200                 205 atc gac tac ttc gaa gga ctg gat ggt gag ggt cgt ggc gca gat ctg      851
Ile Asp Tyr Phe Glu Gly Leu Asp Gly Glu Gly Arg Gly Ala Asp Leu
210                 215                 220                 225 ggg agc ttc cca ggg tca cca gga acc tca gag aac cac cct gat act      899
Gly Ser Phe Pro Gly Ser Pro Gly Thr Ser Glu Asn His Pro Asp Thr
                230                 235                 240
```

```
gag gga gag acc cct tcc tgg agc ctg ctt gac tta tac gat gat ttc      947
Glu Gly Glu Thr Pro Ser Trp Ser Leu Leu Asp Leu Tyr Asp Asp Phe
            245                 250                 255 acc ccc ttc gat gaa tct gat ttc tac ccc acc aca tcc ttt tat gat      995
Thr Pro Phe Asp Glu Ser Asp Phe Tyr Pro Thr Thr Ser Phe Tyr Asp
        260                 265                 270 gac ttg gat gaa gag gag gag gaa gag gag gat gac aaa gat gca gta     1043
Asp Leu Asp Glu Glu Glu Glu Glu Glu Glu Asp Asp Lys Asp Ala Val
275                 280                 285 gga ggt gga gac cta gaa gat gaa aat gag ctt cta gtg ccc act ggg     1091
Gly Gly Gly Asp Leu Glu Asp Glu Asn Glu Leu Leu Val Pro Thr Gly
290                 295                 300                 305 aag cct ggt ctg ggg ccc ggg aca ggc cag ccc acc agt cgg tgg cat     1139
Lys Pro Gly Leu Gly Pro Gly Thr Gly Gln Pro Thr Ser Arg Trp His
                310                 315                 320 gct gtc cct cca cag cac act ctg ggg tcg gtc ccc ggc agc agc atc     1187
Ala Val Pro Pro Gln His Thr Leu Gly Ser Val Pro Gly Ser Ser Ile
            325                 330                 335 gcc ctc agg ccc cgc cca gga gag cca ggc agg gac ttg gcc tcc agt     1235
Ala Leu Arg Pro Arg Pro Gly Glu Pro Gly Arg Asp Leu Ala Ser Ser
        340                 345                 350 gaa aat ggc act gag tgc cgc agt ggc ttt gtg cgg cat aac ggc tcc     1283
Glu Asn Gly Thr Glu Cys Arg Ser Gly Phe Val Arg His Asn Gly Ser
355                 360                 365 tgc cgg tca gtg tgc gac ctc ttc cca agt tac tgt cac aat ggc ggc     1331
Cys Arg Ser Val Cys Asp Leu Phe Pro Ser Tyr Cys His Asn Gly Gly
370                 375                 380                 385 cag tgc tac ctg gtg gag aac ata ggg gcc ttc tgc agg tgc aac acg     1379
Gln Cys Tyr Leu Val Glu Asn Ile Gly Ala Phe Cys Arg Cys Asn Thr
                390                 395                 400 cag gac tac atc tgg cac aag ggg atg cgc tgc gag tcc atc atc acc     1427
Gln Asp Tyr Ile Trp His Lys Gly Met Arg Cys Glu Ser Ile Ile Thr
            405                 410                 415 gac ttc cag gtg atg tgc gtg gcc gtg ggc tcg gct gcc ctc gtc ctg     1475
Asp Phe Gln Val Met Cys Val Ala Val Gly Ser Ala Ala Leu Val Leu
        420                 425                 430 ctc ctg ctc ttc atg atg acg gtg ttc ttt gcc aag aag ctc tac ctg     1523
Leu Leu Leu Phe Met Met Thr Val Phe Phe Ala Lys Lys Leu Tyr Leu
435                 440                 445 ctc aag acg gag aat acc aag ctg cgt agg acc aag atg atc cta gtg     1571
Leu Lys Thr Glu Asn Thr Lys Leu Arg Arg Thr Lys Met Ile Leu Val
450                 455                 460                 465 ctc ccc aca aaa tcc agg agg ttc tca agt cct gcc tga aagaggagga     1620
Leu Pro Thr Lys Ser Arg Arg Phe Ser Ser Pro Ala
                470                 475 gtcatttaac atccagaact ccatgtcgcc caaacttgag ggtggcaaag gtgaccaggc   1680
tgacttggat gtgaactgtc ttcagaataa tttaacctaa agcagagcaa gaagagagga   1740
agcgggggta gtgggtgggg ggtaggggaa gaaacattat ctcctcttgt acagagtcta   1800
tttcttgtaa ccatttgtta aactcttttc tttttctgat ctcatggcat gcttttatgt   1860
attttgtaca ggaggcaaaa aaatacttaa aataagcaaa gaaactgaac agaattgcat   1920
acattgggtt gttttttctg tgctgtctgt acattgcttc tgctgctgtg atttctaaac   1980
ctgtgctgtt attcaactga cttttttttg tactttgacc cacgtttttt tgaaatacca   2040
gtaaaaaaca aagttcttga aataaaactt tttaaaagt taaaaaaaaa aaaaaaaaa     2099

<210> SEQ ID NO 10
<211> LENGTH: 477
```

<212> TYPE: PRT
<213> ORGANISM: Homo sapiens

<400> SEQUENCE: 10

```
Met Gly Arg Ala Gly Gly Gly Pro Gly Arg Pro Pro Leu
1               5                   10              15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Leu Val Lys Gly
        35                  40                  45

Ser Pro Ala Trp Glu Pro Pro Ala Asn Asp Thr Arg Glu Glu Ala Gly
50              55                  60

Pro Pro Ala Ala Gly Glu Asp Glu Ala Ser Trp Thr Ala Pro Gly Gly
65              70                  75                  80

Glu Leu Ala Gly Pro Glu Glu Val Leu Gln Ser Ala Ala Val Thr
            85                  90                  95

Gly Thr Ala Trp Leu Glu Ala Asp Ser Pro Gly Leu Gly Val Thr
            100                 105                 110

Ala Glu Ala Gly Ser Gly Asp Ala Gln Ala Leu Pro Ala Thr Leu Gln
            115                 120                 125

Ala Pro His Glu Val Leu Gly Gln Ser Ile Met Pro Pro Ala Ile Pro
            130                 135                 140

Glu Ala Thr Glu Ala Ser Gly Pro Pro Ser Pro Thr Pro Gly Asp Lys
145             150                 155                 160

Leu Ser Pro Ala Ser Glu Leu Pro Lys Glu Ser Pro Leu Glu Val Trp
            165                 170                 175

Leu Asn Leu Gly Gly Ser Thr Pro Asp Pro Gln Gly Pro Glu Leu Thr
            180                 185                 190

Tyr Pro Phe Gln Gly Thr Leu Glu Pro Gln Pro Ala Ser Asp Ile Ile
            195                 200                 205

Asp Ile Asp Tyr Phe Glu Gly Leu Asp Gly Glu Gly Arg Gly Ala Asp
            210                 215                 220

Leu Gly Ser Phe Pro Gly Ser Pro Gly Thr Ser Glu Asn His Pro Asp
225             230                 235                 240

Thr Glu Gly Glu Thr Pro Ser Trp Ser Leu Leu Asp Leu Tyr Asp Asp
                245                 250                 255

Phe Thr Pro Phe Asp Glu Ser Asp Phe Tyr Pro Thr Thr Ser Phe Tyr
            260                 265                 270

Asp Asp Leu Asp Glu Glu Glu Glu Glu Asp Lys Asp Ala
            275                 280                 285

Val Gly Gly Gly Asp Leu Glu Asp Glu Asn Glu Leu Leu Val Pro Thr
            290                 295                 300

Gly Lys Pro Gly Leu Gly Pro Gly Thr Gly Gln Pro Thr Ser Arg Trp
305             310                 315                 320

His Ala Val Pro Pro Gln His Thr Leu Gly Ser Val Pro Gly Ser Ser
                325                 330                 335

Ile Ala Leu Arg Pro Arg Pro Gly Glu Pro Gly Arg Asp Leu Ala Ser
            340                 345                 350

Ser Glu Asn Gly Thr Glu Cys Arg Ser Gly Phe Val Arg His Asn Gly
            355                 360                 365

Ser Cys Arg Ser Val Cys Asp Leu Phe Pro Ser Tyr Cys His Asn Gly
            370                 375                 380

Gly Gln Cys Tyr Leu Val Glu Asn Ile Gly Ala Phe Cys Arg Cys Asn
385                 390                 395                 400
```

```
Thr Gln Asp Tyr Ile Trp His Lys Gly Met Arg Cys Glu Ser Ile Ile
            405                 410                 415

Thr Asp Phe Gln Val Met Cys Val Ala Val Gly Ser Ala Ala Leu Val
        420                 425                 430

Leu Leu Leu Leu Phe Met Met Thr Val Phe Ala Lys Lys Leu Tyr
            435                 440                 445

Leu Leu Lys Thr Glu Asn Thr Lys Leu Arg Arg Thr Lys Met Ile Leu
    450                 455                 460

Val Leu Pro Thr Lys Ser Arg Arg Phe Ser Ser Pro Ala
465                 470                 475

<210> SEQ ID NO 11
<211> LENGTH: 2334
<212> TYPE: DNA
<213> ORGANISM: Homo sapiens
<220> FEATURE:
<221> NAME/KEY: CDS
<222> LOCATION: (669)..(1955)
<223> OTHER INFORMATION:

<400> SEQUENCE: 11
```

| | |
|---|---|
| agtccagtga ggaataactg tagataagat gagatgatgg gcattaagtg taactgctga | 60 |
| gaagccttca tagagggaaa ggtgataaga actgagtttt tctggcatga ggagtttacc | 120 |
| aggcaggaga ggtggagacg ctaggctagg caaataggct gcagccatag ttctgctgag | 180 |
| aaacaggttt tgaaccaagg caactccatc tggagatatg tatcagaaag attaggagat | 240 |
| agaatctcca tcttggtcac ttatttggtc ttctaagaca gcaatgggac cgtctcttaa | 300 |
| atactggagt tgtcctatct ccttgggctg ataccctgaa ctgtcatttg gcgcgtgagg | 360 |
| cgggcagcgc ggttgaggcc gaagagctgg tgaaggcag cccggcgtgg gagccgcctg | 420 |
| ccaacgacac gcgggaagaa gccggcccac cagcggctgg ggaagatgag cgtcgtgga | 480 |
| cggcgcccgg tggcgagctg gccgggccag aagaggtgct gcaggagtcg gctgcggtga | 540 |
| ccggcaccgc ctggctggaa gctgacagcc caggcctggg aggagtgacc gcagaggcgg | 600 |
| gcagcggcga tgcccaggcc cttccagcta cgctccaggc tccccacgag gtcctcgggc | 660 |

```
agtcaatc atg ccc cct gcc att cct gag gct aca gag gcc agc ggg cca   710
         Met Pro Pro Ala Ile Pro Glu Ala Thr Glu Ala Ser Gly Pro
           1               5                  10 ccc tcc ccc acc ccc ggc gac aag ctg agc cca gct tct gaa ctc ccc    758
Pro Ser Pro Thr Pro Gly Asp Lys Leu Ser Pro Ala Ser Glu Leu Pro
 15              20                  25                  30 aag gag agc ccc ttg gag gtt tgg ctg aac ctg ggg gc agc aca ccc     806
Lys Glu Ser Pro Leu Glu Val Trp Leu Asn Leu Gly Gly Ser Thr Pro
             35                  40                  45 gac cct caa ggg cca gag ctg act tac cca ttt cag ggc acc ctg gag   854
Asp Pro Gln Gly Pro Glu Leu Thr Tyr Pro Phe Gln Gly Thr Leu Glu
         50                  55                  60 ccc caa ccg gca tca gat atc att gac atc gac tac ttc gaa gga ctg   902
Pro Gln Pro Ala Ser Asp Ile Ile Asp Ile Asp Tyr Phe Glu Gly Leu
     65                  70                  75 gat ggt gag ggt cgt ggc gca gat ctg ggg agc ttc cca ggg tca cca   950
Asp Gly Glu Gly Arg Gly Ala Asp Leu Gly Ser Phe Pro Gly Ser Pro
 80                  85                  90 gga acc tca gag aac cac cct gat act gag gga gag acc cct tcc tgg   998
Gly Thr Ser Glu Asn His Pro Asp Thr Glu Gly Glu Thr Pro Ser Trp
 95                 100                 105                 110 agc ctg ctt gac tta tac gat gat ttc acc ccc ttc gat gaa tct gat   1046
```

```
Ser Leu Leu Asp Leu Tyr Asp Asp Phe Thr Pro Phe Asp Glu Ser Asp
            115                 120                 125 ttc tac ccc acc aca tcc ttt tat gat gac ttg gat gaa gag gag gag       1094
Phe Tyr Pro Thr Thr Ser Phe Tyr Asp Asp Leu Asp Glu Glu Glu Glu
            130                 135                 140 gaa gag gag gat gac aaa gat gca gta gga ggt gga gac cta gaa gat       1142
Glu Glu Glu Asp Asp Lys Asp Ala Val Gly Gly Gly Asp Leu Glu Asp
            145                 150                 155 gaa aat gag ctt cta gtg ccc act ggg aag cct ggt ctg ggg ccc ggg       1190
Glu Asn Glu Leu Leu Val Pro Thr Gly Lys Pro Gly Leu Gly Pro Gly
160                 165                 170 aca ggc cag ccc acc agt cgg tgg cat gct gtc cct cca cag cac act       1238
Thr Gly Gln Pro Thr Ser Arg Trp His Ala Val Pro Pro Gln His Thr
175                 180                 185                 190 ctg ggg tcg gtc ccc ggc agc agc atc gcc ctc agg ccc cgc cca gga       1286
Leu Gly Ser Val Pro Gly Ser Ser Ile Ala Leu Arg Pro Arg Pro Gly
                195                 200                 205 gag cca ggc agg gac ttg gcc tcc agt gaa aat ggc act gag tgc cgc       1334
Glu Pro Gly Arg Asp Leu Ala Ser Ser Glu Asn Gly Thr Glu Cys Arg
            210                 215                 220 agt ggc ttt gtg cgg cat aac ggc tcc tgc cgg tca gtg tgc gac ctc       1382
Ser Gly Phe Val Arg His Asn Gly Ser Cys Arg Ser Val Cys Asp Leu
            225                 230                 235 ttc cca agt tac tgt cac aat ggc ggc cag tgc tac ctg gtg gag aac       1430
Phe Pro Ser Tyr Cys His Asn Gly Gly Gln Cys Tyr Leu Val Glu Asn
240                 245                 250 ata ggg gcc ttc tgc agg tgc aac acg cag gac tac atc tgg cac aag       1478
Ile Gly Ala Phe Cys Arg Cys Asn Thr Gln Asp Tyr Ile Trp His Lys
255                 260                 265                 270 ggg atg cgc tgc gag tcc atc atc acc gac ttc cag gtg atg tgc gtg       1526
Gly Met Arg Cys Glu Ser Ile Ile Thr Asp Phe Gln Val Met Cys Val
                275                 280                 285 gcc gtg ggc tcg gct gcc ctc gtc ctg ctc ctc ttc atg atg acg           1574
Ala Val Gly Ser Ala Ala Leu Val Leu Leu Leu Phe Met Met Thr
            290                 295                 300 gtg ttc ttt gcc aag aag ctc tac ctg ctc aag acg gag aat acc aag       1622
Val Phe Phe Ala Lys Lys Leu Tyr Leu Leu Lys Thr Glu Asn Thr Lys
            305                 310                 315 ctg cgt agg acc aac aaa ttc cgg acc cca tct gag ctc cac aat gat       1670
Leu Arg Arg Thr Asn Lys Phe Arg Thr Pro Ser Glu Leu His Asn Asp
320                 325                 330 aac ttc tcc ctc tcc acc att gcc gag ggc tct cac cca aat gta agg       1718
Asn Phe Ser Leu Ser Thr Ile Ala Glu Gly Ser His Pro Asn Val Arg
335                 340                 345                 350 aaa ctt tgc aac act ccc cgt acc tcc tcc ccc cat gcc cgt gcc ttg       1766
Lys Leu Cys Asn Thr Pro Arg Thr Ser Ser Pro His Ala Arg Ala Leu
                355                 360                 365 gct cac tat gat aac gtt atc tgt cag gat gat cct agt gct ccc cac       1814
Ala His Tyr Asp Asn Val Ile Cys Gln Asp Asp Pro Ser Ala Pro His
            370                 375                 380 aaa atc cag gag gtt ctc aag tcc tgc ctg aaa gag gag gag tca ttt       1862
Lys Ile Gln Glu Val Leu Lys Ser Cys Leu Lys Glu Glu Glu Ser Phe
            385                 390                 395 aac atc cag aac tcc atg tcg ccc aaa ctt gag ggt ggc aaa ggt gac       1910
Asn Ile Gln Asn Ser Met Ser Pro Lys Leu Glu Gly Gly Lys Gly Asp
            400                 405                 410 cag gct gac ttg gat gtg aac tgt ctt cag aat aat tta acc taa           1955
Gln Ala Asp Leu Asp Val Asn Cys Leu Gln Asn Asn Leu Thr
415                 420                 425
```

```
agcagagcaa gaagagagga agcgggggta gtgggtgggg ggtaggggaa gaaacattat    2015
ctcctcttgt acagagtcta tttcttgtaa ccatttgtta aactctttc ttttctgat     2075 ctcatggcat gcttttatgt attttgtaca ggaggcaaaa aaatacttaa aataagcaaa    2135
gaaactgaac agaattgcat acattgggtt gttttttctg tgctgtctgt acattgcttc    2195
tgctgctgtg atttctaaac ctgtgctgtt attcaactga ctttttttg tactttgacc    2255 cacgtttttt tgaaatacca gtaaaaaaca aagttcttga aataaaactt tttaaaaagt    2315
taaaaaaaaa aaaaaaaaa                                                 2334

<210> SEQ ID NO 12
<211> LENGTH: 428
<212> TYPE: PRT
<213> ORGANISM: Homo sapiens

<400> SEQUENCE: 12

Met Pro Pro Ala Ile Pro Glu Ala Thr Glu Ala Ser Gly Pro Pro Ser
1               5                   10                  15

Pro Thr Pro Gly Asp Lys Leu Ser Pro Ala Ser Glu Leu Pro Lys Glu
            20                  25                  30

Ser Pro Leu Glu Val Trp Leu Asn Leu Gly Gly Ser Thr Pro Asp Pro
        35                  40                  45

Gln Gly Pro Glu Leu Thr Tyr Pro Phe Gln Gly Thr Leu Glu Pro Gln
    50                  55                  60

Pro Ala Ser Asp Ile Ile Asp Ile Asp Tyr Phe Glu Gly Leu Asp Gly
65                  70                  75                  80

Glu Gly Arg Gly Ala Asp Leu Gly Ser Phe Pro Gly Ser Pro Gly Thr
                85                  90                  95

Ser Glu Asn His Pro Asp Thr Glu Gly Glu Thr Pro Ser Trp Ser Leu
            100                 105                 110

Leu Asp Leu Tyr Asp Asp Phe Thr Pro Phe Asp Glu Ser Asp Phe Tyr
        115                 120                 125

Pro Thr Thr Ser Phe Tyr Asp Asp Leu Asp Glu Glu Glu Glu Glu
    130                 135                 140

Glu Asp Asp Lys Asp Ala Val Gly Gly Asp Leu Glu Asp Glu Asn
145                 150                 155                 160

Glu Leu Leu Val Pro Thr Gly Lys Pro Gly Leu Gly Pro Gly Thr Gly
                165                 170                 175

Gln Pro Thr Ser Arg Trp His Ala Val Pro Pro Gln His Thr Leu Gly
            180                 185                 190

Ser Val Pro Gly Ser Ser Ile Ala Leu Arg Pro Arg Pro Gly Glu Pro
        195                 200                 205

Gly Arg Asp Leu Ala Ser Glu Asn Gly Thr Glu Cys Arg Ser Gly
    210                 215                 220

Phe Val Arg His Asn Gly Ser Cys Arg Ser Val Cys Asp Leu Phe Pro
225                 230                 235                 240

Ser Tyr Cys His Asn Gly Gly Gln Cys Tyr Leu Val Glu Asn Ile Gly
                245                 250                 255

Ala Phe Cys Arg Cys Asn Thr Gln Asp Tyr Ile Trp His Lys Gly Met
            260                 265                 270

Arg Cys Glu Ser Ile Ile Thr Asp Phe Gln Val Met Cys Val Ala Val
        275                 280                 285

Gly Ser Ala Ala Leu Val Leu Leu Leu Phe Met Thr Val Phe
    290                 295                 300
```

```
Phe Ala Lys Lys Leu Tyr Leu Leu Lys Thr Glu Asn Thr Lys Leu Arg
305                 310                 315                 320

Arg Thr Asn Lys Phe Arg Thr Pro Ser Glu Leu His Asn Asp Asn Phe
            325                 330                 335

Ser Leu Ser Thr Ile Ala Glu Gly Ser His Pro Asn Val Arg Lys Leu
                340                 345                 350

Cys Asn Thr Pro Arg Thr Ser Ser Pro His Ala Arg Ala Leu Ala His
            355                 360                 365

Tyr Asp Asn Val Ile Cys Gln Asp Asp Pro Ser Ala Pro His Lys Ile
370                 375                 380

Gln Glu Val Leu Lys Ser Cys Leu Lys Glu Glu Ser Phe Asn Ile
385                 390                 395                 400

Gln Asn Ser Met Ser Pro Lys Leu Glu Gly Gly Lys Gly Asp Gln Ala
            405                 410                 415

Asp Leu Asp Val Asn Cys Leu Gln Asn Asn Leu Thr
            420                 425

<210> SEQ ID NO 13
<211> LENGTH: 2592
<212> TYPE: DNA
<213> ORGANISM: Felis catus
<220> FEATURE:
<221> NAME/KEY: CDS
<222> LOCATION: (1)..(2217)
<223> OTHER INFORMATION:

<400> SEQUENCE: 13 atg ggc ttt ggc tat gga cgg att agg tct gat ccg att aga gcc cgg      48
Met Gly Phe Gly Tyr Gly Arg Ile Arg Ser Asp Pro Ile Arg Ala Arg
1               5                   10                  15 gcc gtc ggc ttc gcc ccc ttg cct ggc gct gcc agc gcc cgc ccc gcc      96
Ala Val Gly Phe Ala Pro Leu Pro Gly Ala Ala Ser Ala Arg Pro Ala
                20                  25                  30 ctc gtg gac acc cgc aga cct ccc cga gac cct tcc cct ccc cga aca     144
Leu Val Asp Thr Arg Arg Pro Pro Arg Asp Pro Ser Pro Pro Arg Thr
            35                  40                  45 cgg cat tgg cgc aga aat ctg aga ggt ccg tgc acc ccg ggc tcg gct     192
Arg His Trp Arg Arg Asn Leu Arg Gly Pro Cys Thr Pro Gly Ser Ala
        50                  55                  60 cat ttc cac agc tcc agc tcg ggc ttc cgc ccc ctg cgg ccc ttc cga     240
His Phe His Ser Ser Ser Ser Gly Phe Arg Pro Leu Arg Pro Phe Arg
65                  70                  75                  80 gcc ccg ccc caa gct tgc ggg tgt ctg ggc ccc cgc ctc cgt gct cgc     288
Ala Pro Pro Gln Ala Cys Gly Cys Leu Gly Pro Arg Leu Arg Ala Arg
                85                  90                  95 cgc gtg gcg ggt ggg ttc ctc gca ggt ggg ggg ccc gtg cca gct ctc     336
Arg Val Ala Gly Gly Phe Leu Ala Gly Gly Gly Pro Val Pro Ala Leu
            100                 105                 110 cac ggg gag ggc ggg ccc cgc ccc aca ggt ctc ccg ccc gtg cac ctg     384
His Gly Glu Gly Gly Pro Arg Pro Thr Gly Leu Pro Pro Val His Leu
        115                 120                 125 tcg gct aac gcc acg cac ggc gct gtg ctc cgc acc cgc gct act cca     432
Ser Ala Asn Ala Thr His Gly Ala Val Leu Arg Thr Arg Ala Thr Pro
    130                 135                 140 cgt ccg ttt gtc tcg gcg tcc cga gcc ggg ggt acc gac tgc gac cag     480
Arg Pro Phe Val Ser Ala Ser Arg Ala Gly Gly Thr Asp Cys Asp Gln
145                 150                 155                 160 gac ccc cgc ggc cct cgc gcc cca ccc tgg gcc agg gtc ccg ctg gcc     528
Asp Pro Arg Gly Pro Arg Ala Pro Pro Trp Ala Arg Val Pro Leu Ala
                165                 170                 175
```

-continued

| | |
|---|---|
| tcg ggt aca ggc gga gtt agc gag ctg tgg caa ggg ggc ggg gca gct<br>Ser Gly Thr Gly Gly Val Ser Glu Leu Trp Gln Gly Gly Gly Ala Ala<br>           180                   185               190 | 576 |
| cct tgc ccg cga ccg ggg cgg ggg aag ggg cgc gcg aag agg tgg gat<br>Pro Cys Pro Arg Pro Gly Arg Gly Lys Gly Arg Ala Lys Arg Trp Asp<br>           195                   200               205 | 624 |
| act tgg ggg agg ccg agg ggt tgg ggg cgg ccc cgg ccc ggg tgt ccg<br>Thr Trp Gly Arg Pro Arg Gly Trp Gly Arg Pro Arg Pro Gly Cys Pro<br>210                   215                   220 | 672 |
| gac aga gcc cgt gag gct ggc agc gcc gtc gag gcc cac gag cag gtg<br>Asp Arg Ala Arg Glu Ala Gly Ser Ala Val Glu Ala His Glu Gln Val<br>225                   230                   235               240 | 720 |
| aag agc atc ctg gcg agg gag ccg act gcc aac gaa acg agg gag aag<br>Lys Ser Ile Leu Ala Arg Glu Pro Thr Ala Asn Glu Thr Arg Glu Lys<br>           245                   250               255 | 768 |
| gcc ggc cca cca gca gct gag gaa gac gag acc tcg tgg acc gca cct<br>Ala Gly Pro Pro Ala Ala Glu Glu Asp Glu Thr Ser Trp Thr Ala Pro<br>               260                   265               270 | 816 |
| ggc ggt gag cag gcc atg atg ggg cct agt gtc ggg cca gag gag gtg<br>Gly Gly Glu Gln Ala Met Met Gly Pro Ser Val Gly Pro Glu Glu Val<br>           275                   280               285 | 864 |
| ctg gag gcg tcg gca gcg gtg acc ggc gca ccc tgg ctg gag gct gac<br>Leu Glu Ala Ser Ala Ala Val Thr Gly Ala Pro Trp Leu Glu Ala Asp<br>          290                   295               300 | 912 |
| agc cct ggc ctg ggt gga gtg acc gca gag gcc ggc agc ggc gac acc<br>Ser Pro Gly Leu Gly Gly Val Thr Ala Glu Ala Gly Ser Gly Asp Thr<br>305                 310                   315               320 | 960 |
| cag gcc ctt cca gct acg ctc ccg gct ccc aag gag gcc ctg gga cag<br>Gln Ala Leu Pro Ala Thr Leu Pro Ala Pro Lys Glu Ala Leu Gly Gln<br>               325                   330               335 | 1008 |
| tca tcg atg gcc ccc tcc atc ccc aag gct aca gag gcc agc aga cca<br>Ser Ser Met Ala Pro Ser Ile Pro Lys Ala Thr Glu Ala Ser Arg Pro<br>             340                   345               350 | 1056 |
| ccc tcc ccc aca cct ggc gac atg ctg agc ccc ggc cca gaa cac ccc<br>Pro Ser Pro Thr Pro Gly Asp Met Leu Ser Pro Gly Pro Glu His Pro<br>          355                   360               365 | 1104 |
| aag gag agt ccc ttg gag gtt tgg ttg aac ctg gga ggc agc aca cat<br>Lys Glu Ser Pro Leu Glu Val Trp Leu Asn Leu Gly Gly Ser Thr His<br>370                 375                   380 | 1152 |
| gac cct cat ggg cca gag ccc aca ttc ccc ttt cag ggc aca atg gag<br>Asp Pro His Gly Pro Glu Pro Thr Phe Pro Phe Gln Gly Thr Met Glu<br>385                 390                   395               400 | 1200 |
| ccc cag cca gtg tca gat ata att gac atc gac tac ttc gaa gga ttg<br>Pro Gln Pro Val Ser Asp Ile Ile Asp Ile Asp Tyr Phe Glu Gly Leu<br>                 405                   410               415 | 1248 |
| gat ggt gag ggc cgt ggt gcc gac ctg gag agc ttc cca ggg tcg cca<br>Asp Gly Glu Gly Arg Gly Ala Asp Leu Glu Ser Phe Pro Gly Ser Pro<br>           420                   425               430 | 1296 |
| gga acc tca gag cac cac cct gat act ggg gga gag acc cct tcc tgg<br>Gly Thr Ser Glu His His Pro Asp Thr Gly Gly Glu Thr Pro Ser Trp<br>               435                   440               445 | 1344 |
| agc ctg ctt gac tta tac gat gac ttc acc ccc ttt gat gaa tct gac<br>Ser Leu Leu Asp Leu Tyr Asp Asp Phe Thr Pro Phe Asp Glu Ser Asp<br>450                 455                   460 | 1392 |
| ttc tac ccc acc aca tcc ttc tat gat gac ctt gat gaa gag gag gag<br>Phe Tyr Pro Thr Thr Ser Phe Tyr Asp Asp Leu Asp Glu Glu Glu Glu<br>465                 470                   475               480 | 1440 |
| gaa gag gat gac aag gat gca gcg gga ggt gaa gac ctg gaa gat gaa<br>Glu Glu Asp Asp Lys Asp Ala Ala Gly Gly Glu Asp Leu Glu Asp Glu | 1488 |

```
                    485             490             495
agt gac ctt ctg gtg cct acc gag aag cct ggt ctg ggg ccc ggg act    1536
Ser Asp Leu Leu Val Pro Thr Glu Lys Pro Gly Leu Gly Pro Gly Thr
        500             505             510 ggc cag cct acc agt cgg tgg cat gct gtg ccc cca cag cat act ctg    1584
Gly Gln Pro Thr Ser Arg Trp His Ala Val Pro Pro Gln His Thr Leu
    515             520             525 ggg atg gtc cct ggc agc agc atc gcc ctc agg ccc cgc cct gga gag    1632
Gly Met Val Pro Gly Ser Ser Ile Ala Leu Arg Pro Arg Pro Gly Glu
530             535             540 cca ggc agg gac ctg acc cca agc gag aat ggc act gag tgc cgc agc    1680
Pro Gly Arg Asp Leu Thr Pro Ser Glu Asn Gly Thr Glu Cys Arg Ser
545             550             555             560 ggc ttt gtg cga cat aac ggc tcc tgc cgg tca gtg tgc gac ctc ttt    1728
Gly Phe Val Arg His Asn Gly Ser Cys Arg Ser Val Cys Asp Leu Phe
            565             570             575 cca agt tac tgt cac aat ggc ggc cag tgc tac ctg gtg gag aac ata    1776
Pro Ser Tyr Cys His Asn Gly Gly Gln Cys Tyr Leu Val Glu Asn Ile
        580             585             590 ggg gcc ttc tgc agg tgc aac aca cag gac tac atc tgg cac aag ggg    1824
Gly Ala Phe Cys Arg Cys Asn Thr Gln Asp Tyr Ile Trp His Lys Gly
    595             600             605 atg cgc tgc gag tcc atc atc acc gac ttc cag gtg atg tgc gtg gcc    1872
Met Arg Cys Glu Ser Ile Ile Thr Asp Phe Gln Val Met Cys Val Ala
610             615             620 gtc ggc tcg gct gcc ctt gta ctg ctc ctg ctc ttc atg atg aca gtg    1920
Val Gly Ser Ala Ala Leu Val Leu Leu Leu Phe Met Met Thr Val
625             630             635             640 ttc ttc gcc aag aag cta tat ctg ctc aag aca gag aat acc aag ctg    1968
Phe Phe Ala Lys Lys Leu Tyr Leu Leu Lys Thr Glu Asn Thr Lys Leu
            645             650             655 cgt agg acc aac aaa ttc cgg acc ccg tct gaa ctc cac aac gat aac    2016
Arg Arg Thr Asn Lys Phe Arg Thr Pro Ser Glu Leu His Asn Asp Asn
        660             665             670 ttc tcc ctc tcc acc att gcc gaa ggc tct cac cca aac gat gac cct    2064
Phe Ser Leu Ser Thr Ile Ala Glu Gly Ser His Pro Asn Asp Asp Pro
    675             680             685 agt gct ccc cac aaa atc cag gaa gct ctc aag tcc tgc ctg aaa gag    2112
Ser Ala Pro His Lys Ile Gln Glu Ala Leu Lys Ser Cys Leu Lys Glu
690             695             700 gag gag tca ttt aac atc cag aac tcc atg tca ccc aaa ctt gag ggt    2160
Glu Glu Ser Phe Asn Ile Gln Asn Ser Met Ser Pro Lys Leu Glu Gly
705             710             715             720 ggc aaa ggt gac cag gct gac ttg gag gtg aac tgt ctt cag aat aac    2208
Gly Lys Gly Asp Gln Ala Asp Leu Glu Val Asn Cys Leu Gln Asn Asn
            725             730             735 cta acc taa agcagaacaa gaagagagga aatgggggga ggggggtac              2257
Leu Thr ggggagaaac atgacctcct cttgtacaga gtctatttct tgtaaccatt tgttaaactc   2317
ttttcttttt ctgatctcat ggcatgcttt gatgtatttt gtacaggagg ggaaacacac   2377
acacacacac acacacacac acacacacac acacacacta agcaaagaac ccagacaaaa   2437
ttgcatacgt tgggttgttt tgtctgtgct gtctgtacat tgcttctgct gctgtgattt   2497
ctaaacctac gctgttattc aactactttt tttttgtact ttgacccacc tttttttgaa   2557
ataagagtaa aaacaaagt tcttgaaata aaact                                2592
```

<210> SEQ ID NO 14

```
<211> LENGTH: 738
<212> TYPE: PRT
<213> ORGANISM: Felis catus

<400> SEQUENCE: 14

Met Gly Phe Gly Tyr Gly Arg Ile Arg Ser Asp Pro Ile Arg Ala Arg
1               5                   10                  15

Ala Val Gly Phe Ala Pro Leu Pro Gly Ala Ala Ser Ala Arg Pro Ala
            20                  25                  30

Leu Val Asp Thr Arg Arg Pro Arg Asp Pro Ser Pro Pro Arg Thr
        35                  40                  45

Arg His Trp Arg Arg Asn Leu Arg Gly Pro Cys Thr Pro Gly Ser Ala
    50                  55                  60

His Phe His Ser Ser Ser Gly Phe Arg Pro Leu Arg Pro Phe Arg
65                  70                  75                  80

Ala Pro Pro Gln Ala Cys Gly Cys Leu Gly Pro Arg Leu Arg Ala Arg
                85                  90                  95

Arg Val Ala Gly Gly Phe Leu Ala Gly Gly Pro Val Pro Ala Leu
                100                 105                 110

His Gly Glu Gly Gly Pro Arg Pro Thr Gly Leu Pro Pro Val His Leu
            115                 120                 125

Ser Ala Asn Ala Thr His Gly Ala Val Leu Arg Thr Arg Ala Thr Pro
130                 135                 140

Arg Pro Phe Val Ser Ala Ser Arg Ala Gly Gly Thr Asp Cys Asp Gln
145                 150                 155                 160

Asp Pro Arg Gly Pro Arg Ala Pro Pro Trp Ala Arg Val Pro Leu Ala
                165                 170                 175

Ser Gly Thr Gly Gly Val Ser Glu Leu Trp Gln Gly Gly Gly Ala Ala
            180                 185                 190

Pro Cys Pro Arg Pro Gly Arg Gly Lys Gly Arg Ala Lys Arg Trp Asp
        195                 200                 205

Thr Trp Gly Arg Pro Arg Gly Trp Gly Arg Pro Arg Pro Gly Cys Pro
    210                 215                 220

Asp Arg Ala Arg Glu Ala Gly Ser Ala Val Glu Ala His Glu Gln Val
225                 230                 235                 240

Lys Ser Ile Leu Ala Arg Glu Pro Thr Ala Asn Glu Thr Arg Glu Lys
                245                 250                 255

Ala Gly Pro Pro Ala Ala Glu Glu Asp Glu Thr Ser Trp Thr Ala Pro
            260                 265                 270

Gly Gly Glu Gln Ala Met Met Gly Pro Ser Val Gly Pro Glu Glu Val
        275                 280                 285

Leu Glu Ala Ser Ala Ala Val Thr Gly Ala Pro Trp Leu Glu Ala Asp
    290                 295                 300

Ser Pro Gly Leu Gly Gly Val Thr Ala Glu Ala Gly Ser Gly Asp Thr
305                 310                 315                 320

Gln Ala Leu Pro Ala Thr Leu Pro Ala Pro Lys Glu Ala Leu Gly Gln
                325                 330                 335

Ser Ser Met Ala Pro Ser Ile Pro Lys Ala Thr Glu Ala Ser Arg Pro
            340                 345                 350

Pro Ser Pro Thr Pro Gly Asp Met Leu Ser Pro Gly Pro Glu His Pro
        355                 360                 365

Lys Glu Ser Pro Leu Glu Val Trp Leu Asn Leu Gly Gly Ser Thr His
    370                 375                 380

Asp Pro His Gly Pro Glu Pro Thr Phe Pro Phe Gln Gly Thr Met Glu
```

```
              385                 390                 395                 400
         Pro Gln Pro Val Ser Asp Ile Ile Asp Ile Asp Tyr Phe Glu Gly Leu
                         405                 410                 415

Asp Gly Glu Gly Arg Gly Ala Asp Leu Glu Ser Phe Pro Gly Ser Pro
                         420                 425                 430

Gly Thr Ser Glu His His Pro Asp Thr Gly Gly Glu Thr Pro Ser Trp
                         435                 440                 445

Ser Leu Leu Asp Leu Tyr Asp Asp Phe Thr Pro Phe Asp Glu Ser Asp
         450                 455                 460

Phe Tyr Pro Thr Thr Ser Phe Tyr Asp Asp Leu Asp Glu Glu Glu Glu
         465                 470                 475                 480

Glu Glu Asp Asp Lys Asp Ala Ala Gly Gly Glu Asp Leu Glu Asp Glu
                         485                 490                 495

Ser Asp Leu Leu Val Pro Thr Glu Lys Pro Gly Leu Gly Pro Gly Thr
                         500                 505                 510

Gly Gln Pro Thr Ser Arg Trp His Ala Val Pro Pro Gln His Thr Leu
                         515                 520                 525

Gly Met Val Pro Gly Ser Ser Ile Ala Leu Arg Pro Arg Pro Gly Glu
                         530                 535                 540

Pro Gly Arg Asp Leu Thr Pro Ser Glu Asn Gly Thr Glu Cys Arg Ser
         545                 550                 555                 560

Gly Phe Val Arg His Asn Gly Ser Cys Arg Ser Val Cys Asp Leu Phe
                         565                 570                 575

Pro Ser Tyr Cys His Asn Gly Gly Gln Cys Tyr Leu Val Glu Asn Ile
                         580                 585                 590

Gly Ala Phe Cys Arg Cys Asn Thr Gln Asp Tyr Ile Trp His Lys Gly
                         595                 600                 605

Met Arg Cys Glu Ser Ile Ile Thr Asp Phe Gln Val Met Cys Val Ala
                         610                 615                 620

Val Gly Ser Ala Ala Leu Val Leu Leu Leu Leu Phe Met Met Thr Val
         625                 630                 635                 640

Phe Phe Ala Lys Lys Leu Tyr Leu Leu Lys Thr Glu Asn Thr Lys Leu
                         645                 650                 655

Arg Arg Thr Asn Lys Phe Arg Thr Pro Ser Glu Leu His Asn Asp Asn
                         660                 665                 670

Phe Ser Leu Ser Thr Ile Ala Glu Gly Ser His Pro Asn Asp Asp Pro
                         675                 680                 685

Ser Ala Pro His Lys Ile Gln Glu Ala Leu Lys Ser Cys Leu Lys Glu
         690                 695                 700

Glu Glu Ser Phe Asn Ile Gln Asn Ser Met Ser Pro Lys Leu Glu Gly
         705                 710                 715                 720

Gly Lys Gly Asp Gln Ala Asp Leu Glu Val Asn Cys Leu Gln Asn Asn
                         725                 730                 735

Leu Thr

<210> SEQ ID NO 15
<211> LENGTH: 3881
<212> TYPE: DNA
<213> ORGANISM: Mus musculus
<220> FEATURE:
<221> NAME/KEY: CDS
<222> LOCATION: (1816)..(3516)
<223> OTHER INFORMATION:

<400> SEQUENCE: 15
```

```
atttctctgc agggagggga gaagatagtt gaggaaggaa atatttcaca ttcgcttgtt    60
tgttctactg atcaaaacag aatttaaaag gatagttacg ggtgggaaat agggtagata   120
gaaggatttg gttggttagt tggttctaga cagggattac agacataagc taccataacc   180
agcaaataca attattttgc agtactagga attgaacctg aagtctcact cattttaggc   240
aagtgctctc cctaactctt aagtgtttta ccataagtag gaaaagactt tattgtgacc   300
atgccctagc atgaaaggac ttacatagga tctcctgtgt ggtaggaact tccaccaaca   360 tccactttg acaactacca cccaggaatt gaagagagaa ataggtatta tatctgggta    420
agcaagcccc ctcttgactg gaactccaaa ctaggacacg tatgtctggt tgccactctc   480
tagatgtcat acagacccta catagccacc tccgagccag gatataagag cctagctgct   540
ggaattttgt cagccttgag gggactctaa gctgcaacca tacttgtgag agaaaaggag   600
tgttgaacca aggcaactca ctagaagaca ggtatgagac agattaaatg atggtcctcc   660
atcttgttca tatttggtca ctgacagaag actatcaaca ccagcatcgc ccttggacta   720
acccttggac tgagctgaac atgatcattt aggtcgataa taaaacatca atatgtaggc   780
tatttggagg cggggaaagc caggtgacta agctgtagtt ctgcctccct tccaacaggt   840
ctcccagtaa gcagtgaacc tgggttagga acagagacct ctctctccac gttgcatgtg   900
cacctggcag tgatctagac ctcttggttt aaccaggaac ttgggtttgg gtagtactgg   960
tcacctgcgg aaggccgccc tggatttaga aaacgcaagg tggagtccaa atactgggga  1020
ccggataaca cgttgggtgg acctggctgt gcaagattta aactaatggc tttggctgtg  1080
gacagattag gtctgatcca attagagcct aggccgtagt attcgcctcc ttgccaggct  1140
ctgtcgatgt tctccctgct ctccggaaga agacttagag tcggactgga gaaccttctg  1200
gacaccgaat tctggattgg caccggacag tccgtgcccc gggctccgct ctctccacac  1260 tggggcgcg ggcttccgcc ccctgtggcc cttccgagcc ccgccccgag cctgcgggtg   1320
tcggagcccg cgacgtcccc gcctcccctg cgcgcgcgtg gcgggtgggt tcctcgcagg  1380
tccgcggccc agcgcgctca gcactggaag cgcaagcggg cccccgtgggc tgccgccggt  1440 gcacctgtcg gcttccccca gtggctctgc tgccgcccct gcgcgccgcg cttgcatcgc  1500
tctccacgtc ccgtgccaga ggggtctgac tgtcccctgg cgaggaagac cgagagggc   1560 cggcgtcaac gcgacgtgct gcggggcggg cggagtgggg gcggcgccga acgcggcagc  1620
ggcaagcggc agcggcggcg cgggaggcgg ggaggcgcgg cgctcggagg acagcggctg  1680
acggcggcat gcgcggctc atgctgccca ccgtgggctg aggcggccgc acacgggcgg   1740
caggcgcagc ggccgggcaa gccgagggcg cagccaagcc gcgcgcaccg cgcacagcgg  1800 cagggggctcc gcgca atg ggc cga gct gga ggc ggg ggc ccg gac tgg ggg  1851
                  Met Gly Arg Ala Gly Gly Gly Gly Pro Asp Trp Gly
                    1               5                  10 ccg ccg cca gtg ctg ctg ctt ctg ggg gtc acg ctg gtg ctc acc gct    1899
Pro Pro Pro Val Leu Leu Leu Leu Gly Val Thr Leu Val Leu Thr Ala
            15                  20                  25 ggg gcc gta ccg gca cgg gaa aca ggc agt gcg atc gag gct gaa gag    1947
Gly Ala Val Pro Ala Arg Glu Thr Gly Ser Ala Ile Glu Ala Glu Glu
        30                  35                  40 ctg gtg agg agc agc ctg gca tgg gag tcg cgt gcc aat gac acg cgg    1995
Leu Val Arg Ser Ser Leu Ala Trp Glu Ser Arg Ala Asn Asp Thr Arg
45                  50                  55                  60 gag gaa gcc ggc ctg cca gca gct ggg gaa gat gag acc tcg tgg aca    2043
Glu Glu Ala Gly Leu Pro Ala Ala Gly Glu Asp Glu Thr Ser Trp Thr
                65                  70                  75
```

```
gag cgg ggc agt gag atg gct gcg gtg ggc cct ggg gtc ggg cca gag      2091
Glu Arg Gly Ser Glu Met Ala Ala Val Gly Pro Gly Val Gly Pro Glu
            80                  85                  90 gag gca cta gag gca tcg gct gca gtg act ggc act gcc tgg cta gag      2139
Glu Ala Leu Glu Ala Ser Ala Ala Val Thr Gly Thr Ala Trp Leu Glu
        95                  100                 105 gca gat ggc cca ggc ctg ggt gga gtg act gca gag gct ggc agt ggc      2187
Ala Asp Gly Pro Gly Leu Gly Gly Val Thr Ala Glu Ala Gly Ser Gly
    110                 115                 120 gac gcc cag acc ctt cca gct acg ctc cag gct cct gat gag gcc ctt      2235
Asp Ala Gln Thr Leu Pro Ala Thr Leu Gln Ala Pro Asp Glu Ala Leu
125                 130                 135                 140 ggg tca tct aca atg ccc cct gcc atc cct gag gct act gaa acc agt      2283
Gly Ser Ser Thr Met Pro Pro Ala Ile Pro Glu Ala Thr Glu Thr Ser
                145                 150                 155 gga cct ccc tcc cct gct gtc cat gat aag cct agt gta ggc cct gaa      2331
Gly Pro Pro Ser Pro Ala Val His Asp Lys Pro Ser Val Gly Pro Glu
            160                 165                 170 ctc cct aaa gag atc ccc ttg gag gtt cgg ctg aac ctg gga ggc agc      2379
Leu Pro Lys Glu Ile Pro Leu Glu Val Arg Leu Asn Leu Gly Gly Ser
        175                 180                 185 aca cca gag ccc act ttt ccc ctt cag ggc act ctc gag acc caa cca      2427
Thr Pro Glu Pro Thr Phe Pro Leu Gln Gly Thr Leu Glu Thr Gln Pro
    190                 195                 200 gcc tca gat ata att gac att gat tac ttt gaa gga ttg gat agt gag      2475
Ala Ser Asp Ile Ile Asp Ile Asp Tyr Phe Glu Gly Leu Asp Ser Glu
205                 210                 215                 220 ggt cgt ggt gca gac atg ggc agc ttc ccg ggg tca cca gga acc tca      2523
Gly Arg Gly Ala Asp Met Gly Ser Phe Pro Gly Ser Pro Gly Thr Ser
                225                 230                 235 gaa aat cac cct gat acc gaa gga gag acc cct tcc tgg agc ctg ctt      2571
Glu Asn His Pro Asp Thr Glu Gly Glu Thr Pro Ser Trp Ser Leu Leu
            240                 245                 250 gat ttg tat gat gac ttc acc cct ttt gat gag tct gat ttc tac ccc      2619
Asp Leu Tyr Asp Asp Phe Thr Pro Phe Asp Glu Ser Asp Phe Tyr Pro
        255                 260                 265 acc aca tcc ttc tat gat gat ttg gaa gag gag gaa gaa gag gag gag      2667
Thr Thr Ser Phe Tyr Asp Asp Leu Glu Glu Glu Glu Glu Glu Glu Glu
    270                 275                 280 gat aag gat aca gta gga ggt gga gac ctg gaa gat gaa aac gac ctt      2715
Asp Lys Asp Thr Val Gly Gly Gly Asp Leu Glu Asp Glu Asn Asp Leu
285                 290                 295                 300 ctc ctg ccc tct caa aag cct ggt gtg ggg cct ggg aca gga cag ccc      2763
Leu Leu Pro Ser Gln Lys Pro Gly Val Gly Pro Gly Thr Gly Gln Pro
                305                 310                 315 acc aac cgg tgg cat gct gtt ccc cca cag cat act ctg ggg atg gta      2811
Thr Asn Arg Trp His Ala Val Pro Pro Gln His Thr Leu Gly Met Val
            320                 325                 330 cct ggc agc agc atc tct ctt agg ccc cgc ccc gga gat cca ggc aag      2859
Pro Gly Ser Ser Ile Ser Leu Arg Pro Arg Pro Gly Asp Pro Gly Lys
        335                 340                 345 gac ctg gcc tca gga gaa aat ggc aca gag tgc cga gtt ggc ttc gtc      2907
Asp Leu Ala Ser Gly Glu Asn Gly Thr Glu Cys Arg Val Gly Phe Val
    350                 355                 360 agg cac aat ggc tcc tgc cgg tca gtc tgt gac ctc ttt ccg agt tac      2955
Arg His Asn Gly Ser Cys Arg Ser Val Cys Asp Leu Phe Pro Ser Tyr
365                 370                 375                 380 tgt cac aac ggc ggc cag tgc tac ctg gtg gag aac ata ggg gct ttc      3003
Cys His Asn Gly Gly Gln Cys Tyr Leu Val Glu Asn Ile Gly Ala Phe
```

```
                    385                 390                 395
tgc agg tgt aac acc cag gac tac atc tgg cac aag ggg atg cgc tgt       3051
Cys Arg Cys Asn Thr Gln Asp Tyr Ile Trp His Lys Gly Met Arg Cys
            400                 405                 410 gag tcc atc atc acg gac ttc cag gtg atg tgc gtg gcc gtt ggc tcg       3099
Glu Ser Ile Ile Thr Asp Phe Gln Val Met Cys Val Ala Val Gly Ser
415                 420                 425 gct gct ctc gtg ctt ctc ctg ttc atg atg act gtg ttc ttt gcc           3147
Ala Ala Leu Val Leu Leu Leu Phe Met Met Thr Val Phe Phe Ala
        430                 435                 440 aag aag ctc tat ctg ctc aag act gag aat acc aag ctg cgg agg acc       3195
Lys Lys Leu Tyr Leu Leu Lys Thr Glu Asn Thr Lys Leu Arg Arg Thr
445                 450                 455                 460 aat aaa ttc cgg acc cca tct gag ctc cac aac gac aac ttc tcc ctc       3243
Asn Lys Phe Arg Thr Pro Ser Glu Leu His Asn Asp Asn Phe Ser Leu
                465                 470                 475 tcc acc att gcc gag ggc tct cat cca aat gta agg aaa ttt tgc gac       3291
Ser Thr Ile Ala Glu Gly Ser His Pro Asn Val Arg Lys Phe Cys Asp
            480                 485                 490 act ccc cgt gtc tcc tcc ccc cat gcc cgt gcc ttg gct cac tat gat       3339
Thr Pro Arg Val Ser Ser Pro His Ala Arg Ala Leu Ala His Tyr Asp
        495                 500                 505 aac att gtc tgt cag gac gac ccc agc gct ccc cac aaa atc cag gac       3387
Asn Ile Val Cys Gln Asp Asp Pro Ser Ala Pro His Lys Ile Gln Asp
510                 515                 520 cct ctc aag tcc cgc ctg aag gag gaa gag tcc ttt aac atc cag aac       3435
Pro Leu Lys Ser Arg Leu Lys Glu Glu Glu Ser Phe Asn Ile Gln Asn
525                 530                 535                 540 tcc atg tca ccc aaa ctt gag ggt ggc aaa ggt gac cag gat gac ttg       3483
Ser Met Ser Pro Lys Leu Glu Gly Gly Lys Gly Asp Gln Asp Asp Leu
                545                 550                 555 ggg gtg aac tgt ctg cag aat aac cta acc tga gactgaggaa gaagagagga    3536
Gly Val Asn Cys Leu Gln Asn Asn Leu Thr
            560                 565 aagggggtg ggggagggaa ggactgttgt ctcctctcgg gcagagtcgg cttcttgtaa      3596
ccatttgtta agcttttctt tttctgatct catggcatgc tctgatgtgt tttgtaggag     3656
gggaaacact taaaataagc aaagaaaccg agcaggattg catatatcgg atggttcttg     3716
tctgtgctct ctgtacgttg cttctgcagc tgtgatttct aaacctctgc tggcactcag     3776 ctgactttt gttttgtact ttgacccgcc ttttttttgga ataccaagtt aaaaaaaaaa    3836
agttcttgaa ataaaacttt ttaaaaagct gtccaaaaaa aaaaa                     3881

<210> SEQ ID NO 16
<211> LENGTH: 566
<212> TYPE: PRT
<213> ORGANISM: Mus musculus

<400> SEQUENCE: 16

Met Gly Arg Ala Gly Gly Gly Pro Asp Trp Gly Pro Pro Val
1               5                   10                  15

Leu Leu Leu Leu Gly Val Thr Leu Val Leu Thr Ala Gly Ala Val Pro
            20                  25                  30

Ala Arg Glu Thr Gly Ser Ala Ile Glu Ala Glu Leu Val Arg Ser
        35                  40                  45

Ser Leu Ala Trp Glu Ser Arg Ala Asn Asp Thr Arg Glu Glu Ala Gly
    50                  55                  60

Leu Pro Ala Ala Gly Glu Asp Glu Thr Ser Trp Thr Glu Arg Gly Ser
```

```
                65                  70                  75                  80
        Glu Met Ala Ala Val Gly Pro Gly Val Gly Pro Glu Glu Ala Leu Glu
                        85                  90                  95
        Ala Ser Ala Ala Val Thr Gly Thr Ala Trp Leu Glu Ala Asp Gly Pro
                        100                 105                 110
        Gly Leu Gly Gly Val Thr Ala Glu Ala Gly Ser Gly Asp Ala Gln Thr
                        115                 120                 125
        Leu Pro Ala Thr Leu Gln Ala Pro Asp Glu Ala Leu Gly Ser Ser Thr
                        130                 135                 140
        Met Pro Pro Ala Ile Pro Glu Ala Thr Glu Thr Ser Gly Pro Pro Ser
        145                 150                 155                 160
        Pro Ala Val His Asp Lys Pro Ser Val Gly Pro Glu Leu Pro Lys Glu
                        165                 170                 175
        Ile Pro Leu Glu Val Arg Leu Asn Leu Gly Gly Ser Thr Pro Glu Pro
                        180                 185                 190
        Thr Phe Pro Leu Gln Gly Thr Leu Glu Thr Gln Pro Ala Ser Asp Ile
                        195                 200                 205
        Ile Asp Ile Asp Tyr Phe Glu Gly Leu Asp Ser Glu Gly Arg Gly Ala
                        210                 215                 220
        Asp Met Gly Ser Phe Pro Gly Ser Pro Gly Thr Ser Glu Asn His Pro
        225                 230                 235                 240
        Asp Thr Glu Gly Glu Thr Pro Ser Trp Ser Leu Leu Asp Leu Tyr Asp
                        245                 250                 255
        Asp Phe Thr Pro Phe Asp Glu Ser Asp Phe Tyr Pro Thr Thr Ser Phe
                        260                 265                 270
        Tyr Asp Asp Leu Glu Glu Glu Glu Glu Glu Glu Asp Lys Asp Thr
                        275                 280                 285
        Val Gly Gly Gly Asp Leu Glu Asp Glu Asn Asp Leu Leu Leu Pro Ser
                        290                 295                 300
        Gln Lys Pro Gly Val Gly Pro Gly Thr Gly Gln Pro Thr Asn Arg Trp
        305                 310                 315                 320
        His Ala Val Pro Pro Gln His Thr Leu Gly Met Val Pro Gly Ser Ser
                        325                 330                 335
        Ile Ser Leu Arg Pro Arg Pro Gly Asp Pro Gly Lys Asp Leu Ala Ser
                        340                 345                 350
        Gly Glu Asn Gly Thr Glu Cys Arg Val Gly Phe Val Arg His Asn Gly
                        355                 360                 365
        Ser Cys Arg Ser Val Cys Asp Leu Phe Pro Ser Tyr Cys His Asn Gly
        370                 375                 380
        Gly Gln Cys Tyr Leu Val Glu Asn Ile Gly Ala Phe Cys Arg Cys Asn
        385                 390                 395                 400
        Thr Gln Asp Tyr Ile Trp His Lys Gly Met Arg Cys Glu Ser Ile Ile
                        405                 410                 415
        Thr Asp Phe Gln Val Met Cys Val Ala Val Gly Ser Ala Ala Leu Val
                        420                 425                 430
        Leu Leu Leu Leu Phe Met Met Thr Val Phe Phe Ala Lys Lys Leu Tyr
                        435                 440                 445
        Leu Leu Lys Thr Glu Asn Thr Lys Leu Arg Arg Thr Asn Lys Phe Arg
                        450                 455                 460
        Thr Pro Ser Glu Leu His Asn Asp Asn Phe Ser Leu Ser Thr Ile Ala
        465                 470                 475                 480
        Glu Gly Ser His Pro Asn Val Arg Lys Phe Cys Asp Thr Pro Arg Val
                        485                 490                 495
```

```
Ser Ser Pro His Ala Arg Ala Leu Ala His Tyr Asp Asn Ile Val Cys
        500                 505                 510

Gln Asp Asp Pro Ser Ala Pro His Lys Ile Gln Asp Pro Leu Lys Ser
            515                 520                 525

Arg Leu Lys Glu Glu Gly Ser Phe Asn Ile Gln Asn Ser Met Ser Pro
        530                 535                 540

Lys Leu Glu Gly Gly Lys Gly Asp Gln Asp Asp Leu Gly Val Asn Cys
545                 550                 555                 560

Leu Gln Asn Asn Leu Thr
                565
```

```
<210> SEQ ID NO 17
<211> LENGTH: 20
<212> TYPE: DNA
<213> ORGANISM: Artificial
<220> FEATURE:
<223> OTHER INFORMATION: T3 primer

<400> SEQUENCE: 17
aattaaccct cactaaaggg                                              20

<210> SEQ ID NO 18
<211> LENGTH: 19
<212> TYPE: DNA
<213> ORGANISM: Artificial
<220> FEATURE:
<223> OTHER INFORMATION: T7 primer

<400> SEQUENCE: 18
taatacgact cactatagg                                               19

<210> SEQ ID NO 19
<211> LENGTH: 20
<212> TYPE: DNA
<213> ORGANISM: Artificial
<220> FEATURE:
<223> OTHER INFORMATION: canis RT primer sense

<400> SEQUENCE: 19
aagttactgt cacaacggcg                                              20

<210> SEQ ID NO 20
<211> LENGTH: 20
<212> TYPE: DNA
<213> ORGANISM: Artificial
<220> FEATURE:
<223> OTHER INFORMATION: canis RT primer antisense

<400> SEQUENCE: 20
tcatcatgaa gagcaggagc                                              20

<210> SEQ ID NO 21
<211> LENGTH: 21
<212> TYPE: DNA
<213> ORGANISM: Artificial
<220> FEATURE:
<223> OTHER INFORMATION: human RT primer sense

<400> SEQUENCE: 21
aagttactgt cacaatggcg g                                            21

<210> SEQ ID NO 22
<211> LENGTH: 20
```

```
<212> TYPE: DNA
<213> ORGANISM: Artificial
<220> FEATURE:
<223> OTHER INFORMATION: human RT primer antisense

<400> SEQUENCE: 22
tcatcatgaa gagcaggagc                                            20

<210> SEQ ID NO 23
<211> LENGTH: 20
<212> TYPE: DNA
<213> ORGANISM: Artificial
<220> FEATURE:
<223> OTHER INFORMATION: mouse RT primer sense

<400> SEQUENCE: 23
gagttactgt cacaacggcg                                            20

<210> SEQ ID NO 24
<211> LENGTH: 20
<212> TYPE: DNA
<213> ORGANISM: Artificial
<220> FEATURE:
<223> OTHER INFORMATION: mouse RT primer antisense

<400> SEQUENCE: 24
tcatcatgaa caggaggaga                                            20

<210> SEQ ID NO 25
<211> LENGTH: 18
<212> TYPE: DNA
<213> ORGANISM: Artificial
<220> FEATURE:
<223> OTHER INFORMATION: GAPDH primer

<400> SEQUENCE: 25
gggctgcttt taactctg                                              18

<210> SEQ ID NO 26
<211> LENGTH: 18
<212> TYPE: DNA
<213> ORGANISM: Artificial
<220> FEATURE:
<223> OTHER INFORMATION: GAPDH primer

<400> SEQUENCE: 26
ccaggaaatg agcttgac                                              18

<210> SEQ ID NO 27
<211> LENGTH: 20
<212> TYPE: DNA
<213> ORGANISM: Artificial
<220> FEATURE:
<223> OTHER INFORMATION: GAPDH primer

<400> SEQUENCE: 27
cttcaccacc atggagaagg                                            20

<210> SEQ ID NO 28
<211> LENGTH: 20
<212> TYPE: DNA
<213> ORGANISM: Artificial
<220> FEATURE:
<223> OTHER INFORMATION: GAPDH primer

<400> SEQUENCE: 28
```

```
tgaagtcgca ggagacaacc                                               20

<210> SEQ ID NO 29
<211> LENGTH: 51
<212> TYPE: DNA
<213> ORGANISM: Artificial
<220> FEATURE:
<223> OTHER INFORMATION: homo CSPG5 kpn clo

<400> SEQUENCE: 29
ggtaccatgg ggcgagccgg gggcgggggc ccgggccggg ggccgccgcc a             51

<210> SEQ ID NO 30
<211> LENGTH: 49
<212> TYPE: DNA
<213> ORGANISM: Artificial
<220> FEATURE:
<223> OTHER INFORMATION: homocspg ecoRI clo

<400> SEQUENCE: 30
gaattcttag gttaaattat tctgaagaca gttcacatcc aagtcagcc               49

<210> SEQ ID NO 31
<211> LENGTH: 36
<212> TYPE: DNA
<213> ORGANISM: Artificial
<220> FEATURE:
<223> OTHER INFORMATION: primer

<400> SEQUENCE: 31
gaattcgcac atcacctgga agtcggtgat gatgga                             36

<210> SEQ ID NO 32
<211> LENGTH: 1998
<212> TYPE: DNA
<213> ORGANISM: Artificial
<220> FEATURE:
<223> OTHER INFORMATION: Fc fusion protein
<220> FEATURE:
<221> NAME/KEY: CDS
<222> LOCATION: (1)..(1998)
<223> OTHER INFORMATION:

<400> SEQUENCE: 32 acc acg aag ctt gcc gcc acc atg ggg cga gcc ggg ggc ggg ggc ccg     48
Thr Thr Lys Leu Ala Ala Thr Met Gly Arg Ala Gly Gly Gly Gly Pro
1               5                   10                  15 ggc cgg ggg ccg ccg cca ctg ctg ctg ttt ctg ggg gcc gcg ctg gtc     96
Gly Arg Gly Pro Pro Pro Leu Leu Leu Phe Leu Gly Ala Ala Leu Val
            20                  25                  30 ctg gcc tct ggg gcc gtg ccg gcg cgt gag gcg ggc agc gcg gtt gag    144
Leu Ala Ser Gly Ala Val Pro Ala Arg Glu Ala Gly Ser Ala Val Glu
        35                  40                  45 gcc gaa gag ctg gtg aag ggc agc ccg gcg tgg gag ccg cct gcc aac    192
Ala Glu Glu Leu Val Lys Gly Ser Pro Ala Trp Glu Pro Pro Ala Asn
    50                  55                  60 gac acg cgg gaa gaa gcc ggc cca cca gcg gct ggg gaa gat gag gcg    240
Asp Thr Arg Glu Glu Ala Gly Pro Pro Ala Ala Gly Glu Asp Glu Ala
65                  70                  75                  80 tcg tgg acg gcg ccc ggt ggc gag ctg gcc ggg cca gaa gag gtg ctg    288
Ser Trp Thr Ala Pro Gly Gly Glu Leu Ala Gly Pro Glu Glu Val Leu
                85                  90                  95 cag gag tcg gct gcg gtg acc ggc acc gcc tgg ctg gaa gct gac agc    336
Gln Glu Ser Ala Ala Val Thr Gly Thr Ala Trp Leu Glu Ala Asp Ser
            100                 105                 110
```

| | | |
|---|---|---|
| cca ggc ctg gga gga gtg acc gca gag gcg ggc agc ggc gat gcc cag<br>Pro Gly Leu Gly Gly Val Thr Ala Glu Ala Gly Ser Gly Asp Ala Gln<br>           115                    120                    125 | 384 |
| gcc ctt cca gct acg ctc cag gct ccc cac gag gtc ctc ggg cag tca<br>Ala Leu Pro Ala Thr Leu Gln Ala Pro His Glu Val Leu Gly Gln Ser<br>130                    135                    140 | 432 |
| atc atg ccc cct gcc att cct gag gct aca gag gcc agc ggg cca ccc<br>Ile Met Pro Pro Ala Ile Pro Glu Ala Thr Glu Ala Ser Gly Pro Pro<br>145                  150                  155                160 | 480 |
| tcc ccc acc ccc ggc gac aag ctg agc cca gct tct gaa ctc ccc aag<br>Ser Pro Thr Pro Gly Asp Lys Leu Ser Pro Ala Ser Glu Leu Pro Lys<br>           165                    170                    175 | 528 |
| gag agc ccc ttg gag gtt tgg ctg aac ctg ggg ggc agc aca ccc gac<br>Glu Ser Pro Leu Glu Val Trp Leu Asn Leu Gly Gly Ser Thr Pro Asp<br>                  180                    185                  190 | 576 |
| cct caa ggg cca gag ctg act tac cca ttt cag ggc acc ctg gag ccc<br>Pro Gln Gly Pro Glu Leu Thr Tyr Pro Phe Gln Gly Thr Leu Glu Pro<br>           195                    200                    205 | 624 |
| caa ccg gca tca gat atc att gac atc gac tac ttc gaa gga ctg gat<br>Gln Pro Ala Ser Asp Ile Ile Asp Ile Asp Tyr Phe Glu Gly Leu Asp<br>210                  215                    220 | 672 |
| ggt gag ggt cgt ggc gca gat ctg ggg agc ttc cca ggg tca cca gga<br>Gly Glu Gly Arg Gly Ala Asp Leu Gly Ser Phe Pro Gly Ser Pro Gly<br>225                  230                  235                240 | 720 |
| acc tca gag aac cac cct gat act gag gga gag acc cct tcc tgg agc<br>Thr Ser Glu Asn His Pro Asp Thr Glu Gly Glu Thr Pro Ser Trp Ser<br>                  245                    250                  255 | 768 |
| ctg ctt gac tta tac gat gat ttc acc ccc ttc gat gaa tct gat ttc<br>Leu Leu Asp Leu Tyr Asp Asp Phe Thr Pro Phe Asp Glu Ser Asp Phe<br>          260                    265                    270 | 816 |
| tac ccc acc aca tcc ttt tat gat gac ttg gat gaa gag gag gag gaa<br>Tyr Pro Thr Thr Ser Phe Tyr Asp Asp Leu Asp Glu Glu Glu Glu Glu<br>           275                    280                    285 | 864 |
| gag gag gat gac aaa gat gca gta gga ggt gga gac cta gaa gat gaa<br>Glu Glu Asp Asp Lys Asp Ala Val Gly Gly Gly Asp Leu Glu Asp Glu<br>290                  295                  300 | 912 |
| aat gag ctt cta gtg ccc act ggg aag cct ggt ctg ggg ccc ggg aca<br>Asn Glu Leu Leu Val Pro Thr Gly Lys Pro Gly Leu Gly Pro Gly Thr<br>305                  310                  315                320 | 960 |
| ggc cag ccc acc agt cgg tgg cat gct gtc cct cca cag cac act ctg<br>Gly Gln Pro Thr Ser Arg Trp His Ala Val Pro Pro Gln His Thr Leu<br>                  325                    330                  335 | 1008 |
| ggg tcg gtc ccc ggc agc agc atc gcc ctc agg ccc cgc cca gga gag<br>Gly Ser Val Pro Gly Ser Ser Ile Ala Leu Arg Pro Arg Pro Gly Glu<br>           340                    345                    350 | 1056 |
| cca ggc agg gac ttg gcc tcc agt gaa aat ggc act gag tgc cgc agt<br>Pro Gly Arg Asp Leu Ala Ser Ser Glu Asn Gly Thr Glu Cys Arg Ser<br>           355                    360                    365 | 1104 |
| ggc ttt gtg cgg cat aac ggc tcc tgc cgg tca gtg tgc gac ctc ttc<br>Gly Phe Val Arg His Asn Gly Ser Cys Arg Ser Val Cys Asp Leu Phe<br>370                  375                    380 | 1152 |
| cca agt tac tgt cac aat ggc ggc cag tgc tac ctg gtg gag aac ata<br>Pro Ser Tyr Cys His Asn Gly Gly Gln Cys Tyr Leu Val Glu Asn Ile<br>385                  390                  395                400 | 1200 |
| ggg gcc ttc tgc agg tgc aac acg cag gac tac atc tgg cac aag ggg<br>Gly Ala Phe Cys Arg Cys Asn Thr Gln Asp Tyr Ile Trp His Lys Gly<br>                  405                    410                  415 | 1248 |
| atg cgc tgc gag tcc atc atc acc gac ttc cag ccg aat tct gca gat<br>Met Arg Cys Glu Ser Ile Ile Thr Asp Phe Gln Pro Asn Ser Ala Asp | 1296 |

-continued

```
                    420                 425                 430
atc ccc aga ggg ccc aca atc aag ccc tgt cct cca tgc aaa tgc cca      1344
Ile Pro Arg Gly Pro Thr Ile Lys Pro Cys Pro Pro Cys Lys Cys Pro
            435                 440                 445 gca cct aac ctc ttg ggt gga cca tcc gtc ttc atc ttc cct cca aag      1392
Ala Pro Asn Leu Leu Gly Gly Pro Ser Val Phe Ile Phe Pro Pro Lys
450                 455                 460 atc aag gat gta ctc atg atc tcc ctg agc ccc ata gtc aca tgt gtg      1440
Ile Lys Asp Val Leu Met Ile Ser Leu Ser Pro Ile Val Thr Cys Val
465                 470                 475                 480 gtg gtg gat gtg agc gag gat gac cca gat gtc cag atc agc tgg ttt      1488
Val Val Asp Val Ser Glu Asp Asp Pro Asp Val Gln Ile Ser Trp Phe
                485                 490                 495 gtg aac aac gtg gaa gta cac aca gct cag aca caa acc cat aga gag      1536
Val Asn Asn Val Glu Val His Thr Ala Gln Thr Gln Thr His Arg Glu
            500                 505                 510 gat tac aac agt act ctc cgg gtg gtc agt gcc ctc ccc atc cag cac      1584
Asp Tyr Asn Ser Thr Leu Arg Val Val Ser Ala Leu Pro Ile Gln His
            515                 520                 525 cag gac tgg atg agt ggc aag gag ttc aaa tgc aag gtc aac aac aaa      1632
Gln Asp Trp Met Ser Gly Lys Glu Phe Lys Cys Lys Val Asn Asn Lys
530                 535                 540 gac ctc cca gcg ccc atc gag aga acc atc tca aaa ccc aaa ggg tca      1680
Asp Leu Pro Ala Pro Ile Glu Arg Thr Ile Ser Lys Pro Lys Gly Ser
545                 550                 555                 560 gta aga gct cca cag gta tat gtc ttg cct cca cca gaa gaa gag atg      1728
Val Arg Ala Pro Gln Val Tyr Val Leu Pro Pro Pro Glu Glu Glu Met
                565                 570                 575 act aag aaa cag gtc act ctg acc tgc atg gtc aca gac ttc atg cct      1776
Thr Lys Lys Gln Val Thr Leu Thr Cys Met Val Thr Asp Phe Met Pro
            580                 585                 590 gaa gac att tac gtg gag tgg acc aac aac ggg aaa aca gag cta aac      1824
Glu Asp Ile Tyr Val Glu Trp Thr Asn Asn Gly Lys Thr Glu Leu Asn
            595                 600                 605 tac aag aac act gaa cca gtc ctg gac tct gat ggt tct tac ttc atg      1872
Tyr Lys Asn Thr Glu Pro Val Leu Asp Ser Asp Gly Ser Tyr Phe Met
610                 615                 620 tac agc aag ctg aga gtg gaa aag aag aac tgg gtg gaa aga aat agc      1920
Tyr Ser Lys Leu Arg Val Glu Lys Lys Asn Trp Val Glu Arg Asn Ser
625                 630                 635                 640 tac tcc tgt tca gtg gtc cac gag ggt ctg cac aat cac cac acg act      1968
Tyr Ser Cys Ser Val Val His Glu Gly Leu His Asn His His Thr Thr
                645                 650                 655 aag agc ttc tcc cgg act ccg ggt aaa tga                              1998
Lys Ser Phe Ser Arg Thr Pro Gly Lys
            660                 665
```

<210> SEQ ID NO 33
<211> LENGTH: 665
<212> TYPE: PRT
<213> ORGANISM: Artificial
<220> FEATURE:
<223> OTHER INFORMATION: Fc fusion protein

<400> SEQUENCE: 33

```
Thr Thr Lys Leu Ala Ala Thr Met Gly Arg Ala Gly Gly Gly Gly Pro
1               5                   10                  15

Gly Arg Gly Pro Pro Pro Leu Leu Leu Phe Leu Gly Ala Ala Leu Val
            20                  25                  30

Leu Ala Ser Gly Ala Val Pro Ala Arg Glu Ala Gly Ser Ala Val Glu
```

```
                35                  40                  45
Ala Glu Glu Leu Val Lys Gly Ser Pro Ala Trp Pro Pro Ala Asn
 50                  55                  60

Asp Thr Arg Glu Glu Ala Gly Pro Pro Ala Ala Gly Glu Asp Glu Ala
 65                  70                  75                  80

Ser Trp Thr Ala Pro Gly Gly Glu Leu Ala Gly Pro Glu Glu Val Leu
                 85                  90                  95

Gln Glu Ser Ala Ala Val Thr Gly Thr Ala Trp Leu Gly Ala Asp Ser
                100                 105                 110

Pro Gly Leu Gly Gly Val Thr Ala Glu Ala Gly Ser Gly Asp Ala Gln
                115                 120                 125

Ala Leu Pro Ala Thr Leu Gln Ala Pro His Glu Val Leu Gly Gln Ser
130                 135                 140

Ile Met Pro Pro Ala Ile Pro Glu Ala Thr Glu Ala Ser Gly Pro Pro
145                 150                 155                 160

Ser Pro Thr Pro Gly Asp Lys Leu Ser Pro Ala Ser Glu Leu Pro Lys
                165                 170                 175

Glu Ser Pro Leu Glu Val Trp Leu Asn Leu Gly Gly Ser Thr Pro Asp
                180                 185                 190

Pro Gln Gly Pro Glu Leu Thr Tyr Pro Phe Gln Gly Thr Leu Glu Pro
                195                 200                 205

Gln Pro Ala Ser Asp Ile Ile Asp Ile Asp Tyr Phe Glu Gly Leu Asp
210                 215                 220

Gly Glu Gly Arg Gly Ala Asp Leu Gly Ser Phe Pro Gly Ser Pro Gly
225                 230                 235                 240

Thr Ser Glu Asn His Pro Asp Thr Glu Gly Glu Thr Pro Ser Trp Ser
                245                 250                 255

Leu Leu Asp Leu Tyr Asp Asp Phe Thr Pro Phe Asp Glu Ser Asp Phe
                260                 265                 270

Tyr Pro Thr Thr Ser Phe Tyr Asp Asp Leu Asp Glu Glu Glu Glu Glu
                275                 280                 285

Glu Glu Asp Asp Lys Asp Ala Val Gly Gly Gly Asp Leu Glu Asp Glu
                290                 295                 300

Asn Glu Leu Leu Val Pro Thr Gly Lys Pro Gly Leu Gly Pro Gly Thr
305                 310                 315                 320

Gly Gln Pro Thr Ser Arg Trp His Ala Val Pro Pro Gln His Thr Leu
                325                 330                 335

Gly Ser Val Pro Gly Ser Ser Ile Ala Leu Arg Pro Arg Pro Gly Glu
                340                 345                 350

Pro Gly Arg Asp Leu Ala Ser Ser Glu Asn Gly Thr Glu Cys Arg Ser
                355                 360                 365

Gly Phe Val Arg His Asn Gly Ser Cys Arg Ser Val Cys Asp Leu Phe
                370                 375                 380

Pro Ser Tyr Cys His Asn Gly Gly Gln Cys Tyr Leu Val Glu Asn Ile
385                 390                 395                 400

Gly Ala Phe Cys Arg Cys Asn Thr Gln Asp Tyr Ile Trp His Lys Gly
                405                 410                 415

Met Arg Cys Glu Ser Ile Ile Thr Asp Phe Gln Pro Asn Ser Ala Asp
                420                 425                 430

Ile Pro Arg Gly Pro Thr Ile Lys Pro Cys Pro Pro Cys Lys Cys Pro
                435                 440                 445

Ala Pro Asn Leu Leu Gly Gly Pro Ser Val Phe Ile Phe Pro Pro Lys
450                 455                 460
```

-continued

```
Ile Lys Asp Val Leu Met Ile Ser Leu Ser Pro Ile Val Thr Cys Val
465                 470                 475                 480

Val Val Asp Val Ser Glu Asp Pro Asp Val Gln Ile Ser Trp Phe
                485                 490                 495

Val Asn Asn Val Glu Val His Thr Ala Gln Thr Gln Thr His Arg Glu
            500                 505                 510

Asp Tyr Asn Ser Thr Leu Arg Val Val Ser Ala Leu Pro Ile Gln His
        515                 520                 525

Gln Asp Trp Met Ser Gly Lys Glu Phe Lys Cys Lys Val Asn Asn Lys
    530                 535                 540

Asp Leu Pro Ala Pro Ile Glu Arg Thr Ile Ser Lys Pro Lys Gly Ser
545                 550                 555                 560

Val Arg Ala Pro Gln Val Tyr Val Leu Pro Pro Pro Glu Glu Glu Met
                565                 570                 575

Thr Lys Lys Gln Val Thr Leu Thr Cys Met Val Thr Asp Phe Met Pro
            580                 585                 590

Glu Asp Ile Tyr Val Glu Trp Thr Asn Asn Gly Lys Thr Glu Leu Asn
        595                 600                 605

Tyr Lys Asn Thr Glu Pro Val Leu Asp Ser Asp Gly Ser Tyr Phe Met
    610                 615                 620

Tyr Ser Lys Leu Arg Val Glu Lys Lys Asn Trp Val Glu Arg Asn Ser
625                 630                 635                 640

Tyr Ser Cys Ser Val Val His Glu Gly Leu His Asn His His Thr Thr
                645                 650                 655

Lys Ser Phe Ser Arg Thr Pro Gly Lys
                660                 665
```

PHARMACEUTICAL COMPOSITION FOR TREATING AND/OR PREVENTING CANCER

TECHNICAL FIELD

The present invention relates to novel medicinal use of an antibody against CSPG5 protein or a fragment thereof as e.g., a therapeutic and/or prophylactic agent for cancer.

BACKGROUND ART

Cancer is a disease occupying the leading position of cause of death. Therapies presently employed are primarily based on a surgical therapy in combination with a radiation therapy and a chemotherapy. Despite of recent development of new surgical techniques and finding of new anticancer drugs, treatment results of cancers except some cancers have not yet likely been improved at present. With the advancement of molecular biology and cancer immunology, antibodies that specifically react with cancers, cancer antigens recognized by cytotoxic T cells, genes encoding cancer antigens and the like have been identified. Thus, development of specific cancer treatments targeting cancer antigens has been desired.

In the cancer therapy, it is desirable that the peptides (including polypeptides) to be recognized as antigens are rarely present in normal cells and present specifically in cancer cells in order to reduce side effects. In 1991, Boon et al. of the Ludwig Laboratory in Belgium isolated human melanoma antigen MAGE1, recognized by CD8 positive T cells, by cDNA expression cloning method using an autologous tumor cell line and tumor-reactive T cells (Non Patent Literature 1). Subsequently, SEREX (serological identification of antigens by recombinant expression cloning) method was reported, which is a method of identifying a cancer antigen recognized by an antibody produced in response to autologous cancer in the body of a patient, by using a gene expression cloning method (Patent Literature 1, Non Patent Literature 2). Several cancer antigens, which are rarely expressed in normal cells and specifically expressed in cancer cells, have been isolated by this method (Non Patent Literature 3). Further, a cell therapy, which uses immune cells targeting a part of the amino acid sequence of such a cancer antigen and specifically reacting with the cancer antigen, and a cancer-specific immunotherapy such as a vaccine containing a cancer antigen, are carried out in clinical trials.

In the meantime, various types of antibody medicines for treating cancer, targeting a specific antigen protein on cancer cells have been known in the world. Most of the target antigen proteins provide certain levels of medicinal effects as a cancer-specific therapeutic agent and attract attention; however they express also on a plurality of normal cells. Because of this, side effects are seriously concerned since not only cancer cells but also normal cells are damaged as a result of administration of antibodies. Accordingly, it is expected that a therapy with an antibody medicine having fewer side effects can be realized, if an antigen, which is specifically expressed only on the cancer cell surfaces and not expressed on normal cells, can be identified and an antibody targeting the antigen can be used as a medicine.

CITATION LIST

Patent Literature

Patent Literature 1: U.S. Pat. No. 5,698,396

Non Patent Literature

Non Patent Literature 1: Bruggen P. et al., Science, 254: 1643-1647 (1991)
Non Patent Literature 2: Proc. Natl. Acad. Sci. USA, 92: 11810-11813 (1995)
Non Patent Literature 3: Int. J. Cancer, 72: 965-971 (1997)

SUMMARY OF INVENTION

Technical Problem

An object of the present invention is to identify a cancer antigen protein specifically expressed on the surface of cancer cells and provide use of an antibody targeting the cancer antigen protein as a therapeutic and/or prophylactic agent for cancer.

Solution to Problem

The present inventors isolated an antigen specifically expressed in cancer by SEREX method using cDNA library derived from a canine testicular tissue and the serum of a breast cancer-bearing dog, and then obtained cDNA encoding CSPG5 protein. CSPG5 protein can bind to antibodies present in the sera derived from various cancer-bearing living organisms. The present inventors also found that CSPG5 protein is specifically expressed in breast cancer, lung cancer, brain tumor, leukemia, malignant lymphoma, adenocarcinoma, mastocytoma, squamous cell carcinoma, melanoma or neuroblastoma cells; and that a part of CSPG5 protein is specifically expressed on the surface of these cancer cells. CSPG5 (Chondroitin Sulfate Proteoglycan 5) protein is type I transmembrane protein and one of the neuregulin family proteins. It is also reported that CSPG5 protein binds to ErbB3 protein to serve as a growth factor; and that expression of CSPG5 protein increases in ovarian cancer having a mutation of BRCA1 protein (Kinugasa, Y., et al., 2004, Biochem. Biophys. Res. Commun., 321: 1045; Press, J. Z., et al., 2010, Neoplasia., 12 (12): 993-1002). It is further known that CSPG5 protein is highly expressed in tissues of the nervous system, such as retinal ganglion cells, purkinje cells and hippocampus, and serves as a proliferation/differentiation factor of nerve cells involved in elongation of nerve axon process (Yasuda, Y. et al., 1998, Neurosci. Res., 32: 313; Aono, S., et al., 2006, J. Neurosci. Res., 83: 110; Nakanishi, K., et al., 2006, J. Biol. Chem., 281: 24970). However, there have been no reports that CSPG5 protein has an immunity inducing activity against cancer cells and thus is useful for treating and preventing cancer.

Also, the inventors prepared CSPG5 protein molecules consisting of amino acid sequences represented by SEQ ID NOs: 2, 4, 6, 8, 10, 12, 14 and 16 based on the obtained canine CSPG5 gene and its homologous genes of human, cat and mouse and antibodies against these CSPG5 protein molecules. Then, they found that an antibody against the portion of each of these CSPG5 protein molecules expressed on the surfaces of individual cancer cells, in other words, the extracellular region thereof, damages the cancer cell expressing CSPG5 protein. Based on the finding, the present invention was accomplished.

Accordingly, the present invention has the following features.

(1) A pharmaceutical composition for treating and/or preventing cancer, comprising an antibody or a fragment thereof having immunological reactivity with CSPG5 protein or a fragment thereof consisting of at least 7 or more consecutive amino acid residues, as an active ingredient.
(2) The pharmaceutical composition according to (1), wherein the CSPG5 protein consists of any one of amino acid sequences represented by SEQ ID NOs: 8, 4, 6, 10 and 12, or an amino acid sequence having an amino acid identity of 80% or more to the amino acid sequence.
(3) The pharmaceutical composition according to (1) or (2), wherein the cancer is leukemia or malignant lymphoma.
(4) The pharmaceutical composition according to any one of (1) to (3), wherein the antibody is a monoclonal antibody or a polyclonal antibody.
(5) The pharmaceutical composition according to any one of (1) to (4), wherein the antibody is a human antibody, a humanized antibody, a chimeric antibody, a single-chain antibody or a bispecific antibody.

The specification incorporates the disclosure of JP Patent Application No. 2015-093640 to which the present application claims the priority.

Advantageous Effects of Invention

The antibody against CSPG5 protein used in the present invention damages cancer cells. Accordingly, the antibody against CSPG5 protein is useful for treatment and/or prevention of cancer.

DESCRIPTION OF EMBODIMENTS

Figure 1:
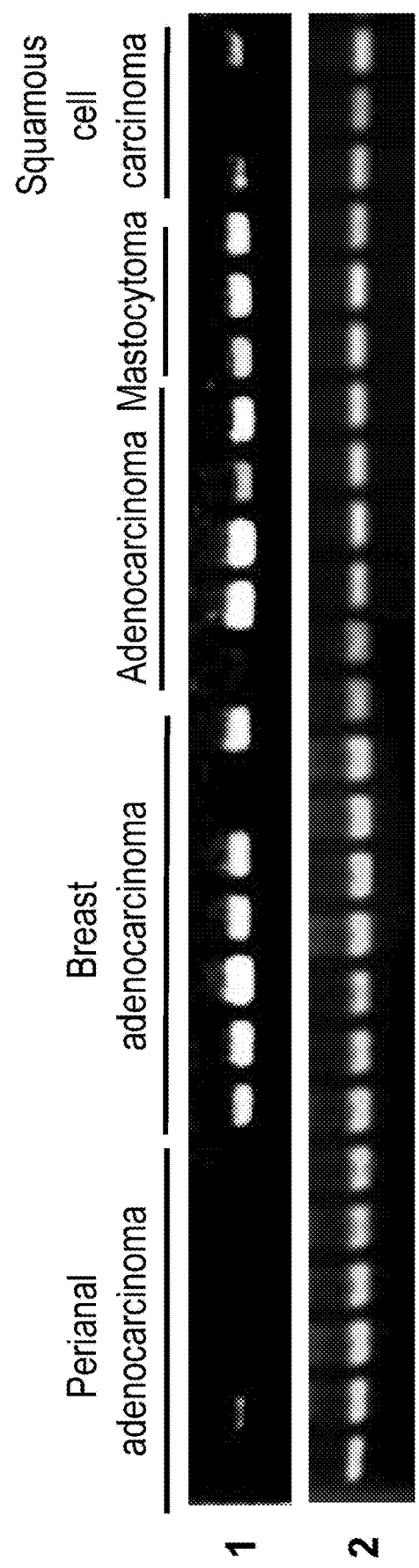
FIG. 1 shows expression patterns of identified CSPG5 gene in canine tumor tissues or cancer cell lines. In the figure, reference number 1 shows expression patterns of canine CSPG5 gene in individual canine tissues and cell lines; and reference number 2 shows expression patterns of canine GAPDH gene in individual canine tissues and cell lines.

The antitumor activity of an antibody against a polypeptide consisting of the amino acid sequence represented by SEQ ID NO: 2, 4, 6, 8, 10, 12, 14 or 16, used in the present invention, can be evaluated by checking, in vivo suppression of tumor growth in a cancer-bearing animal or by checking, whether or not the antibody exerts in vitro cytotoxic activity against tumor cells expressing the polypeptide via immune cells or a complement, as described later.

The nucleotide sequence of a polynucleotide encoding the protein consisting of the amino acid sequence represented by SEQ ID NO: 2, 4, 6, 8, 10, 12, 14 or 16 is represented by SEQ ID NO: 1, 3, 5, 7, 9, 11, 13 or 15, respectively.

The amino acid sequence represented by SEQ ID NO: 2 in the sequence listing disclosed in the present invention is an amino acid sequence of CSPG5 protein isolated as a polypeptide binding to an antibody specifically present in the serum derived from a cancer-bearing dog by the SEREX method using a cDNA library derived from a canine testicular tissue and the serum of a breast cancer-bearing dog; the amino acid sequences represented by SEQ ID NOs: 4, 6, 8, 10 and 12 are isolated as human homologs of the polypeptide; the amino acid sequence represented by SEQ ID NO: 14 is isolated as a cat homolog of the polypeptide; and the amino acid sequence represented by SEQ ID NO: 16 is isolated as a mouse homolog of the polypeptide (see, Example 1 described later).

It has been known from the amino acid sequence that CSPG5 protein is type I transmembrane protein, and that the extracellular region predicted from its sequence is expressed on the surface of nerve cells. Owing to the present application, it was confirmed that the extracellular region of CSPG5 protein is actually expressed (present) on the surface of various types of cancer cells. In the present invention, an antibody binding to the extracellular region of CSPG5 protein on a cancer cell or binding to a polypeptide having an amino acid identity of 80% or more, preferably 85% or more, more preferably 90% or more, further preferably 95% or more, 97% or more, 98% or more or 99% or more with the amino acid sequence of the extracellular region, is preferably used.

The antibody against CSPG5 protein used in the present invention may be of any type of antibody as long as it can exert an antitumor activity. Examples of the antibody include a monoclonal antibody, a polyclonal antibody, a synthetic antibody, a multi-specific antibody, a human antibody, a humanized antibody, a chimeric antibody, a single-chain antibody (scFV) and an antibody fragment (for example, Fab, F(ab')$_2$, Fv). These antibodies and fragments thereof can be prepared by methods known to those skilled in the art. In the present invention, an antibody capable of specifically binding to CSPG5 protein is desirable and a monoclonal antibody is preferable; however, a polyclonal antibody may be used as long as homogeneous antibodies can be stably produced. When the subject is a human, a human antibody or a humanized antibody is desirable in order to avoid or suppress a rejection reaction.

The phrase "specifically binding to CSPG5 protein" used herein means binding specifically to CSPG5 protein and substantially not binding to proteins except CSPG5 protein.

The subject, which is a target for treatment and/or prevention of cancer by the present invention, is a mammal such as humans, pet animals, domestic animals and animals for competitive use, preferably a human.

Preparation of an antigen, preparation of an antibody and a pharmaceutical composition according to the present invention is described below.

<Preparation of Antigen for Preparing Antibody>

The protein or a fragment thereof used as a sensitizing antigen for obtaining an antibody against CSPG5 protein (anti-CSPG5 antibody) in the present invention may be derived from e.g., humans, dogs, cats, mice, rats, cows, horses and chickens, and the animal species from which the protein or a fragment thereof is derived is not limited thereto. The protein or a fragment thereof is preferably selected in consideration of compatibility to a parent cell to be used in cell fusion. Generally, the protein derived from a mammal is preferable and particularly the protein derived from a human is preferable. For example, if the CSPG5 protein is human CSPG5 protein, human CSPG5 protein, a partial polypeptide thereof, a cell expressing the human CSPG5 protein, and the like can be used.

The amino acid sequences and nucleotide sequences of CSPG5 protein and homologs thereof can be obtained by using, for example, GenBank (NCBI of the United State) and by using an algorithm such as BLAST and FASTA (Karlin and Altschul, Proc. Natl. Acad. Sci. USA, 90: 5873-5877, 1993; Altschul et al., Nucleic Acids Res. 25: 3389-3402, 1997).

For example, if human CSPG5 protein is used as a basis, a nucleotide sequence (SEQ ID NO: 3, 5, 7, 9 or 11) encoding the human CSPG5 protein and a nucleic acid having a nucleotide identity of 70% to 100%, preferably 80% to 100%, more preferably 90% to 100%, further preferably 95% to 100% (for example 97% to 100%, 98% to 100%, 99% to 100% or 99.5% to 100%) to the nucleotide sequence are used as a target. Also, the amino acid sequence (SEQ ID NO: 4, 6, 8, 10 or 12) of the human CSPG5 protein and a polypeptide having an amino acid identity of 70% to 100%, preferably 80% to 100%, more preferably 90% to 100%, or further preferably 95% to 100% (for example, 97% to 100%, 98% to 100%, 99% to 100% or 99.5% to 100%) to the amino acid sequence are used as a target. The term "nucleotide identity" used herein refers to the percentage (%) of the number of identical nucleotides relative to the total number of nucleotides when two nucleotide sequences are aligned such that they have a maximum degree of similarity by appropriately introducing gap(s). Similarly, the term "amino acid identity" refers to the percentage (%) of the number of identical amino acids relative to the total number of amino acids when two amino acid sequences are aligned such that they have a maximum degree of similarity by appropriately introducing gap(s).

The fragment of CSPG5 protein is specified to have a length equal to or longer than the amino acid length of an epitope (antigen determinant) and less than the full length of the protein. The epitope is a polypeptide fragment which is a minimum unit recognized by an antibody in a mammal, preferably a human and has antigenicity or immunogenicity, and includes amino acid sequences having a length of about 7 to 12 amino acids, for example, 8 to 11 amino acids.

The human CSPG5 protein and a polypeptide containing a partial peptide thereof can be synthesized, for example, by a chemical synthesis method such as Fmoc method (fluorenylmethyloxycarbonyl method) and tBoc method (t-butyloxycarbonyl method) (Biochemical Experiment Course 1, Chemistry of Protein IV, Chemical Modification and Synthesis of Peptide, edited by the Japan Biochemical Society, Tokyo Kagaku Dojin (Japan), 1981) or synthesized in accordance with a routine method using a commercially available peptide synthesizer. Alternatively, a desired polypeptide can be obtained by genetic engineering technique known in the art (e.g., Green, M. R. and Sambrook, J., 2012, Molecular Cloning: A Laboratory Manual 4th Ed., Cold Spring Harbor Laboratory Press, Cold Spring Harbor, N.Y., Ausubel et al., Short Protocols in Molecular Biology, third edition, A compendium of Methods from Current Protocols in Molecular Biology (1995), John Wiley & Sons); more specifically by preparing a polynucleotide encoding the polypeptide, integrating the polynucleotide into an expression vector, introducing the vector into a host cell and allowing the host cell to produce a polypeptide.

The polynucleotide encoding the polypeptide can be easily prepared by a routine method using a genetic engineering technique known in the art or a commercially available nucleic acid synthesizer. For example, DNA having the nucleotide sequence of SEQ ID NO: 3 can be prepared by carrying out PCR using a human chromosome DNA library or a human cDNA library as a template and a pair of primers designed so as to amplify the nucleotide sequence represented by SEQ ID NO: 3. The reaction conditions of the PCR can be appropriately defined; for example, the reaction conditions include a condition where using a heat-resistant DNA polymerase (for example, Taq polymerase) and a $Mg^{2+}$-containing PCR buffer, a cycle consisting of a denaturation reaction at 94° C. for 30 seconds, an annealing reaction at 55° C. for 30 seconds to 1 minute and an elongation reaction at 72° C. for 2 minutes, for example, is repeated 30 times and then carrying out a reaction at 72° C. for 7 minutes; however, the reaction conditions are not particularly limited thereto. The PCR method and conditions are described, for example in Ausubel et al., Short Protocols in Molecular Biology, third edition, A compendium of Methods from Current Protocols in Molecular Biology (1995), John Wiley & Sons (particularly Chapter 15).

A desired DNA can be isolated by preparing an appropriate probe and primers based on information of the nucleotide sequence represented by SEQ ID NO: 1, 3, 5, 7, 9, 11, 13 or 15 in the sequence listing of the present application and screening a cDNA library of a human etc. by the probe and primers. The cDNA library is preferably prepared from the cell, organ or tissue expressing a protein consisting of the amino acid sequence represented by SEQ ID NO: 2, 4, 6, 8, 10, 12, 14 or 16. Examples of such a cell or tissue include, but are not limited to, cells or tissues derived from cancers or tumors such as testicles or leukemia, breast cancer, lymphoma, brain tumor, lung cancer, colon cancer, mastocytoma, melanoma and neuroblastoma. The aforementioned operations, such as preparation of the probe or primers, construction of a cDNA library, screening of a cDNA library and cloning of a gene of interest, are known to those skilled in the art and can be carried out in accordance with the method described, for example, in Green, M. R. and Sambrook (described above), Ausbel et al. (described above). From the DNA thus obtained, DNA encoding CSPG5 protein and a partial peptide thereof can be obtained.

As the host cell, any type of cell may be used as long as it can express the above polypeptide. Examples of prokaryotic cells include *Escherichia coli*, and examples of eukaryotic cells include, but not limited to, yeast cells including budding yeast and fission yeast, insect cells such as silkworm cells, *Xenopus* egg cells and mammalian cells such as monkey kidney cells COS1, Chinese hamster ovary cells CHO, human fetal kidney cell line HEK293 and mouse fetal skin cell line NIH3T3.

When a prokaryotic cell is used as a host cell, an expression vector having a replication origin in a prokaryotic cell, a promoter, a ribosome binding site, a multi cloning site, a terminator, a drug resistance gene, an auxotrophic complement gene, and the like is used as the expression vector. Examples of the expression vector for *Escherichia coli* may include pUC system, pBluescriptII, pET expression system and pGEX expression system. The polypeptide encoded by DNA can be expressed in the prokaryotic host cell, by integrating DNA encoding the polypeptide into such an expression vector; transforming a prokaryotic host cell with the vector; and culturing the resultant transformant. At this time, the polypeptide can be expressed as a part of a fusion protein with another protein.

When a eukaryotic cell is used as a host cell, an expression vector for a eukaryotic cell having a promoter, a splicing region, a poly (A) additional site, and the like is used as the expression vector. Examples of such an expression vector may include pKA1, pCDM8, pSVK3, pMSG, pSVL, pBK-CMV, pBK-RSV, EBV vector, pRS, pcDNA3.1 and pYES2. The polypeptide encoded by DNA can be expressed in a eukaryotic host cell, similarly to the above, by integrating DNA encoding the above polypeptide into such an expression vector, transforming the eukaryotic host cell with the vector, and culturing the resultant transformant. The above polypeptide can be expressed as a part of a fusion protein attached with a tag such as a His tag (for example, $(His)_6$ to $(His)_{10}$), a FLAG tag, a myc tag, a HA tag and a GFP, when pIND5-His, pFLAG-CMV-2, pEGFP-N1, pEGFP-C1 or the like is used as the expression vector.

Introduction of an expression vector into a host cell can be carried out by using a method well known in the art, such as an electroporation method, a calcium phosphate method, a liposome method, a DEAE dextran method, microinjection, viral infection, lipofection and binding to a cell membrane penetrating peptide.

For isolation/purification of a desired polypeptide from a host cell, separation operations known in the art can be used in combination. Examples of the separation operations include, but are not limited to, a treatment with a denaturant such as urea or a surfactant, sonication, enzymatic digestion, salting out and solvent fractionation precipitation, dialysis, centrifugation, ultrafiltration, gel filtration, SDS-PAGE, isoelectric point electrophoresis, ion exchange chromatography, hydrophobic chromatography, affinity chromatography and reverse phase chromatography.

<Antibody Structure>

An antibody is a hetero-multimer glycoprotein usually containing at least two heavy chains and two light chains. Four types of immunoglobulins except IgM each are a hetero-tetramer glycoprotein of about 150 kDa primarily constituted of two identical light (L) chains and two identical heavy (H) chains. Typically, each of the light chains is linked to a heavy chain via a single disulfide covalent bond; whereas the number of disulfide bonds between the heavy chains varies depending on the isotypes of immunoglobulins Each of the heavy chains and light chains has also an intra-strand disulfide bond. Each of the heavy chains has a variable domain (VH region) at an end, followed by several constant regions. Each of the light chains has a variable domain (VL region) at an end and a single constant region at the other end. The light-chain variable domain is aligned with the heavy-chain variable domain. The constant region of a light chain is aligned with the first constant region following the heavy-chain variable domain. In the variable domain of the antibody, there are three specific regions called as complementarity determining regions (CDRs), which are variable parts and based on which the antibody has binding specificity. In the variable region, a portion relatively conserved is called as a framework region (FR). Complete heavy chain and light chain variable domains each contain 4 FRs (FR1, FR2, FR3 and FR4 sequentially from the N terminal side) connected via three CDRs. The three CDRs in a heavy chain are called CDRH1, CDRH2 and CDRH3 sequentially from the N terminal side and the CDRs in a light chain are called CDRL1, CDRL2 and CDRL3. CDRH3 is the most important for binding specificity of an antibody to an antigen. The CDRs of each chain are held together in close proximity with each other via FR regions and contribute to formation of an antigen binding site of the antibody in concert with CDRs of the other chain. The constant region does not directly contribute to binding of the antibody to an antigen; however, the constant region has various effector functions, such as involvement in antibody-dependent cell-mediated cytotoxicity (ADCC), phagocytosis via binding to an Fcy receptor, half-life/clearance rate via a neonatal Fc receptor (FcRn), and complement-dependent cytotoxicity (CDC) via C1q component of a complement cascade.

<Preparation of Antibody>

The anti-CSPG5 antibody of the present invention refers to an antibody having immunological reactivity with a full-length CSPG5 protein or a fragment thereof.

The term "immunological reactivity" used herein refers to a property of an antibody binding to CSPG5 antigen, in-vivo. Through such a binding, an action to damage (for example, kill, suppress or induce regression of) a tumor is exerted. More specifically, the type of an antibody used in the present invention is not limited as long as it can bind to CSPG5 protein to damage a tumor such as breast cancer, lung cancer, brain tumor, leukemia, malignant lymphoma, adenocarcinoma, mastocytoma, squamous cell carcinoma, melanoma or neuroblastoma.

Examples of the antibody include a monoclonal antibody, a polyclonal antibody, a genetic recombinant antibody and an antibody fragment (for example, Fab and $F(ab')_2$), as mentioned above. Also the antibody may be any class of an immunoglobulin molecule such as IgG, IgE, IgM, IgA, IgD and IgY or any subclass thereof such as IgG1, IgG2, IgG3, IgG4, IgA1 and IgA2.

The antibody may be further modified with acetylation, formylation, amidation, phosphorylation, pegylation (PEG), or the like as well as glycosylation.

Preparation examples of various antibodies are described below.

(1) Monoclonal Antibody

Examples of the monoclonal antibody include a human monoclonal antibody and an animal (non-human) monoclonal antibody (for example, a mouse monoclonal antibody, a rat monoclonal antibody, a rabbit monoclonal antibody and a chicken monoclonal antibody).

The antibody, in the case of a monoclonal antibody, can be prepared by carrying out immunization in accordance with a general immunization method using a desired antigen (CSPG5 protein herein) or a cell expressing the desired antigen as a sensitizing antigen, fusing thus obtained immune cell with a parent cell known in the art in accordance with a general cell fusion method and screening a monoclonal antibody producing cell (hybridoma) by a general screening method.

First, an animal is immunized with a sensitizing antigen in accordance with a method known in the art. As a general method, a sensitizing antigen is intraperitoneally or subcutaneously injected to a mammal, for example, a mouse. More specifically, a sensitizing antigen, i.e., CSPG5 protein, is diluted or suspended to an appropriate amount of PBS (Phosphate-Buffered Saline), physiological saline, or the like, and if desired, a general adjuvant, for example, Freund's complete adjuvant, is added thereto in an appropriate amount and emulsified. Thereafter, the emulsion is administered to a mammal, for example, a mouse, several times at intervals of 4 to 21 days. An appropriate carrier can be used at the time of immunization with a sensitization antigen. Alternatively, leukemia cell line K562 expressing CSPG5 gene or the like may be administered to an animal (to be immunized) in order to immunize the animal.

After a mammal is immunized as described above and an increase of the level of the desired antibody in the serum is confirmed, immune cells are collected from the mammal and subjected to cell fusion in order to prepare a hybridoma producing a monoclonal antibody. As the preferable immune cells for preparing a hybridoma, particularly splenocytes are mentioned.

Mammalian myeloma cells are used as another parent cells to be fused with the immune cells. As the myeloma cells, various cell lines known in the art such as P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), 5194 (Trowbridge, I. S. J. Exp. Med. (1978) 148, 313-323), 8210 (Galfre, G. et al., Nature (1979) 277, 131-133) are suitably used.

The cell fusion between the immune cells and myeloma cells can be carried out basically in accordance with a method known in the art, for example, a method of Kohler and Milstein et al., (Kohler, G. and Milstein, C. Methods Enzymol. (1981) 73, 3-46).

More specifically, the cell fusion is carried out in the presence of, for example, a cell fusion accelerator, in a general nutrition culture solution. As the fusion accelerator, for example, polyethylene glycol (PEG) or Sendai virus (HVJ) is used and, if desired, an auxiliary agent such as dimethylsulfoxide can be added in order to enhance fusion efficiency.

The ratio of the immune cells and myeloma cells to be used can be arbitrarily determined. For example, the immune cells can be used in a ratio 1 to 10 times compared with the myeloma cells. As the culture solution to be used in the cell fusion, for example, RPMI 1640 culture solution or MEM culture solution suitable for proliferation of the myeloma cell line, and other culture solutions usually used in culturing these cells can be used. In addition, a serum-supplement such as fetal calf serum (FCS) can be used in combination with the culture solution.

Cell fusion is carried out by sufficiently mixing predetermined amounts of the immune cells and myeloma cells in the culture solution and adding a PEG solution (for example, average molecular weight: about 1000 to 6000) previously heated to about 37° C. usually in a concentration of 30 to 60% (w/v) followed by stirring to form desired hybridomas. Subsequently, an operation consisting of intermittently adding an appropriate culture solution, centrifuging the mixture and removing the supernatant, is repeated to remove a cell fusion agent unfavorable for growth of the hybridoma and the like.

The hybridoma thus obtained is selected by culturing in a general selection culture solution such as HAT culture solution (culture solution containing hypoxanthine, aminopterin and thymidine). The culture in the HAT culture solution is continued for a time period (usually, several days to several weeks) sufficient for cells (non-fused cells) other than a desired hybridoma to die. Subsequently, a general limiting dilution method is carried out and screening of a hybridoma producing a desired antibody and single cloning are carried out.

As well as obtaining the above hybridoma by immunizing an animal except a human with an antigen, a hybridoma producing a human antibody having a desired activity (for example, cytostatic activity) can be also obtained by sensitizing human lymphocytes such as human lymphocytes infected with EB virus, with a protein, protein-expressing cell or lysate thereof in vitro, and fusing the sensitized lymphocytes with human-derived myeloma cells, for example U266 (registration number TIB196), having a permanent division potential.

Thus prepared hybridoma producing a monoclonal antibody can be sub-cultured in a general culture solution and stored in liquid nitrogen for a long time.

(2) Polyclonal Antibody

The antibody, in the case of a polyclonal antibody, can be prepared by immunizing a small animal such as a mouse, a human antibody-producing mouse or a rabbit, with natural CSPG5 protein, recombinant CSPG5 protein expressed in the form of a fusion protein with GST and the like in a microorganism such as *Escherichia coli* or a partial peptide thereof to obtain the serum; and purifying the antibody, for example, by ammonium sulfate precipitation, protein A, protein G column, DEAE ion exchange chromatography, an affinity column coupled with CSPG5 protein and a synthetic peptide. In Examples described later, a mouse polyclonal antibody against the extracellular region (outside cancer cell) of the amino acid sequence of CSPG5 protein is prepared and confirmed to have the antitumor effect.

As the human antibody-producing mouse used herein, for example, KM mouse (Kirin Pharma/Medarex) and Xeno mouse (Amgen) are known (for example, International Publication Nos. WO02/43478 and 02/092812). When such a mouse is immunized with CSPG5 protein or a fragment thereof, a complete human polyclonal antibody can be obtained from the blood.

An antigen can be prepared, for example, in accordance with a method using an animal cell (JP Patent Publication (Kohyo) No. 2007-530068A) or a method using baculovirus (for example, International Publication No. WO 98/46777). When the immunogenicity of an antigen is low, the antigen may be bound to a macromolecule such as albumin having immunogenicity and subjected to immunization.

(3) Recombinant Antibody

The antibody, in the case of a genetic recombination antibody, can be prepared, in accordance with a genetic recombination technology, by cloning a gene of the antibody from a hybridoma, incorporating the gene into an appropriate vector, and introducing the vector into a host to produce a recombinant antibody (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). More specifically, cDNA of a variable region (V region) of the antibody is synthesized from mRNA of a hybridoma by using a reverse transcriptase. When DNA encoding a V region of a desired antibody is obtained, it is linked to DNA encoding a constant region (C region) of the desired antibody, and the resultant DNA is integrated into an expression vector. Alternatively, DNA encoding the V region of the antibody may be integrated into an expression vector containing DNA of the C region of the antibody. Said DNA may be Integrated to be expressed under the control of an expression regulatory region, for example, an enhancer and a promoter. Subsequently, a host cell is transformed with the expression vector and allowed to express the genetic recombinant antibody.

Examples of the genetic recombinant antibody include a chimeric antibody, a humanized antibody, a single-chain antibody and multi-chain antibody such as a bispecific antibody.

The "chimeric antibody" is an antibody formed of sequences derived from different animals in combination, for example, an antibody constituted of a variable region of a heavy-chain and a light chain of a mouse antibody and a constant region of a heavy-chain and a light chain of a human antibody. A chimeric antibody can be prepared in accordance with a method known in the art, for example, by ligating DNA encoding an antibody V-region and DNA encoding a human antibody C-region, incorporating the ligate into an expression vector, and introducing the expression vector into a host to allow the host to produce the antibody. As an example, DNA encoding a human/mouse chimeric antibody can be prepared by ligating a DNA encoding a variable region of a light chain or a heavy chain of an antibody derived from a non-human animal (for example, mouse) to DNA encoding a constant region of a light chain or a heavy chain of an antibody derived from a human antibody.

The "humanized antibody" is a modified antibody also called as a reshaped human antibody. The humanized antibody is constructed by grafting an antibody CDR derived from an immunized animal to a complementarity determining region of a human antibody. A general genetic recombination technique for preparing the humanized antibody is also known in the art. Specifically, the humanized antibody is obtained by cloning a DNA encoding a monoclonal antibody; using the resultant as a template to prepare a DNA encoding a light-chain variable region and a heavy-chain variable region by a RT-PCR method, or the like; determining the sequences of the variable regions of the light chain and heavy chain or the sequences of CDR1, CDR2 and CDR3 based on the Kabat EU numbering system (Kabat et al., Sequences of proteins of Immunological Interest, 5th Ed. Public Health Service, National Institute of Health, Bethesda, Md. (1991)); subsequently, synthesizing a DNA sequence, which is designed such that mouse antibody CDRs and framework regions (framework region; FR) of the human antibody can be ligated, by a PCR method using several oligonucleotides prepared designed to have an overlapping portion at the ends; ligating the resultant DNA to DNA encoding a human antibody constant region and then integrating it into an expression vector; and introducing the expression vector into a host and then allowing the host to produce a humanized antibody (see, European Patent Publication No. 239400, International Publication No. WO96/02576). The FRs of the human antibody to be ligated via CDRs are selected such that the CDRs (complementarity determining regions) form a satisfactory antigen binding site. If necessary, the amino acids of the framework region in the variable region of the antibody may be substituted such that the complementarity determining regions of a reshaped human antibody form an appropriate antigen binding site (Sato K., et al., Cancer Research, 1993, 53: 851-856). Further, the framework regions may be substituted with those derived from various human antibodies (International Publication No. WO99/51743).

The framework regions of a human antibody to be ligated via CDRs are selected such that the CDRs (complementarity determining regions) form a satisfactory antigen binding site. If necessary, the amino acids of framework regions in the variable region of an antibody may be substituted such that the complementarity determining regions of a reshaped human antibody form an appropriate antigen binding site (Sato K. et al., Cancer Research 1993, 53: 851-856).

An amino acid in the variable region (for example, FR) and the constant region may be, for example, substituted with another amino acid, after a chimeric antibody and a humanized antibody are formed.

The substitution of amino acids includes substitution of amino acids of, for example, less than 15, less than 10, 8 or less, 7 or less, 6 or less, 5 or less, 4 or less, 3 or less or 2 or less, preferably 1 to 5 amino acids, and more preferably 1 or 2 amino acids. The antibody having a substitution should be functionally equivalent to the antibody having no substitution. Substitution is desirably conservative amino acid substitution, which is a substitution between amino acids having analogous properties in view of charge, side chain, polarity and aromaticity, and the like. The amino acids having analogous property can be classified into, for example, basic amino acids (arginine, lysine, histidine), acidic amino acids (aspartic acid, glutamic acid), uncharged polar amino acids (glycine, asparagine, glutamine, serine, threonine, cysteine, tyrosine), nonpolar amino acids (leucine, isoleucine, alanine, valine, proline, phenylalanine, tryptophan, methionine), branched amino acids (threonine, valine, isoleucine) and aromatic amino acids (phenylalanine, tyrosine, tryptophan, histidine).

Modified antibodies include, for example, antibodies bound to various types of molecules such as polyethylene glycol (PEG). In the modified antibody of the present invention, the material to be bound to the antibody is not limited. Such a modified antibody can be obtained by chemically modifying the obtained antibody. The chemical modification methods have been already established in this field.

The term "functionally equivalent" used herein means that the antibody of interest has the same biological or biochemical activity as the antibody of the present invention, more specifically means that the antibody of interest has a tumor damaging action, and a rejection reaction does not basically occur when the antibody is applied to a human. Such activities include, for example, cytostatic activity or binding activity.

A method of introducing a mutation into the polypeptide is known as a method well known to those skilled in the art for preparing a polypeptide which is functionally equivalent to a predetermined polypeptide. Those skilled in the art can employ a site-specific mutagenesis (Hashimoto-Gotoh, T. et al., (1995) Gene, 152, 271-275: Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367, Kunkel, T A., (1985) Proc. Natl. Acad. Sci. USA., 82, 488-492; Kunkel (1988) Methods Enzymol., 85, 2763-2766) to appropriately introduce a mutation into the antibody of the present invention, thereby preparing an antibody functionally equivalent to the antibody.

An antibody recognizing an epitope of CSPG5 protein that anti-CSPG5 antibody recognizes can be obtained by a method known to those skilled in the art. For example, the antibody is prepared by determining the epitope of CSPG5 protein recognized by anti-CSPG5 antibody by a general method (for example, epitope mapping) and preparing the antibody using a polypeptide having an amino acid sequence contained in the epitope as immunogen. In addition to this method, the antibody can be obtained by a method, for example, determining the epitopes of the antibodies prepared by a general method and selecting an antibody having the same epitope as in the anti-CSPG5 antibody.

The affinity constant (binding constant) Ka (kon/koff) of the anti-CSPG5 antibody of the present invention for the CSPG5 protein on a cancer cell surface is at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$ or at least $10^{13}$ $M^{-1}$. As the binding affinity increases, a stronger antitumor activity can be obtained. Accordingly, if an anti-CSPG5 antibody having a high binding affinity for CSPG5 protein can be obtained, a stronger antitumor effect can be expected, the antibody can be applied to a pharmaceutical composition for treating and/or preventing cancer.

The "single-chain antibody" is an antibody obtained by linearly ligating a heavy-chain variable region and a light-chain variable region via a linker. DNA encoding a single-chain antibody can be prepared by ligating DNA encoding a heavy-chain variable region, DNA encoding a linker and DNA encoding light-chain variable region. The heavy-chain variable region and light-chain variable region used herein are those preferably derived from a human antibody or those derived from a human antibody, in which CDRs alone are replaced by those of an antibody derived from a non-human animal (for example, mouse, rat, chicken). A linker consists of 12 to 19 amino acids, and includes for example, (G4S)3 consisting of 15 amino acids (G. B. Kim et al., Protein Engineering Design and Selection, 2007, 20 (9): 425-432).

In the case of the "bispecific antibody (diabody)", which is an antibody capable of specifically binding to two different epitopes, DNA encoding the bispecific antibody can be prepared by binding, for example, DNA encoding heavy-chain variable region A, DNA encoding light-chain variable region B, DNA encoding heavy-chain variable region B and DNA encoding light-chain variable region A sequentially in this order (provided that DNA encoding light-chain variable region B and DNA encoding heavy-chain variable region B are connected via DNA encoding a linker as mentioned above). The heavy-chain variable regions and light-chain variable regions each are preferably derived from a human antibody or derived from a human antibody, in which CDRs alone are replaced by those of an antibody derived from a non-human animal (for example, mouse, rat, chicken).

A recombinant antibody can be prepared by integrating the recombinant DNA prepared as described above into a single or a plurality of appropriate vectors, introducing the vector(s) into a host cell (for example, mammalian cells, yeast cells, insect cells) and allowing the host cell to (co-)express the recombinant DNA (P. J. Delves., ANTIBODY PRODUCTION ESSENTIAL TECHNIQUES., 1997 WILEY, P. Shepherd and C. Dean., Monoclonal Antibodies., 2000 OXFORD UNIVERSITY PRESS; J. W. Goding., Monoclonal Antibodies: principles and practice., 1993 ACADEMIC PRESS).

The antibody as mentioned above preferably has a cytotoxic activity and can produce an antitumor effect due to the cytotoxic activity.

The antibody of the present invention can be conjugated with another antitumor agent. The antibody and the antitumor agent can be conjugated via a spacer having a group reactive to an amino group, a carboxyl group, a hydroxy group, a thiol group, and the like (examples of the reactive group include a succinimidyl group, a formyl group, a 2-pyridyldithio group, a maleimidyl group, an alkoxycarbonyl group and a hydroxy group).

Examples of the antitumor agent include the following antitumor agents known to public by literatures etc., such as paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chloRNAphazine, cholophosphamide, estramustine, ifosfamide, mechlorethamine, mechlorethamine oxide hydrochloride, melphalan, novembichin, phenesterine, prednimustine, trofosfamide, uracilmustard, carmustine, chlorozotocin, fotemustine, lomustine, nimustine, ranimustine, calicheamicin, dynemycin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, ADRI-AMYCIN, epirubicin, esolubicin, idarubicin, marcellomycin, mitomycin C, mycophenolic acid, nogalamycin, olivomycin, pepromycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamipurine, thioguanine, ancitabine, azacitidine, 6-azauridine, carmofur, cytarabine, dideoxyuridine, doxifluridine, enocitabine, floxuridine; androgens such as calusterone, dromostanolone propionate, epithiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, doxetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, a topoisomerase inhibitor, difluoromethylornithine (DMFO), retinoic acid, capecitabine and pharmaceutically acceptable salts or derivatives thereof.

A radioactive isotope known to public by literatures etc., such as $^{211}$At, $^{131}$I, $^{125}$I, $^{90}$Y, $^{186}$Re, $^{188}$Re, $^{153}$Sm, $^{212}$Bi, $^{32}$P, $^{175}$Lu and $^{176}$Lu, may be bound to the antibody of the present invention. As the radioactive isotope, preferably, a radioactive isotope is effective for treating and diagnosing a tumor.

The antibody of the present invention is an antibody having immunological reactivity with CSPG5 protein or an antibody specifically recognizing CSPG5 protein. The antibody should be an antibody having a structure such that no or little rejection reaction is produced in the target animal to which the antibody is administered. Examples of such an antibody in the case where a target animal is, a human etc., include a human antibody, a humanized antibody and a chimeric antibody (for example, a human-mouse chimeric antibody).

A hybridoma capable of producing a human antibody or non-human animal antibody (for example, mouse antibody) against human CSPG5 protein, is prepared. A monoclonal antibody produced by the hybridoma is recovered and determined as to whether it is a desired antibody or not based on immunological binding property to the human CSPG5 protein and cytotoxic activity as an indicator. In this manner, a desired monoclonal antibody-producing hybridoma is identified and selected. Thereafter, as described above, DNA encoding the variable regions of the heavy chain and light chain of a desired antibody is prepared from the hybridoma and the nucleotide sequence thereof is determined. The information of the nucleotide sequence of the DNA is used for preparing another antibody.

The present invention further provides DNA encoding the antibody of the present invention described above, DNA encoding the heavy chain or light chain of the antibody described above, or DNA encoding a variable region of the heavy chain or light chain of the antibody described above.

CDRs encoded by these DNA molecules are regions determining specificity of the antibody. The nucleotide sequence encoding the region (more specifically, constant region and framework region) other than CDRs of the antibody may be a nucleotide sequence derived from another antibody. The "another antibody" used herein may include an antibody derived from an organism other than a human; however, an antibody derived from a human is preferable in order to reduce side effects. More specifically, in the above DNA, the regions encoding individual framework regions of the heavy chain and the light chain and the regions encoding individual constant regions thereof preferably contain nucleotide sequences encoding the corresponding amino acid sequences derived from a human antibody.

DNA of an antibody serving as an active ingredient of the present invention, can be obtained, for example, by the above method or the following method. First, total RNA is prepared from a hybridoma relating to the antibody of the present invention by a commercially available RNA extraction kit, and then, cDNA is synthesized with a reverse transcriptase by using random primers etc. Subsequently, cDNA encoding the antibody is amplified by a PCR method using oligonucleotides of the conserved sequences in the variable regions of the heavy chain gene and light chain gene of a known mouse antibody, as primers. The constant region-encoding sequence can be obtained by amplifying a known sequence by a PCR method. The nucleotide sequence of DNA can be determined by a routine method, for example, by integrating DNA into a sequencing plasmid or a phage etc.

It is considered that the antitumor effect of the anti-CSPG5 antibody to be used in the present invention on CSPG5 protein expressing cancer cells is produced by mechanism of antibody-dependent cell-mediated cytotoxicity (ADCC) via effector cells and complement dependent cytotoxicity (CDC).

Accordingly, the activity of the anti-CSPG5 antibody used in the present invention can be evaluated by measuring the ADCC activity or CDC activity against the cancer cells expressing CSPG5 protein in vitro, as specifically described in Examples.

The anti-CSPG5 antibody is considered to be useful for treating or preventing cancer, since the antibody used in the present invention binds to the extracellular region of CSPG5 protein present on the cancer cell surface and exerts an anti-tumor action based on the activity(s) mentioned above. More specifically, the present invention provides a pharmaceutical composition containing an anti-CSPG5 antibody as an active ingredient for treating and/or preventing cancer. When the anti-CSPG5 antibody is used for administration to a human body (antibody treatment), the anti-CSPG5 antibody is preferably prepared as a human antibody or a humanized antibody in order to reduce immunogenicity.

<Binding to Antigen-Expressing Cells>

The ability of an antibody to bind to CSPG5 protein can be specified, for example, by a binding assay such as ELISA, Western blotting, immunofluorescence and flow cytometric analysis, as described in Examples.

<Immunohistochemical Staining>

With respect to the antibody recognizing CSPG5 protein, the reactivity thereof with CSPG5 protein can be checked by using tissues and slices thereof in accordance with immunohistochemical staining method well known to those skilled in the art. For example, a tissue obtained from a patient during a surgical operation; or a tissue obtained from an animal having a heterologous tissue grafted by administering a cells expressing CSPG5 protein naturally or after transfection; frozen tissue slice fixed with paraformaldehyde or acetone; or paraffin-embedded tissue slice fixed with paraformaldehyde.

An antibody having a reactivity with CSPG5 protein can be stained with various methods for immunohistochemical staining. For example, visualization can be made by reacting a horseradish peroxidase-conjugated goat anti-mouse antibody and a horseradish peroxidase-conjugated goat anti-rabbit antibody.

<Pharmaceutical Composition>

A target of the pharmaceutical composition for treating and/or preventing cancer according to the present invention is not particularly limited as long as it is cancer (cells) expressing CSPG5 protein on the cell surface.

The terms "tumor" and "cancer" used herein refer to malignant neoplasms and are interchangeably used.

In the present invention, a target cancer is a cancer expressing CSPG5 gene, preferably, in particular, cancers expressing genes encoding amino acid sequences represented by SEQ ID NOs: 2, 4, 6, 8, 10, 12, 14 and 16 or polypeptides containing partial sequences of the amino acid sequences consisting of at least 7 consecutive amino acids, more preferably, cancers except ovarian cancer, further preferably, breast cancer, lung cancer, brain tumor, leukemia, malignant lymphoma, mastocytoma, melanoma or neuroblastoma, more preferably, leukemia or malignant lymphoma.

Examples of these specific cancers include, but are not limited to, breast adenocarcinoma, complex breast adenocarcinoma, mammary gland malignant mixed tumor, ductal papillary adenocarcinoma, lung adenocarcinoma, squamous cell carcinoma, small cell cancer, large cell cancer, glioma which is a neuroepithelial tissue tumor, ependymoma, neurocytoma, fetus neuroectodermal tumor, neurinoma, neurofibroma, meningioma, chronic lymphocytic leukemia, Hodgkin's lymphoma, gastrointestinal-tract lymphoma, gastrointestinal lymphoma, small to medium cell lymphoma, cecal cancer, ascending colon cancer, descending colon cancer, transverse colon cancer, sigmoid colon cancer and rectal cancer.

An animal of the interest for the pharmaceutical composition of the present invention is a mammal; for example, primates, pet animals, domestic animals and animals for competitive use, particularly preferably, humans, dogs and cats.

When the antibody according to the present invention is used as a pharmaceutical composition, the antibody can be formulated by a method known to those skilled in the art. For example, it can be used parenterally in the form of a sterile solution or suspension for injection when the antibody is mixed with water or a pharmaceutically acceptable liquid. It is also contemplated that the antibody is appropriately mixed with a pharmaceutically acceptable carrier or medium; for example, sterile water, physiological saline, a vegetable oil, an emulsifying agent, a suspending agent, a surfactant, a stabilizer, a flavoring agent, an excipient, a vehicle, an antiseptic agent and/or a binder, in a unit dose required for generally accepted pharmaceuticals to prepare medicinal agents. The amount of active ingredient in these medicinal agents is specified such that the dose within a predetermined range can be appropriately obtained.

The sterile composition for injection can be formulated by using a vehicle such as distilled water for injection in accordance with a routine manner for preparation of medicinal agents.

Examples of an aqueous solution for injection include physiological saline and isotonic solutions containing glucose and other adjuvant(s); for example, D-sorbitol, D-mannose, D-mannitol and sodium chloride, and it can be used in combination with an appropriate solubilizing agent such as an alcohol, for example, ethanol, a polyalcohol such as propylene glycol and polyethylene glycol, and a nonionic surfactant such as polysorbate80™ and HCO-60.

Examples of an oily solution include sesame oil and soybean oil. A solubilizing agent such as benzyl benzoate and benzyl alcohol may be used in combination. Furthermore, a buffer such as a phosphate buffer and a sodium acetate buffer, a soothing agent such as procaine hydrochloride, a stabilizer such as benzyl alcohol and phenol, and/or an antioxidant may be blended in combination. The injection solution prepared is usually stored in appropriate ampoules.

Examples of administration method include oral administration or parenteral administration, preferably parenteral administration, in particular, injection, nasal administration, transpulmonary administration and transdermal administration. Examples of the injection include intravenous injection, intramuscular injection, intraperitoneal injection and subcutaneous injection for systemic administration or local administration.

The administration method can be appropriately selected depending upon the age, weight, sex and symptom of the patient. As a dose of a pharmaceutical composition containing an antibody or a polynucleotide encoding an antibody may be selected from the range of e.g., 0.0001 mg to 1000 mg per time per body-weight of 1 kg, or from the range of e.g., 0.001 to 100000 mg/body per patient. However, the dose is not limited by these numerical values. The dose and administration method may vary depending on the body weight, age, sex, symptom of the patient, and the like and can be appropriately selected by those skilled in the art.

EXAMPLES

The present invention is more specifically described below by way of Examples; however, the scope of the present invention is not limited by these examples.

Example 1: Identification of Novel Cancer Antigen Protein by SEREX Method (1) Preparation of cDNA Library Total RNA was extracted from the testicular tissue of a healthy dog in accordance with the Acid guanidium-Phenol-Chloroform method, and then, poly A RNA was purified by using Oligotex-dT30 mRNA purification Kit (manufactured by Takara Shuzo Co., Ltd.) in accordance with the protocol attached to the kit.

Dog testis cDNA phage library was synthesized using the mRNA (5 μg) obtained above. The cDNA phage library was prepared by using cDNA Synthesis Kit, ZAP-cDNA Synthesis Kit or ZAP-cDNA GigapackIII Gold Clonig Kit (manufactured by Agilent Technologies) in accordance with the protocol attached to the kit. The size of the cDNA phage library prepared was $7.73 \times 10^5$ pfu/mL.

(2) Screening of cDNA Library with Serum

Immuno-screening was carried out using the dog testis cDNA phage library prepared above. More specifically, host *Escherichia coli* (XL1-Blue MRF) was infected with phages so as to obtain 2210 clones in a NZY agarose plate of ϕ90×15 mm and culture was carried out at 42° C. for 3 to 4 hours to form plaques. The plate was covered with nitrocellulose membrane (Hybond C Extra: manufactured by GE Healthcare Bio-Scinece) impregnated with IPTG (isopropyl-β-D-thiogalactoside) at 37° C. for 4 hours to induce protein expression and the protein was transferred to the membrane. Thereafter, the membrane was taken, soaked in TBS (10 mM Tris-HCl, 150 mM NaCl pH7.5) containing 0.5% skim milk powder and shaken at 4° C. overnight to suppress a nonspecific reaction. This filter was allowed to react with the 500-fold diluted serum of a disease dog at room temperature for 2 to 3 hours.

As the disease-dog serum mentioned above, the serum taken from a dog with breast cancer was used. The serum was stored at −80° C. and pretreated right before use. The pretreatment is carried out in accordance with the following method. First, host *Escherichia coli* (XL1-Blure MRF') was infected with λ ZAP Express phages having no inserted foreign gene and cultured on a NZY plate medium at 37° C. overnight. Then, a buffer (0.2 M NaHCO₃ pH8.3) containing 0.5 M NaCl was added to the plate, and allowed to stand still at 4° C. for 15 hours. Thereafter, the supernatant was recovered as an *Escherichia coli*/phage extraction liquid. Subsequently, the *Escherichia coli*/phage extraction liquid recovered was passed through a NHS-column (manufactured by GE Healthcare Bio-Science) to allow proteins derived from *Escherichia coli*/phage to immobilize to the column. The disease dog serum was passed through the protein-immobilized column to react to remove the antibody adsorbed to *Escherichia coli* and phage (protein) from the serum. The serum fraction passed though the column was diluted 500 fold with TBS containing 0.5% skim milk powder and used as a sample for immuno-screening.

The serum thus treated and the above fusion protein were blotted on a membrane and the membrane was washed four times with TBS-T (0.05% Tween (registered trade mark) 20/TBS), then allowed to react with goat anti-dog IgG (Goat anti Dog IgG-h+l HRP conjugated; manufactured by BETHYL Laboratories) as a secondary antibody, which was diluted 5000-fold with TBS containing 0.5% skim milk powder, at room temperature for one hour. Detection was made by an enzymatic chromogenic reaction using NBT/BCIP reaction solution (manufactured by Roche). Colonies corresponding to chromogenic reaction positive-sites were picked up from the NZY agarose plate of φ90×15 mm and dissolved in 500 μL of SM buffer solution (100 mM NaCl, 10 mM MgClSO$_4$, 50 mM Tris-HCl, 0.01% gelatin, pH7.5). The secondary and tertiary screening were carried out by repeating the above method until the chromogenic reaction positive colonies were unified. Through screening of 9110 phage clones reacting with IgG in the serum, a single positive clone was isolated.

(3) Homology Search of Isolated Antigen Gene

In order to subject the single positive clone isolated by the above method to nucleotide sequence analysis, an operation for transferring from a phage vector to a plasmid vector was carried out. More specifically, a solution (200 μL) containing host *Escherichia coli* (XL1-Blue MRF') prepared so as to show an absorbance at OD$_{600}$ of 1.0, a purified phage solution (100 μL) and further 1 μL of ExAssist helper phage (manufactured by Agilent Technologies) were mixed and allowed to react at 37° C. for 15 minutes. 3 mL of LB medium was added and culture was carried out at 37° C. for 2.5 to 3 hours. Immediately after cultivation, the medium was kept warm in a water bath of 70° C. for 20 minutes, and centrifuged at 4° C. and 1000×g, for 15 minutes. The supernatant was recovered as a phargemid solution. Subsequently, a solution (200 μL) containing a phargemid host *Escherichia coli* (SOLR) was prepared so as to have an absorbance at OD$_{600}$ of 1.0 and a purified phage solution (10 μL) were mixed and reacted at 37° C. for 15 minutes. The resultant solution (50 μL) was seeded on an ampicillin (final concentration: 50 μg/mL)-containing LB agar medium and cultured at 37° C. overnight. A single transformed SOLR colony was picked up, cultured in ampicillin (final concentration: 50 μg/mL)-containing LB medium at 37° C. and thereafter, purified by QIAGEN plasmid Miniprep Kit (manufactured by QIAGEN) to obtain a plasmid DNA having a desired insert.

The purified plasmid was subjected to primer walking using T3 primer represented by SEQ ID NO: 17 and T7 primer represented by SEQ ID NO: 18 to analyze the full-length sequence of the insert. The gene sequence represented by SEQ ID NO: 1 was obtained by the sequencing. Using the nucleotide sequence and amino acid sequence of the gene, sequence identity search (search for identical sequence with known genes) was carried out by a sequence identity search program, BLAST search (http://www.ncbi.nlm.nih.gov/BLAST/). As a result, it was found that the gene obtained above is CSPG5 gene. In the human CSPG5 gene, which is a human homologous factor with a canine CSPG5 gene, a nucleotide-sequence identity was 87%, and in human CSPG5 protein, an amino acid sequence identity was 87%. In cat CSPG5 gene, a nucleotide sequence identity was 92%. In cat CSPG5 protein, an amino acid sequence identity was 91%. In mouse homologous factor, i.e., mouse CSPG5 gene, a nucleotide sequence identity was 84%. In mouse CSPG5 protein, an amino acid sequence identity was 85%. The nucleotide sequences of the human CSPG5 gene are represented by SEQ ID NOs: 3, 5, 7, 9 and 11. The amino acid sequences of the human CSPG5 protein are represented by SEQ ID NO: 4, 6, 8, 10 and 12. The nucleotide sequence of the cat CSPG5 gene is represented by SEQ ID NO: 13. The amino acid sequence of the cat CSPG5 protein is represented by SEQ ID NO: 14. The nucleotide sequence of the mouse CSPG5 gene is represented by SEQ ID NO: 15. The amino acid sequence of the mouse CSPG5 protein is represented by SEQ ID NO: 16.

(4) Gene Expression Analysis in Tissues

Figure 2:
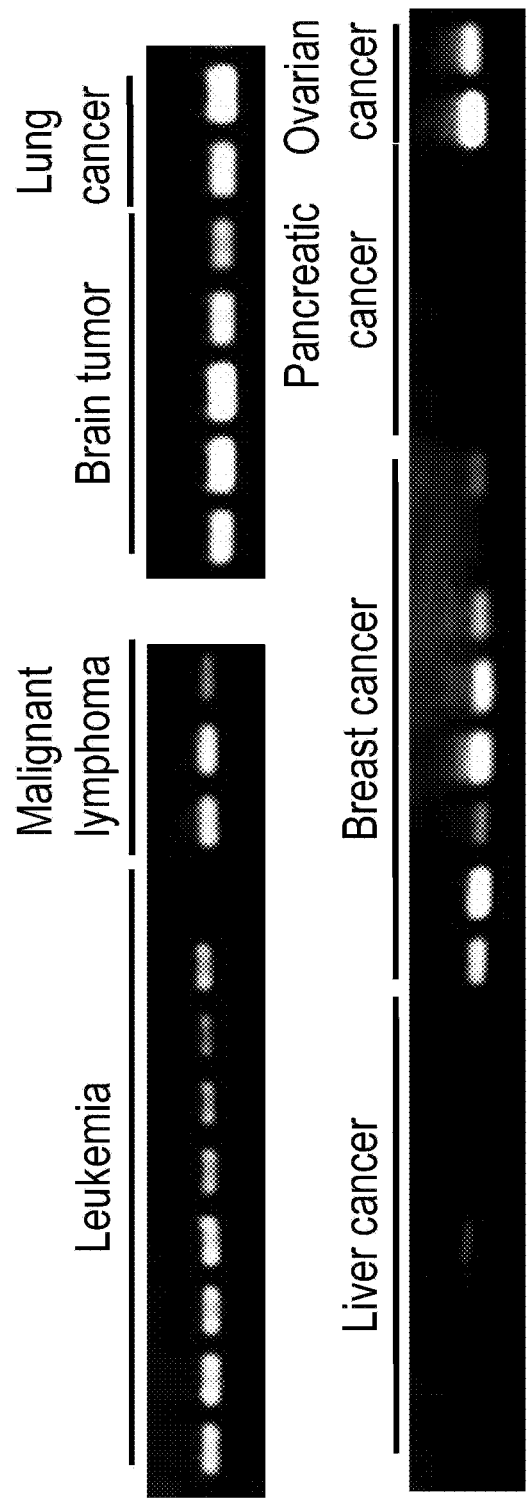
FIG. 2 shows expression patterns of identified CSPG5 gene in human tumor tissues or cancer cell lines.
Figure 3:
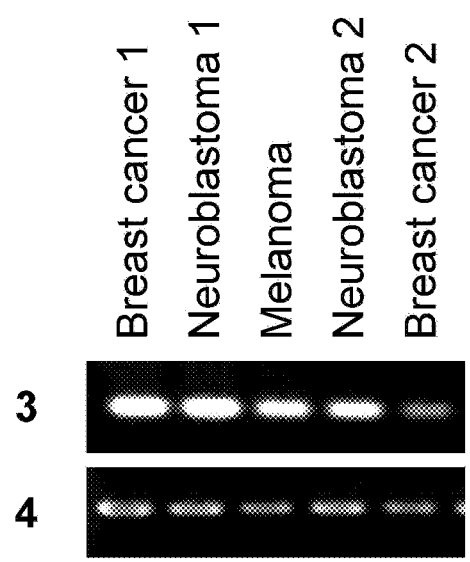
FIG. 3 shows expression patterns of identified CSPG5 gene in mouse tumor tissues or cancer cell lines. Reference number 3 shows expression patterns of mouse CSPG5 gene in individual mouse tissues and cell lines; reference number 4 shows expression patterns of mouse GAPDH gene in individual mouse tissues and cell lines.

Expression of the gene obtained by the above method in normal tissues and cancer tissues of a dog, human and mouse and a cancer cell lines was checked by a RT-PCR (Reverse Transcription-PCR) method. The reverse transcription reaction was carried out as follows. First, total RNA was extracted from individual tissues (50 to 100 mg) and individual cell lines (5 to 10×10$^6$ cells) by use of TRIZOL reagent (manufactured by Thermo Fisher Scientific) in accordance with the attached protocol. Using the total RNA, cDNA was synthesized by using Superscript First-Strand Synthesis System for RT-PCR (manufactured by Thermo Fisher Scientific) in accordance with the protocol attached. As the cDNA of the human normal tissues (brain, hippocampus, testicles, colon, placenta), gene pool cDNA (manufactured by Thermo Fisher Scientific), QUICK-Clone cDNA (manufactured by Clontech Laboratories, Inc.) and Large-Insert cDNA Library (manufactured by Clontech Laboratories, Inc.) were used. The PCR reaction was carried out by using the obtained gene specific primers (canine primers are represented by SEQ ID NOs: 19 and 20, human primers are represented by SEQ ID NOs: 21 and 22, mouse primers are represented by SEQ ID NOs: 23 and 24) as follows. First, reagents and the attached buffer were added to 0.25 μL of the sample prepared by the reverse transcription reaction to obtain a mixture having a total amount of 25 μL containing the above primers (2 μM for each), dNTPs (0.2 mM for each) and a 0.65 U ExTaq polymerase (manufactured by Takara Shuzo Co., Ltd.). The reaction mixture was subjected to a Thermal Cycler (manufactured by BIO RAD) in which a cycle consisting of a reaction at 94° C. for 30 seconds, a reaction at 55° C. for 30 seconds and a reaction at 72° C. for one minute, was repeated 30 times. For comparison, a GAPDH-specific primer (canine and human GAPDH primers are represented by SEQ ID NOs: 25 and 26, mouse GAPDH primers are represented by SEQ ID NOs: 27 and 28) were simultaneously used. As a result, as shown in FIG. 1, the canine CSPG5 gene was not expressed in almost all normal canine tissues, but strongly expressed in the canine tumor tissue. Similarly to the canine CSPG5 gene, expression of human and mouse CSPG5 genes in normal human and mouse tissues was rarely confirmed; however, expression thereof was detected in cancer cells, for example, breast cancer, lung cancer, brain tumor, ovarian cancer, leukemia, malignant lymphoma cells (FIGS. 2 and 3).

Example 2: Preparation of Human CSPG5 Protein (1) Cloning of Full-Length cDNA Encoding Human CSPG5 and cDNA Encoding the Extracellular Region of Human CSPG5

A full-length cDNA encoding human CSPG5 gene was obtained by cloning in accordance with the following method based on the gene represented by SEQ ID NO: 7 obtained Example 1. PCR was carried out as follows: Reagents and the attached buffer were mixed to obtain a total amount of 50 μL of mixture containing the cDNA molecule (1 μL), which was one of those taken from various tissues and cells (prepared in Example 1) and whose expression was confirmed by the RT-PCR method, two types of primers (0.4 μM for each) having KpnI and EcoRI restriction enzyme cleavage sequences (represented by SEQ ID NOs: 29 and 30), 0.2 mM dNTPs, and 1.25 U PrimeSTAR HS polymerase (manufactured by Takara Shuzo Co., Ltd.), and the resultant was subjected to a Thermal Cycler (manufactured by BIO RAD), in which a cycle (PCR) consisting of a reaction at 98° C. for 10 seconds and a reaction at 68° C. for 2.5 minutes was repeated 30 times. Incidentally, the above two types of primers were used for amplifying a region encoding a full length amino acid sequence represented by SEQ ID NO: 7. After the PCR, the amplified DNA was electrophoresed on a 1% agarose gel and a DNA fragment of about 1.7 kbp was purified by use of QIAquick Gel Extraction Kit (manufactured by QIAGEN). The amplified product obtained by the above PCR reaction was inserted in pcDNA3.1 (Thermo Fisher Scientific) (hereinafter referred to as CSPG5/pcDNA3.1) and confirmed to be a cDNA sequence encoding human CSPG5 gene by sequencing using a DNA sequencer. The sequence represented by SEQ ID NO: 7 represents the nucleotide sequence of human CSPG5 gene and the sequence represented by SEQ ID NO: 8 represents the amino acid sequence of human CSPG5 protein.

A PCR reaction was carried out based on SEQ ID NO: 7 as follows. Reagents and the attached buffer were mixed to obtain a total amount of 50 µL of mixture containing two types of primers (0.4 µM for each)(represented by SEQ ID NOs: 29 and 30) containing KpnI and EcoRI restriction enzyme cleavage sequences, 0.2 mM dNTPs and 1.25 U PrimeSTAR HS polymerase (manufactured by Takara Shuzo Co., Ltd.), and the resultant was subjected to a Thermal Cycler (manufactured by BIO RAD) in which the cycle consisting of a reaction at 98° C. for 10 seconds and a reaction at 68° C. for 2.5 minutes was repeated 30 times. Incidentally, the above two types of primers were used for amplifying a region encoding the amino acid sequence of the extracellular region of CSPG5 protein represented by SEQ ID NO: 7. After the PCR, the amplified DNA was electrophoresed on a 1% agarose gel and a DNA fragment of about 1.3 kbp was purified by use of QIAquick Gel Extraction Kit (manufactured by QIAGEN). The amplified product obtained by the above PCR reaction was ligated to pcDNA3.1 to which cDNA encoding a mouse IgG2a Fc protein is inserted to obtain an expression vector (hereinafter referred to as pcDNA-hCSPG5 ECD-IgG2aFc) encoding a human CSPG5 extracellular region/mouse IgG2a Fc fusion protein (hereinafter referred to as hCSPG5 ECD-mIgG2aFc) and confirmed to be a cDNA sequence encoding hCSPG5 ECD-mIgG2aFc by sequencing using a DNA sequencer. The sequence represented by SEQ ID NO: 32 represents the nucleotide sequence encoding hCSPG5 ECD-mIgG2aFc and the sequence represented by SEQ ID NO: 33 represents the amino acid sequence of hCSPG5 ECD-mIgG2aFc.

(2) Preparation of hCSPG5 ECD-mIgG2aFc

As an immunizing antigen for preparing an antibody against CSPG5 protein, hCSPG5 ECD-mIgG2aFc was prepared.

An expression vector, pcDNA-hCSPG5 ECD-mIgG2aFc was introduced into a human fetal kidney cell line, HEK293 cell, by a lipofection method. hCSPG5 ECD-mIgG2aFc was purified from the culture supernatant 7 days after introduction. The culture supernatant was applied to a Hi Trap proteinG HP (GE Healthcare Bioscience) column, washed with a binding buffer (20 mM sodium phosphate (pH 7.0)), and eluted with an elution buffer (0.1 M glycine-HCl (pH 2.7)). The eluted liquid was placed in a tube containing a neutralization buffer (1 M Tris-HCl (pH 9.0)) and immediately neutralized. Then, the eluted liquid obtained by the above method was subjected to ultrafiltration using NANOSEP 10K OMEGA (manufactured by PALL) and replacement with a physiological phosphate buffer solution (manufactured by NISSUI PHARMACEUTICAL CO., LTD.), and then aseptically filtered by HT Tuffryn Acrodisc of 0.22 µm (manufactured by PALL) and used in the following experiments.

Example 3: Preparation of Polyclonal Antibody Binding to CSPG5 Extracellular Region (1) Preparation of Polyclonal Antibody Against CSPG5

To obtain an antibody binding to the extracellular region of CSPG5, 0.1 mg of hCSPG5 ECD-mIgG2aFc prepared as described above as an antigen and an equivalent amount of complete Freund's adjuvant (CFA) solution were mixed and the resultant mixture was subcutaneously administered to a mouse 4 times every two week. Thereafter, blood was taken to obtain an anti-serum containing a polyclonal antibody. The anti-serum was purified by Protein G carrier (manufactured by GE Healthcare Bioscience) to obtain a polyclonal antibody against hCSPG5 ECD-mIgG2aFc. The serum of a mouse to which the antigen was not administered was purified by use of Protein G carrier in the same manner as above and used as a control antibody.

(2) Establishment of Cells Constantly Expressing Full-Length Human CSPG5

CSPG5/pcDNA3.1 prepared as described above was introduced into CHO-K1 cells (ATCC) by a lipofection method. Screening was carried out by a 500 µg/mL G418 (Nacalai) to establish a CHO cell line constantly expressing full-length human CSPG5 (CHO-CSPG5). An expression vector having no cDNA encoding CSPG5 inserted therein (hereinafter referred to as emp/pcDNA3.1) was introduced and screened in the same manner as above to obtain cells to be used as control cells (hereinafter referred to as CHO-emp).

Similarly, CSPG5/pcDNA3.1 was introduced to murine leukemia cell line EL4 (ATCC) by a lipofection method. Screening was carried out by a 500 µg/mL G418 (Nacalai) to establish EL4 cell line constantly expressing full-length human CSPG5 gene (EL4-CSPG5). An expression vector having no cDNA encoding CSPG5 gene inserted therein (hereinafter referred to as emp/pcDNA3.1) was introduced and screened in the same manner as above to obtain cells to be used as control cells (hereinafter referred to as EL4-emp).

(3) Analysis of Expression of Antigen Protein on Cell Surface

It was examined whether the polyclonal antibody prepared in step (1) specifically reacts with CSPG5 protein expressed on the surface of the cell established in step (2). CHO-CSPG5 cells and CHO-emp cells ($10^6$ cells for each) were separately placed in 1.5 mL-volume micro-centrifuge tubes and centrifuged. To each of the tubes, the polyclonal antibody (2 µg (5 µL)) against CSPG5 protein prepared in the above step (1) was added. The mixture was further suspended with PBS (95 µL) containing a 0.1% fetal bovine serum and allowed to stand still on ice for one hour. After washing with PBS, the mixture was suspended with 5 µL of an FITC-labeled goat anti-mouse IgG antibody (manufactured by Santacruz) and 95 µL of PBS containing a 0.1% fetal bovine serum (FBS) and allowed to stand still on ice for one hour. After washing with PBS, fluorescence intensity was measured by FACS Calibur (manufactured by BD). On the other hand, the control antibody prepared in the above step (1) was subjected to the same operation as above in place of the polyclonal antibody against CSPG5 protein and used as a control. As a result, the CHO-CSPG5 cells to which the anti-human CSPG5 antibody was added exhibited increase of fluorescence intensity of about 221% compared with the control. The same operation was applied to CHO-emp cells. As a result, the CHO-emp cell to which anti-human CSPG5 antibody was added exhibited the same fluorescence intensity as the control. It was demonstrated from these results that the anti-human CSPG5 antibody specifically binds to CSPG5 protein expressed on the surface of a cell membrane.

The increase rate of the fluorescence intensity was expressed by an increase rate of mean fluorescence intensity (MFI value) of each cell and calculated in accordance with the following formula:

Increase rate of mean fluorescence intensity(fluorescence intensity increase rate)(%)=((MFI value of cells to which an anti-human CSPG5 antibody was reacted)−(control MFI value))÷(control MFI value)×100

Next, it was examined whether or not CSPG5 protein is expressed on the cell surface with respect to two types of leukemia cell lines (K562, THP-1) and two types of malignant lymphoma cell lines (L-1236, P3HR-1) on which CSPG5 gene was confirmed to be highly expressed. Individual human cell lines ($10^6$ cells) on which gene expression were confirmed in the above were separately placed in 1.5 mL-volume micro-centrifuge tubes and centrifuged. To each of the tubes, the polyclonal antibody (2 μg (5 μL)) against CSPG5 protein prepared in the above step (1) was added. The mixture was further suspended with PBS (95 μL) containing a 0.1% fetal bovine serum and allowed to stand still on ice for one hour. After washing with PBS, the mixture was suspended with 5 μL of an FITC-labeled goat anti-mouse IgG antibody (manufactured by Santacruz) and 95 μL of PBS containing a 0.1% fetal bovine serum (FBS) and allowed to stand still on ice for one hour. After washing with PBS, fluorescence intensity was measured by FACS Calibur (manufactured by BD). On the other hand, the control antibody prepared in the above step (1) was subjected to the same operation as above in place of the polyclonal antibody against CSPG5 protein and used as a control. As a result, the cell to which the anti-human CSPG5 antibody was added exhibited increase of fluorescence intensity of 30% or more compared with the control. More specifically, K562 exhibited 184% increase of fluorescence intensity, THP-1 51% increase, L-1236 115% increase, and P3HR-1 82% increase. It was confirmed from these results that CSPG5 protein are expressed on the surface of cell membrane of the human cancer cell lines.

Figure 4:
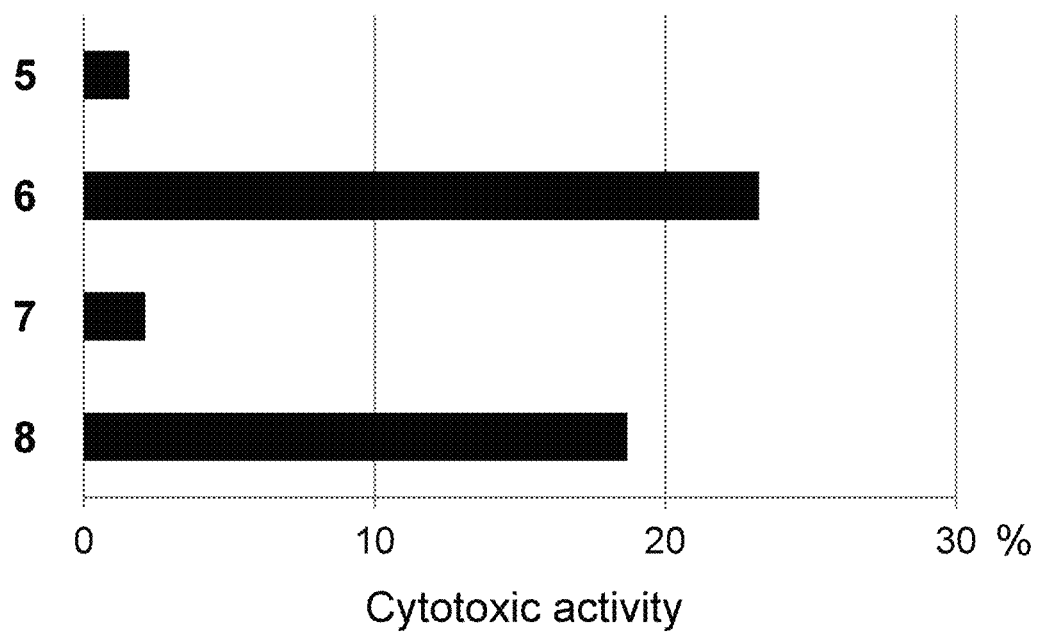
FIG. 4 shows cytotoxic activity of a polyclonal antibody against CSPG5 protein (anti-CSPG5 polyclonal antibody) on a leukemia cell line (K562) and malignant lymphoma cells (L-1236) expressing CSPG5 gene. In the figure, reference number 5 shows the cytotoxic activity against K562 cells when a control polyclonal antibody was added; reference number 6 shows the cytotoxic activity against K562 cells when an anti-CSPG5 polyclonal antibody was added; reference number 7 shows the cytotoxic activity against L-1236 cells when the control polyclonal antibody was added; and reference number 8 shows the cytotoxic activity against L-1236 cell when the anti-CSPG5 polyclonal antibody was added.
Figure 5:
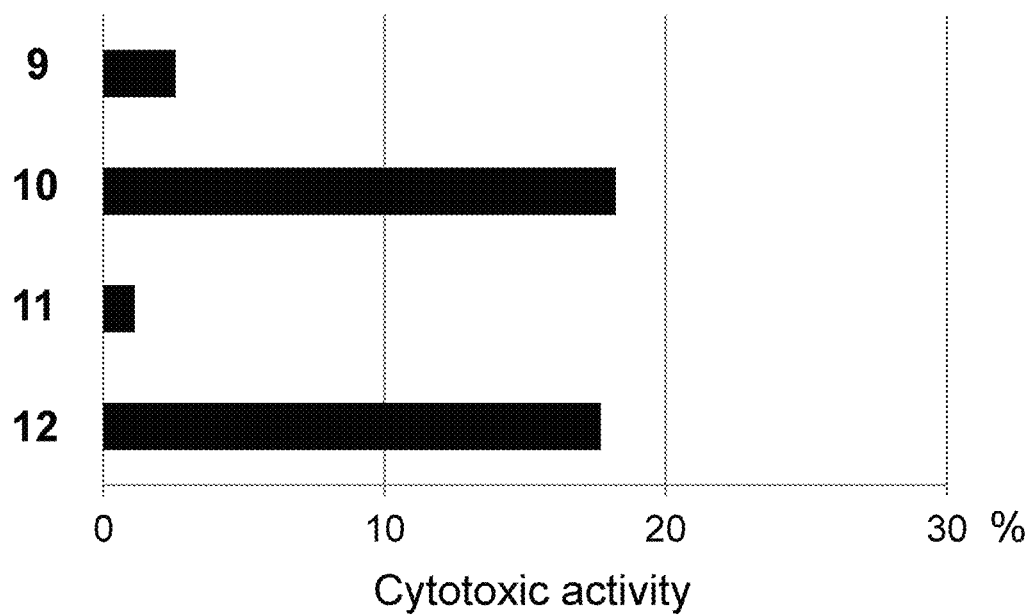
FIG. 5 shows cytotoxic activity of a monoclonal antibody against CSPG5 protein (anti-CSPG5 monoclonal antibody) on a leukemia cell line (K562) and malignant lymphoma cells (L-1236) expressing CSPG5 gene. In the figure, reference number 9 shows the cytotoxic activity against K562 cells when a control monoclonal antibody was added; reference number 10 shows the cytotoxic activity against K562 cells when an anti-CSPG5 monoclonal antibody was added; reference number 11 shows the cytotoxic activity against L-1236 cells when the control monoclonal antibody was added; and reference number 12 shows the cytotoxic activity against L-1236 cell when the anti-CSPG5 monoclonal antibody was added.

Example 4: Antitumor Effect (ADCC Activity) of Polyclonal Antibody Against CSPG5 Protein on Cancer Cells Next, it was examined whether a polyclonal antibody against CSPG5 protein can damage tumor cells expressing CSPG5 protein. Evaluation was made by using the polyclonal antibody against human CSPG5 prepared in Example 3. Human leukemia cell line K562 and malignant lymphoma cell line L-1236 ($10^6$ cells for each) on which expression of CSPG5 protein was confirmed, were separately collected in a centrifuge tube of 50 mL in volume. To the tube, 100 μCi chromium 51 was added and the tube was incubated at 37° C. for two hours. Thereafter, the cells were washed three times with RPMI 1640 medium containing a 10% fetal bovine serum and added to wells of a 96-well (with a V-shape bottom) plate in a ratio of $10^3$ cells per well. To this, the above polyclonal antibody against human CSPG5 protein was added in a ratio of 1 μg per well and further lymphocytes separated from the peripheral blood of a rabbit was added in a ratio of 2×$10^5$ cells per well. The plate was cultured at 37° C. in a 5% $CO_2$ condition for 4 hours. After culturing, the amount of chromium (Cr) 51 released from damaged tumor cells in the culture supernatant was measured and the ADCC activity of a polyclonal antibody against human CSPG5 protein on each of the cancer cells was calculated. As a result, it was confirmed that the ADCC activities on K562 and L-1236 cells are 23.2% and 18.7%, respectively (see, FIG. 4). On the other hand, the activity was not virtually confirmed (see, FIG. 4) when the same operation was conducted by using the control antibody (Example 3) prepared from the peripheral blood of a mouse not immunized with the antigen and using a sample to which no antibody was added. Accordingly, it was clearly demonstrated that the tumor cells expressing CSPG5 protein can be damaged by an antibody against CSPG5 protein based on the ADCC activity.

The cytotoxic activity was obtained by mixing the antibody against CSPG5 protein used in the present invention, rabbit lymphocytes and the cell lines ($10^3$ cells) into which chromium 51 was incorporated, culturing the mixture for 4 hours, measuring the amount of chromium 51 released in the medium after culture, and estimating the cytotoxic activity on each of leukemia cell lines using the following formula*.

*Formula: Cytotoxic activity(%)=(the amount of chromium 51 released from K562 and L-1236 when an antibody against CSPG5 protein and rabbit lymphocytes were added)÷(the amount of chromium 51 released from target cells to which 1N hydrochloric acid was added)×100.

Example 5: Preparation of Monoclonal Antibody Against CSPG5 Protein

The antigen protein (hCSPG5 ECD-mIgG2aFc) (100 μg) represented by SEQ ID NO: 33 and prepared in Example 2 was mixed with the equivalent amount of MPL+TDM adjuvant (manufactured by Sigma). The mixture was used as an antigen solution per mouse. The antigen solution was intraperitoneally administered to 6-week old Balb/c mice (manufactured by Japan SLC, Inc.) and further administered 4 times every week to complete immunization. The spleens were excised out three days after the last immunization and ground by sandwiching each of the spleens between two sterilized slide glasses, washed with PBS (−) (manufactured by Nissui) and centrifuged at 1500 rpm for 10 minutes and then the supernatant was removed. This operation was repeated three times to obtain spleen cells. The obtained spleen cells and mouse myeloma cells SP2/0 (purchased from ATCC) were mixed in a ratio of 5:1. To the mixture, a PEG solution prepared by mixing RPMI 1640 medium (200 μL) containing 10% FBS and heated to 37° C. and 800 μL of PEG1500 (manufactured by Boehringer) heated to 37° C. was added. The mixture was allowed to stand still for 5 minutes to perform cell fusion. The mixture was centrifuged at 1700 rpm for 5 minutes. After the supernatant was removed, the cells were suspended with 150 mL of RPMI 1640 medium (HAT selection medium) containing 15% FBS and a HAT solution manufactured by Gibco in an equivalent of 2%, and seeded in fifteen 96-well plates (manufactured by NUNC) in an amount of 100 μL per well. The cells were cultured for 7 days at 37° C. in a 5% $CO_2$ condition to obtain hybridomas, i.e., fusion cells of spleen cells and myeloma cells.

A hybridoma was screened based on the binding affinity of the antibody produced by the hybridoma prepared for hCSPG5 ECD-mIgG2aFc. A 1 μg/mL solution of hCSPG5 ECD-mIgG2aFc protein prepared in Example 2 was added to a 96-well plate in an amount of 100 μL per well and allowed to stand still at 4° C. for 18 hours. After individual wells were washed three times with PBS-T, a 0.5% Bovine Serum Albumin (BSA) solution (manufactured by Sigma) was added in an amount of 400 μL per well and allowed to stand still at room temperature for 3 hours. The solution was removed and wells were washed three times with 400 μL of PBS-T per well. Then each culture supernatant of the hybridomas obtained above was added in an amount of 100 μL per well and allowed to stand still at room temperature for 2 hours. After individual wells were washed three times with PBS-T, HRP-labeled anti-mouse IgG (H+L) antibody (manufactured by Invitrogen) diluted 5000 fold with PBS was added in an amount of 100 μL per well and allowed to stand still at room temperature for one hour. After the wells were washed three times with PBS-T, a TMB substrate solution (manufactured by Thermo) was added in an amount of 100 μL per well and allowed to stand still for 15 to 30 minutes to perform a chromogenic reaction. After the color was generated, 1 N sulfuric acid was added in an amount of 100 μL per well to terminate the reaction. The absorbance values at 450 nm and 595 nm were measured by an absorption spectrometer. As a result, hybridomas producing antibodies exhibiting high absorbance values were screened.

The screened hybridomas were added to a 96-well plate in a ratio of 0.5 cell per well and cultured. After one week, a hybridoma forming a single colony in wells were observed. The cells in these wells were further cultured. A hybridoma was screened based on the binding affinity of the antibody produced by the hybridoma cloned for CSPG5 protein. A 1 μg/mL solution of hCSPG5 ECD-mIgG2aFc protein prepared in Example 2 was added to a 96-well plate in an amount of 100 μL per well and allowed to stand still at 4° C. for 18 hours. After individual wells were washed three times with PBS-T, a 0.5% BSA solution was added in an amount of 400 μL per well and allowed to stand still at room temperature for 3 hours. The solution was removed and the wells were washed three times with PBS-T in an amount of 400 μL per well. Each of the culture supernatants of hybridomas obtained above was added in an amount of 100 μL per well and allowed to stand still at room temperature for 2 hours. After individual wells were washed three times with PBS-T, HRP-labeled anti-mouse IgG (H+L) antibody (manufactured by Thermo Fisher Scientific) diluted 5000 fold with PBS was added in an amount of 100 μl, per well and allowed to stand still at room temperature for one hour. After the wells were washed three times with PBS-T, a TMB substrate solution (manufactured by Thermo) was added in an amount of 100 μL per well and allowed to stand still for 15 to 30 minutes to perform a chromogenic reaction. After color was generated, 1 N sulfuric acid was added in an amount of 100 μL per well to terminate the reaction. The absorbance values at 450 nm and 595 nm were measured by an absorption spectrometer. As a result, 312 hybridoma cell lines producing monoclonal antibodies reactive to CSPG5 protein were obtained.

Subsequently, monoclonal antibodies reactive to the surface of a cell expressing CSPG5 protein were screened from the monoclonal antibodies. Specifically, $10^6$ cells (CHO-CSPG5) expressing CSPG5 protein and established in Example 2 were placed in a 1.5 mL-volume micro-centrifuge tube and centrifuged. To this, each of the hybridoma culture supernatants obtained above (100 μL) was added and allowed to stand still on ice for one hour. After washing with PBS, FITC-labeled goat anti-mouse IgG antibody (manufactured by Thermo Fisher Scientific) diluted 500 fold with PBS containing 0.1% FBS was added and the mixture was allowed to stand still on ice for one hour. After washing with PBS, fluorescence intensity was measured by a FACS Calibur (manufactured by BD). CHO cells (CHO-emp) expressing no CSPG5 protein were subjected to the same operation as above and used as a control. As a result, monoclonal antibodies whose fluorescence intensities are higher than the control, in other words, 18 monoclonal antibodies (#1 to #18)) reacting with the surface of the cell expressing CSPG5 protein, were screened.

Example 6: Characteristics of Screened Antibody (1) Antitumor Effect (ADCC Activity) of Monoclonal Antibody Against CSPG5 Protein on Cancer Cells The cytotoxic activities (ADCC activity) of monoclonal antibody #1 against CSPG5 protein screened above to cancer cells were evaluated. The hybridomas producing a monoclonal antibody were cultured by using hybridoma SFM (manufactured by Thermo Fisher Scientific) medium. The resultant supernatant was purified by use of Hitrap proteinA SepharoseFF (manufactured by GE Healthcare), replaced with PBS (−), and filtered by a 0.22 μm filter (manufactured by Millipore), and the resultant product was used as an antibody for measuring activity. Human leukemia cell line K562 and malignant lymphoma cell line L-1236 ($10^6$ cells for each) were collected separately in 50 mL-volume centrifuge tubes and 100 μCi of chromium 51 was added and incubated at 37° C. for 2 hours. Thereafter, the cells were washed three times with RPMI 1640 medium containing a 10% FBS, and added to a 96 well (with a V-shape bottom) plate in a ratio of $10^3$ cells per well and used as target cells. To this, the above purified antibody was added in an amount of 1 μg per cell, and mouse lymphocytes ($2\times10^5$ cells) separated from a mouse spleen were added and cultured at 37° C. in a 5% $CO_2$ condition for 4 hours. After culture, the amount of chromium 51 released from the damaged tumor cells in the culture supernatant was measured and the ADCC activity of anti-CSPG5 monoclonal antibody to cancer cells was calculated.

(2) Antitumor Effect (CDC Activity) of Monoclonal Antibody Against CSPG5 Protein on Cancer Cells The cytotoxic activity (CDC activity) of monoclonal antibody #1 against CSPG5 protein screened as described above on cancer cells was evaluated. Blood was taken from a rabbit, placed in an Eppendorf tube, allowed to stand still at room temperature for 60 minutes, and centrifuged at 3000 rpm for 5 minutes to prepare a serum for CDC activity measurement. Human leukemia cell line K562 and malignant lymphoma cell line L-1236 ($10^5$ cells for each) were collected separately in 50 mL-volume centrifuge tubes and 100 μCi of chromium 51 was added, incubated at 37° C. for 2 hours, washed three times with RPMI medium containing a 10% FBS, suspended with RPMI medium containing 50% of rabbit serum prepared as described above and added to a 96 well (with a V-shape bottom) plate in a ratio of $10^3$ cells per well. To this, the monoclonal antibody #1 used in the above step (1) was added individually in an amount of 1 μg and cultured at 37° C., in a 5% $CO_2$ condition for 4 hours. After culture, the amount of chromium 51 released from damaged tumor cells in the culture supernatant was measured and the CDC activity of anti-CSPG5 monoclonal antibody in hybridoma supernatant to K562 and L-1236 was calculated. As a result, monoclonal antibody #1 has a CDC activity of 26%. The monoclonal antibody prepared in Example 5 and reacting with CSPG5 protein itself but does not react with the surface of cancer cells, was subjected to the same operation. As a result, no cytotoxic activity was observed. Accordingly, it was demonstrated that the monoclonal antibody (#1) against CSPG5 protein damages tumor cells expressing CSPG5 protein also based on the CDC activity.

Example 7: In-Vivo Antitumor Effect of Anti-CSPG5 Monoclonal Antibody in Mice

The in-vivo antitumor effect of monoclonal antibody #1 (obtained above) against CSPG5 protein in a cancer-bearing mouse was evaluated. The antibody used herein was obtained by purifying each hybridoma culture supernatant by a column, in the same manner as above.

The antitumor effect of the monoclonal antibody #1 against CSPG5 protein was examined using a cancer-bearing mouse obtained by grafting mouse-derived leukemia cell line EL4-CSPG5, which expresses CSPG5 protein and was established in Example 3-(2). To the subcutaneous portion of the back of each of thirty C57BL/6 mice (manufactured by Japan SLC, Inc.), EL4-CSPG5 cells ($10^6$ cells/mouse) were grafted and the mice were allowed to grow until a tumor reached a size of about 7 mm in diameter. To ten cancer-bearing mice out of these mice, monoclonal antibody #1 against CSPG5 protein was intraperitoneally administered in a dose of 100 μg (100 μL) per mouse. To another ten mice, a monoclonal antibody, which was prepared in Example 5 and reacts with CSPG5 protein itself but does not react with the surface of cancer cells, was intraperitoneally administered in a dose of 100 μg (100 μL) per mouse. Thereafter, each antibody in the same dose was intraperitoneally administered to individual cancer-bearing mice once every three days for three times in total. Every day, the size of tumors was measured to observe the antitumor effect. PBS (−) was administered in place of the antibody to the remaining ten cancer-bearing mice, and they were used as a control group. As a result of observation of the antitumor effect, in the group to which the monoclonal antibody (#1) against CSPG5 protein was administered, the tumor volume was reduced to about 90% on Day 10 and about 70% on Day 20 and 60-some % on Day 30 based on the tumor volume at the initial day of administration of the antibody as 100%. In contrast, in the control group, the tumor volume was increased up to about 260%, 350% and 550% on Day 10, Day 20 and Day 30, respectively. In the group to which a monoclonal antibody, which reacts with CSPG5 protein itself and does not react with the surface of cancer cells, was administered, the antitumor effect was not obtained and the tumor volume was increased in the same manner as in the control group. It was demonstrated from the results that the monoclonal antibody (#1) against CSPG5 protein exerts a strong in-vivo antitumor effect on the leukemia cancer cells expressing CSPG5 protein. The size (volume) of the tumor was calculated in accordance with the formula:

Major axis×Minor axis×Minor axis×0.5.

INDUSTRIAL APPLICABILITY

The antibody of the present invention is useful for treating and/or preventing cancer.

All publications, Patents and Patent Applications cited in the specification are incorporated in the specification in their entirety by reference.

The invention claimed is:

1. A method for treating cancer, said method comprising:
administering to a subject a therapeutically effective amount of an antibody capable of binding to the extracellular region of CSPG5 protein expressed on the surface of cancer cells to treat the cancer,
wherein the CSPG5 protein comprises the amino acid sequence of SEQ ID NO: 8, 4, 6, 10, or 12,
wherein the antibody has a cytotoxic effect, wherein the cytotoxic effect comprises antibody-dependent cell-mediated cytotoxicity (ADCC) and/or complement-dependent cytotoxicity (CDC), with the proviso that the cancer is not a brain tumor; and
wherein the cancer is selected from the group consisting of breast cancer, lung cancer, leukemia, malignant lymphoma, adenocarcinoma, mastocytoma, squamous cell carcinoma, melanoma, and neuroblastoma.

2. The method according to claim 1, wherein the antibody is a monoclonal antibody.

3. The method according to claim 2, wherein the antibody is a human antibody, a humanized antibody, or a chimeric antibody.

4. The method according to claim 2, wherein the antibody is IgG.

5. The method according to claim 2, wherein the antibody is IgG1 or IgG3.

6. The method according to claim 1, wherein the cancer is leukemia.

7. The method according to claim 1, wherein the cancer is malignant lymphoma.

8. The method according to claim 2, wherein the cancer is leukemia.

9. The method according to claim 2, wherein the cancer is malignant lymphoma.

10. The method according to claim 2, wherein the antibody is administered in a composition further comprising a carrier.

11. The method according to claim 1, wherein the cancer is selected from the group consisting of breast cancer, lung cancer, adenocarcinoma, mastocytoma, squamous cell carcinoma, melanoma, and neuroblastoma.

12. The method according to claim 11, wherein the antibody is a monoclonal antibody.

13. The method according to claim 12, wherein the antibody is a human antibody, a humanized antibody, or a chimeric antibody.

14. The method according to claim 12, wherein the antibody is IgG.

15. The method according to claim 12, wherein the antibody is IgG1 or IgG3.

16. The method according to claim 12, wherein the antibody is administered in a composition further comprising a carrier.

17. The method according to claim 1, wherein the subject is a human.

18. The method according to claim 1, wherein the subject is a mammal.

19. The method according to claim 1, wherein the antibody binds to an epitope within amino acids 1-420 of SEQ ID NO:8.

* * * * *